United States Patent
Sundermeyer et al.

(10) Patent No.: US 12,221,456 B2
(45) Date of Patent: Feb. 11, 2025

(54) METAL COMPLEXES HAVING TRIAZENIDO LIGANDS AND USES THEREOF FOR DEPOSITING METALS FROM THE GAS PHASE

(71) Applicant: Umicore AG & Co. KG, Hanau-Wolfgang (DE)

(72) Inventors: Joerg Sundermeyer, Marburg (DE); Susanne Pulz, Marburg (DE); Fabian Schroeder, Hameln (DE)

(73) Assignee: Umicore AG & Co. KG, Hanau-Wolfgang (DE)

( * ) Notice: Subject to any disclaimer, the term of this patent is extended or adjusted under 35 U.S.C. 154(b) by 1060 days.

(21) Appl. No.: 16/771,867

(22) PCT Filed: Dec. 12, 2018

(86) PCT No.: PCT/EP2018/084628
§ 371 (c)(1),
(2) Date: Jul. 13, 2020

(87) PCT Pub. No.: WO2019/115646
PCT Pub. Date: Jun. 20, 2019

(65) Prior Publication Data
US 2020/0392171 A1    Dec. 17, 2020

(30) Foreign Application Priority Data
Dec. 15, 2017    (EP) .................................... 17207806

(51) Int. Cl.
*C23C 16/18*    (2006.01)
*C07F 1/08*    (2006.01)
(Continued)

(52) U.S. Cl.
CPC ............ *C07F 15/0053* (2013.01); *C07F 1/08* (2013.01); *C07F 5/00* (2013.01); *C07F 5/003* (2013.01);
(Continued)

(58) Field of Classification Search
CPC ..................................................... C23C 16/18
See application file for complete search history.

(56) References Cited

U.S. PATENT DOCUMENTS

| 3,386,985 A | 6/1968 | Brinckman et al. |
| 2014/0051878 A1* | 2/2014 | Sundermeyer .......... C07F 5/066 556/175 |

FOREIGN PATENT DOCUMENTS

| WO | WO 2004/063233 | * | 7/2004 |
| WO | WO-2004063233 A2 | | 7/2004 |

OTHER PUBLICATIONS

Brinckman et al., "Metal-Nitrogen Bonding. Covalent Complexes of 1,3-Dimethyltriazene with Elements of Groups I, II, III, IV, and V", Inorganic Chemistry, vol. 4, No. 7, Jul. 1965, pp. 936-942.
(Continued)

*Primary Examiner* — Elizabeth A Burkhart
(74) *Attorney, Agent, or Firm* — Faegre Drinker Biddle & Reath LLP

(57) ABSTRACT

The invention relates to the use of a metal complex, which has at least one ligand of the formula $R^1$—$N_3$—$R^2$, wherein $R^1$ and $R^2$ are hydrocarbon moieties, for depositing the metal or a compound of the metal from the gas phase. The invention further relates to methods for depositing metals from the metal complexes, and to metal complexes, substituted triazene compounds and to methods for the production thereof.

10 Claims, 24 Drawing Sheets

Figure 1:
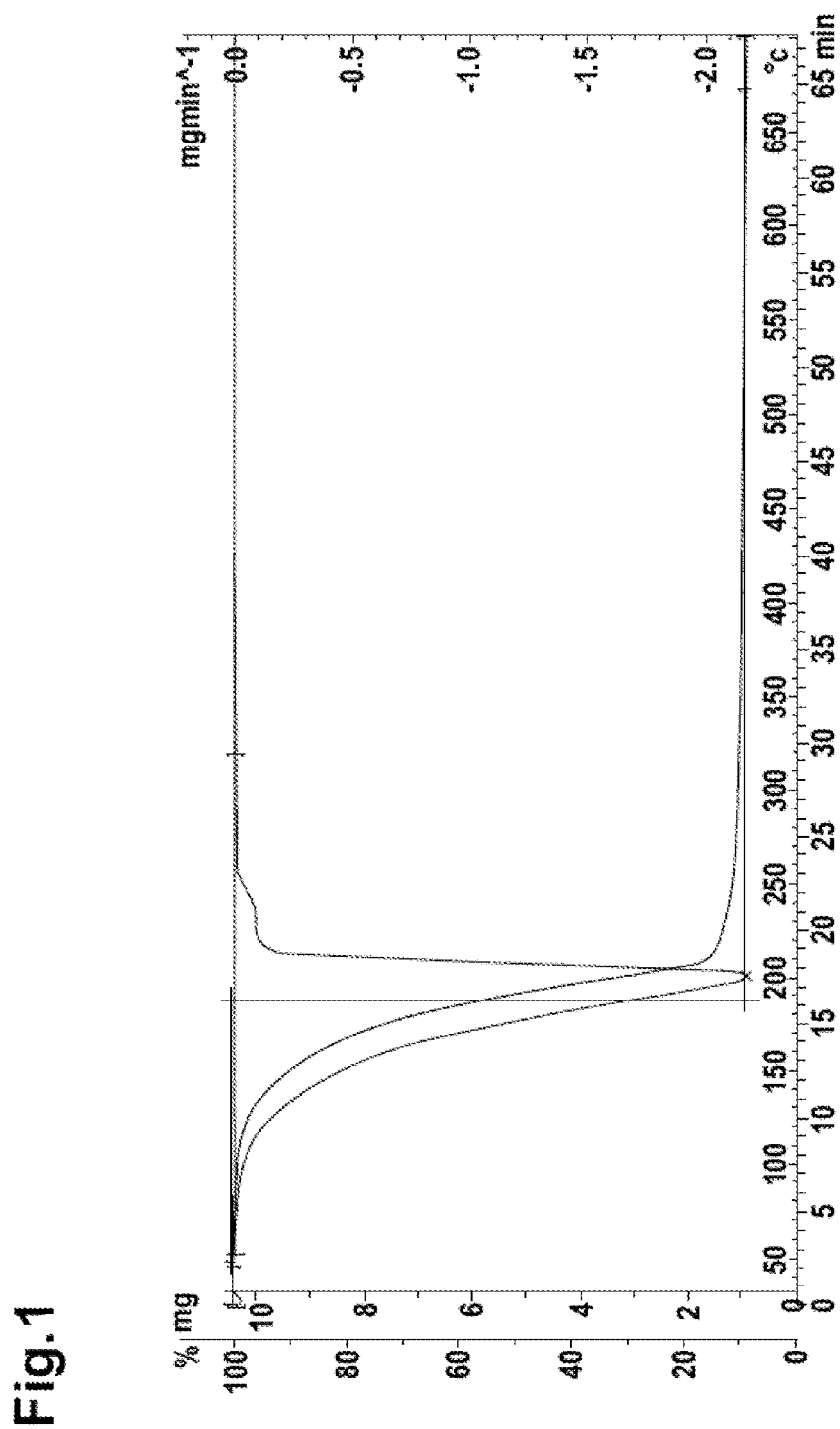

(51) Int. Cl.
   C07F 5/00    (2006.01)
   C07F 5/06    (2006.01)
   C07F 15/00   (2006.01)
   C07F 15/06   (2006.01)
(52) U.S. Cl.
   CPC ............ *C07F 5/069* (2013.01); *C07F 15/065* (2013.01); *C23C 16/18* (2013.01)

(56) References Cited

OTHER PUBLICATIONS

Dirk Pfeiffer et al,. "Synthesis, structure, and characterization of lanthanide complexes bearing 1,3-diphenyltriazenido ligands" Journal of Organometallic Chemistry., CH, vol. 588, No. 2, Oct. 1, 1999, pp. 167-175.

E G Rukhadze et al,. "Triazene chelates. III. Chelates of alkyl aryl triazenes" Zhurnal Obshchei KHIMII, vol. 39, No. 2, Jan. 1, 1969, pp. 303-306.

Khaled Soussi et al. "Asymmetrically substituted triazenes as poor electron donor ligands in the precursor chemistry of iron(II) for iron-based metallic and intermetallic nanocrystals" Dalton Transactions, GB, vol. 46, No. 38, Jan. 1, 2017, pp. 13055-13064.

Oussama M. El-Kadri et al,. "Film growth precursor development for metal nitrides. Synthesis, structure, and volatility of molybdenum(vi) and tungsten(vi) complexes containing bis(imido)metal fragments and various n itrogen donor ligands" Dalton Transactions, GB, No. 16, Jan. 1, 2006, pp. 1943-1953.

Richard H. Smith et al,. "1,3-Dialkyltriazenes: tautomeric equilibria and rates and products of decomposition" Journal of Organic Chemistry, vol. 54, No. 5, Mar. 1, 1989, pp. 1036-1042.

Dimroth Otto: "Ueber das Diazoamino-methan (Dimethyl-triazen)", Berichte Der Deutschen Chemischen Gesellschaft, Bd. 39, Nr. 4, 1. Nov. 1906 (Nov. 1, 1906), Seiten 3905-3912, XP055960706.

International Preliminary Report on Patentability for PCT/EP2018/084628 mailed Feb. 12, 2019.

Article: "Synthesis and Thermal Study of Hexacoordinated Aluminum (III) Triazenides for Use in Atomic Layer Deposition" by Samii et al.; ACS Publication 2021 (10pages).

Article: "Hexacoordinated Gallium (III) Triazenide Precursor for Expitaxial Gullium Nitride by Atomic Layer Deposition" by Rouf et al.; ACS Publications 2021 (10pages).

Article: "In Situ Activation of an Indium (III) Triazenide Precursor for Expitaxial Growth of Indium Nitride by Atomic Layer Deposition" by O'Brien et al.; ACS Publications 2020 (9pages).

* cited by examiner

METAL COMPLEXES HAVING TRIAZENIDO LIGANDS AND USES THEREOF FOR DEPOSITING METALS FROM THE GAS PHASE

CROSS-REFERENCE TO RELATED APPLICATIONS

This application is a national stage application (under 35 U.S.C. § 371) of PCT/EP2018/084628, filed Dec. 12, 2018, which claims benefit of European Application No. 17207806.5, filed Dec. 15, 2017, both of which are incorporated herein by reference in their entirety.

The invention relates to the use of a metal complex that has at least one ligand of the formula $R^1—N_3—R^2$, wherein $R^1$ and $R^2$ are hydrocarbon radicals, especially alkyl radicals, for depositing the metal or another compound of the metal from the gas phase. The invention further relates to methods for depositing metals from the metal complexes, as well as metal complexes, substituted triazenido compounds and methods for the production thereof.

PRIOR ART

Metal-organic vapor phase deposition, and especially metal-organic vapor phase epitaxy, are important methods for generating thin layers of metals or metal compounds on substrates. These methods are used in the semiconductor industry in particular. In this process, metal-organic compounds, optionally in combination with additional reactive compounds, are introduced into processing chambers where, under reduced pressure or normal pressure, a reaction takes place on the surface of heated substrates, leading to deposition of the layer. With such methods, a plurality of metal-containing layers, such as semiconductor crystals, amorphous layers, metallic compounds or metal layers, may be deposited on substrates. A review may be seen, for example, in the "Handbook of Thin Film Deposition—Processes and Technologies," 2nd Edition 2001, editor: Krishna Seshan, Chapter 4, pp. 151-203, by J. Zilko.

For many applications, in particular in the semiconductor industry, it is indispensable for such metal-containing layers to be produced in high purity. Even slight traces of impurities may impair the intended use.

However, only very few metal-organic precursor compounds are suitable for producing highly pure metal-containing layers. This is often due to the fact that a suitable metal-organic precursor compound should be transferable to the gas phase at a high temperature. However, many metal-organic compounds are thermally unstable. They decompose (disintegrate) at higher temperatures and therefore cannot be converted into the gas phase by heating or otherwise. It is problematic in this context that metal-organic compounds are often solids that have relatively high evaporation temperatures, at which decomposition processes take place, inter alia owing to the reactive organic ligands.

If a metal-organic compound can be vaporized, the temperature in the gas phase above the substrate, i.e. the target of the deposition, is usually further increased until decomposition takes place. However, even metal-organic compounds which can be converted into the gas phase are often not suitable for the deposition of metals. The reason for this is that the deposition of the metal on the substrate surface must take place in such a way that no impurities, not even minimal ones, are produced by components of the complex ligands, such as carbon, nitrogen or oxygen. This prerequisite too is often not met because, at the required high decomposition temperatures, a mixture of highly reactive intermediates, ionic radicals and radicals is formed, so that undesired side reactions often take place on the substrate surface.

Metal alkyl compounds are often used as precursor compounds for the deposition of metal-containing layers in the gas phase. An overview of suitable compounds is included in the above cited publication by J. Zilko. However, the alkyl compounds of many metals often have properties that impair the suitability for deposition reactions in the gas phase. On the one hand, it is disadvantageous that many pure metal alkyl compounds of the transition metals are unstable, prone to decay and not storable. On the other hand, they tend to introduce anionic carbon, which is bonded to the transition metal, into the layer in an undesirable manner. They often also have relatively high evaporation temperatures, which is disadvantageous for applications in vapor deposition.

There is therefore a continuous need for improved methods and materials for depositing metals and metal-containing layers by metal-organic vapor deposition.

Metal organic complexes having N-aryl and N,N'-diaryltriazenido ligands are known in the prior art. However, it is not disclosed in the prior art to use such complexes for the deposition of metals from the gas phase. This is not surprising, because such metal complexes with those ligands do not possess sufficient volatility and decomposition ability, which is absolutely necessary for use in the deposition of metals from the gas phase. Thus, in such reactions, nonvolatile carbon impurities would result.

Metal organic complexes having triazenido ligands substituted with aromatic radicals are described in a variety of publications. Virtually all of these publications, however, relate only to the synthesis and structure of such complexes, while practical applications of the compounds are described only in exceptional cases.

Methods are known for providing differently substituted precursor compounds for triazenide anions. In 1981, Brand and Roberts described the electronic configuration of 1,3-dialkyltriazenyl radicals and mentioned in a footnote that di-tert-butyl triazine can be represented starting from tert-butyl azide and tert-butyllithium. Neither experimental nor spectroscopic data were published.[1] Ethyl- and methyl-substituted triazenes were also described in 1983 by Smith and Michejda, the syntheses being carried out either with methyllithium or the Grignard reagent ethylmagnesium bromide.[2] Moreover, syntheses of different alkyl- and aryl-substituted triazenes and studies on tautomeric equilibria have been discussed in various publications.[3,4]

Alkaline earth metal and alkaline metal compounds of the triazenes are exclusively known from aryl-substituted systems. Crystallographically characterized compounds in all publications are solvated compounds and/or compounds, in which the corresponding metal is stabilized by means of TMEDA or [15]-Crown-5.[6-10]

Triazenido compounds having elements of the third main group have been known from the literature for several decades.

U.S. Pat. No. 3,386,985 includes a description of various metal-organic compounds that have various triazenido ligands, among them 1,3-dimethyltriazines. It is proposed to use the compounds as chain transfer reagents or inhibitors in polymerization methods. Methods for the deposition of metals are not described.

Brinckman et al.[11] describe metal-organic complexes with 1,3-dimethyltriazenide as ligands, the results of which largely coincide with those included in U.S. Pat. No. 3,386,985. No further explanations are given regarding practical uses of the complexes. The yields in the production methods are not more than 76% and are therefore still in need of improvement.

In addition, various complexes, both homoleptic and heteroleptic, with one and/or two aryl-triazenido ligands have been described in the literature.[12-16]

In the region of the transition metals, a plurality of triazenido compounds with aromatically substituted ligands is known, with early transition metals such as titanium and zirconium as well as late transition metals such as silver and copper being investigated as central atom.[6,17-23] Both homoleptic and heteroleptic, molecular or cationic cobalt complexes with aromatically substituted triazenido ligands have been described in connection with ESR measurements. Ruthenium compounds have also been reported in connection with theoretical calculations.[24-30]

Soussi et al.[5] describe the preparation of metal-organic iron complexes having alkyltriazenides as ligands and, for stabilization, TMEDA ligands (tetramethylethylenediamine). The complexes are prepared in a relatively complex method starting from $Fe[N(SiMe_3)_2]_2$ via the route of ligand exchange. The metal complexes are used for the production of intermetallic nanoparticles. The evaporation and decomposition behavior of the iron complexes when the temperature is increased is investigated by thermogravimetric analysis. It has been found that the four metal complexes have a low thermal stability, so that the complexes cannot be vaporized. When the temperature is raised to more than 200° C., solid residues remain, accounting for approximately 20 to 40 wt. % of the sample weight. In addition, when the temperature is raised to up to 200° C., the weight curve shows an irregular course, which is typical of chemical decomposition reactions. Hence, the metal complexes are not suitable as precursor compounds for the production of metal-containing gas-phase coatings.

Although various rare earth metal complexes are known from the literature, they are only known with sterically very demanding aryl-triazenido ligands.[31-33]

There is a continuous need in the art for methods and compounds useful for depositing metals and metal-containing layers in the gas phase that overcome the disadvantages described above.

OBJECT OF THE INVENTION

The invention is based upon the object of providing methods and compounds that overcome the disadvantages described above. The invention is based in particular on the object of providing novel and improved compounds in order to deposit metals and metal-containing layers from the gas phase.

The compounds should have a relatively high stability. The compounds should have a high vapor pressure and at the same time a low decomposition point. It should be possible to convert the compounds into the gas phase without substantial decomposition taking place. After conversion into the gas phase, i.e. at temperatures above the sublimation temperature or evaporation temperature, the compounds should decompose. The decomposition should preferably take place at a temperature that is only slightly above the sublimation temperature or evaporation temperature.

The compounds should generally have high stability and volatility at temperatures, at which deposition methods from the gas phase are usually carried out, in particular from 100° C. to 300° C. In particular, the compounds should be sublimable.

The invention is based in particular on the object of providing compounds which can be stably converted into the gas phase at temperatures of up to 100° C. and which decompose at higher temperatures, for example in the range from 100° C. to 400° C.

The compounds are intended to make it possible to deposit various metals and metal-containing compounds from the gas phase. The coatings should be highly purified. In particular, in conventional deposition methods, no undesired incorporation of carbon, oxygen or nitrogen into the coatings should take place.

The invention is furthermore based on the object of providing methods for producing such compounds that are as simple and efficient as possible. The reagents used should be as easy to access and safe to handle as possible. It should be possible to carry out the methods with high yields. The methods should lead to the desired products in as few steps as possible and should be able to be carried out under as gentle reaction conditions as possible. It is also intended to provide compounds, from which the volatile precursor compounds can be prepared in the simplest possible way.

DISCLOSURE OF THE INVENTION

Surprisingly, the object, on which the invention is based, is solved by applications, methods, metal complexes and further compounds according to the claims.

The object of the invention is the use of a metal complex that has at least one ligand L with the formula $R^1-N_3-R^2$, wherein $R^1$ and $R^2$ are hydrocarbon radicals, for depositing the metal or a compound of the metal from the gas phase. In this, the ligand L is formally an anionic ligand because the $N_3$ subunit carries a negative charge.

In this case, a solid layer, which consists of or contains the metal, is deposited on a substrate from the gas phase. The metal complex is used as a metal-organic precursor compound (precursor).

The metal from the metal complex is deposited in elemental form or in a targeted manner in the form of a compound of the metal. Thus, for example, nitrogen from the ligand or from a suitable reactant partner can be incorporated into a layer, so that a nitride of the deposited metal is formed. Preferably, the metal complex is first converted into the gas phase, or at least volatile intermediate products containing the metal are converted into the gas phase. In the gas phase, the temperature is usually increased further at reduced pressure, so that a (further) decomposition of the metal complex takes place. The decay may also be excited or assisted in a different way, for example by radiation. The decisive decomposition of the metal complex should take place only after conversion into the gas phase. This ensures that the metal complex is quantitatively present as much as possible in the gas phase and can be used to deposit the metal or a compound of the metal. Furthermore, the number of undesired side reactions can be reduced regularly if controlled decomposition takes place only in the gas phase.

In a preferred embodiment, the metal complex has at least one ligand L of the formula $R^1-N_3-R^2$p and at least one further ligand X. The further ligand X is preferably selected from halogen, H, CO and hydrocarbon ligands. The hydrocarbon ligands are in particular alkyl or alkenyl having 1 to 12 C atoms and aromatic hydrocarbons having 5 to 30 C atoms. The hydrocarbon ligand may be neutral or have a negative charge for this. The halogen may be F, Cl, Br or I, Cl being particularly preferred. When X=H, a hydridocomplex is present. This complex may have one or more ligands X, for example one, two or three ligands X. In this case, it is preferred that exactly one or two ligands X are present. If more than one ligand X is present, the ligands X may be identical or different from one another.

In a preferred embodiment, the metal complex has at least one ligand L with the formula $R^1$—$N_3$—$R^2$, in which $R^1$ and $R^2$ are alkyl radicals.

In a preferred embodiment, the metal complex has the formula (1):

$$M_x[(L^1)_a(L^2)_b(L^3)_c X_d] \quad (1)$$

wherein
the ligands L, that is $L^1$, $L^2$ and $L^3$, are independently of one another selected from radicals of the formula $R^1$—$N_3$—$R^2$, wherein $R^1$ and $R^2$ are hydrocarbon radicals,
wherein at least for $L^1$ the radicals $R^1$ and $R^2$ are alkyl radicals,
X is independently selected from H, halogen, CO and hydrocarbon ligands, in particular alkyl radicals having 1 to 12 C atoms and aromatic hydrocarbons having 5 to 30 C atoms,
x is an integer between 1 and 4, preferably 1 or 2,
a, b, c and d are integers, wherein
the sum a+b+c+d is at least x and is not greater than 12, preferably not greater than 6, in particular not greater than 4,
a is at least 1, preferably from 1 to 6, and is preferably 1 or 2,
b, c and d may equal 0, and preferably each is 0, 1 or 2. In this case, b is in particular 0 or 1 and c is preferably 0.

As is known to the person skilled in the art, the ratio of the ligands to the metal results from the oxidation state of the metal. In this, the ligand L is of the formula $R^1$—$N_3$—$R^2$, wherein $R^1$ and $R^2$ are hydrocarbon radicals, with a single negative charge. Thus, for example, a metal of oxidation state II, such as Co(II), in the formula (1) may be substituted with one or two ligands L.

In general, it is preferred that the complexes are as homogeneous as possible. The decay process is then often less complex, and as a result, the probability of undesirable side reactions occurring in the gas phase and in the coating reaction is lower. In particular, it is preferred that a complex has only one or two different types of ligands, for example only one type of the ligand L and one type X, or only two types of the ligand L. The complex as a whole as ligand L particularly preferably has only $L^1$ and $L^2$. Then c=0.

More preferably, the complex has only ligands L that are $L^1$. Then b=0 and c=0. In a preferred embodiment, the complex has no ligand X, so that d=0. Preference is also given here to embodiments in which c=d=0 or in which b=c=d=0. Such complexes have been found to often exhibit particularly good behavior in gas phase deposition processes, despite the low structural complexity.

In a preferred embodiment, the metal complex is homoleptic. In this case, the homoleptic complex has only one or more ligands L. The term "homoleptic" means that all ligands of a compound are identical. Homoleptic complexes are particularly preferred because the decomposition behavior in the gas phase is often more uniform and better to control than with heteroleptic metal complexes having different ligands. According to the invention, homoleptic complexes have been found to have particularly good properties with regard to stability and volatility, which is required for vapor deposition. In particular, advantageous properties for homoleptic complexes of In, Co, Cu and La have been found.

In another preferred embodiment, the metal complex is heteroleptic. This means that a metal complex may have two or more different ligands, in particular two, three or four different ligands. For this, two or more different ligands L of the formula $R^1$—$N_3$—$R^2$ may be present. Alternatively, at least one ligand L of the formula $R^1$—$N_3$—$R^2$ and at least one other ligand must be present. In a preferred embodiment, the heteroleptic metal complex comprises two or three different ligands. According to the invention, it has been found that, for example, heteroleptic ruthenium complexes are readily accessible and are suitable for the deposition of Ru from the gas phase.

In a preferred embodiment, the metal complex has only ligands L of the formula $R^1$—$N_3$—$R^2$.

In a further preferred embodiment, the metal complex additionally comprises further ligands. In this case, preferably no further ligands are present that impair the advantageous properties with regard to stability and volatility, or impair the deposition of the pure metal from the gas phase. Preferably, therefore, no further ligand is present that has a reactive element selected in particular from O, N, S or P. In particular, there is preferably no further ligand with an amine group, such as tetramethylethylenediamine (TMEDA). In one embodiment, there is preferably no ligand comprising a halogen. In a further preferred embodiment, there is no ligand having a structural element N—C—N or N aryl.

In a preferred embodiment, the metal complex has a metal atom and one to four ligands of the formula $R^1$—$N_3$—$R^2$, in particular one, two, three or four ligands. The metal complex may also have two, three, four or more metal atoms, with a correspondingly higher number of ligands being present. The stoichiometries of such metal complexes are well known. The radical $R^1$—$N_3$—$R^2$ is singly negatively charged.

The radicals $R^1$ and $R^2$ are hydrocarbon radicals. This means that they consist of the elements carbon and hydrogen. $R^1$ and $R^2$ can generally be selected independently of one another.

In a preferred embodiment, $R^1=R^2$. As a result, the compound overall can be particularly homogeneous. This can be advantageous in the deposition of metals from the gas phase because the decomposition process is less complex and fewer side reactions are to be expected.

In a preferred embodiment, $R^1$ and $R^2$ have, in the context of this application, independently of one another 1 to 25 C atoms, in particular 1 to 20 C atoms. In this case, it is particularly preferred for $R^1$ and $R^2$ to have, independently of one another, 1 to 15 C atoms, in particular 1 to 12 C atoms.

The $R^1$ and $R^2$ radicals may be independently selected from alkyl, alkenyl, aryl and araryl. In one specific embodiment, $R^1$ and $R^2$ are alkyl radicals. Preferably, the metal complex has at least one ligand L with the formula $R^1$—$N_3$—$R^2$, in which $R^1$ and $R^2$ are alkyl radicals. Alkyl radicals are preferred for all ligands L of the metal complex $R^1$ and $R^2$. The alkyl radicals may be branched, cyclic or unbranched.

In the context of this application, the alkyl radicals $R^1$ and $R^2$ may have, for example, 1 to 20 C atoms, in particular 1 to 15 C atoms or 1 to 12 C atoms. The alkyl radicals are particularly preferred to be relatively short-chain and to have 1 to 6 C atoms, in particular 1 to 4 C atoms.

In a preferred embodiment, all or part of the $R^1$ and/or $R^2$ radicals of the metal complex are branched and/or cyclic alkyl radicals. Preferred branched radicals here are tert-butyl and isopropyl, in particular tert-butyl. Preferred cyclic radicals are bulky radicals, such as adamantyl or cycloalkyl, in particular cyclohexyl.

$R^1$ and $R^2$ are particularly preferably selected from methyl, ethyl, propyl, isopropyl, tert-butyl and n-propyl. $R^1$ and $R^2$ are particularly preferably selected from methyl, ethyl and tert-butyl. In a preferred embodiment, $R^1$ and $R^2$ are tert-butyl.

In a preferred embodiment, the metal complex has at least one ligand that is tert-butyl-$N_3$-tert-butyl or tert-butyl-$N_3$-methyl. In a preferred embodiment, the metal complex has only ligands that are tert-butyl-$N_3$-tert-butyl and/or tert-butyl-$N_3$-methyl. The metal complex is preferably homoleptic.

The metal complex may have a further ligand X. The further ligand X is preferably selected from halogen, H, CO and hydrocarbon ligands. The hydrocarbon ligands are in particular alkyl radicals having 1 to 12 carbon atoms, in particular 1 to 4 carbon atoms, particularly preferably 1 or 2 carbon atoms. Methyl is particularly preferred. Also preferred as ligands X are aromatic hydrocarbons having from 5 to 30 carbon atoms, in particular from 6 to 12 C atoms, such as pentene, benzene or substituted benzene, such as cymene or various di- or tri-alkybenzenes.

The aromatic radicals X may be neutral or negatively charged. It is known that such aromatic ligands can stabilize metal complexes, for example complexes of Ru. The ligands may be alkenyl ligands, in particular having 1 to 12 C atoms. The halogen is preferably Cl.

The metal M may be a metal of the major and minor groups of the Periodic Table of the Elements (excluding alkaline metals). According to the invention, for the deposition of the metal or a compound of the metal from the gas phase, metal complexes which can have a suitable bandwidth of metals can be generally used.

It has been found that the use is particularly efficient when metal complexes of metals of groups 8, 9 and 10 of the periodic table (in particular Fe, Ru, Os, Co, Rh, Ir, Ni, Pd, Pt), group 13 (Al, Ga, In, Tl), group 10 (Cu, Ag, Au), group 12 (especially Zn; or Cd or Hg), of the lanthanoids (La, Ce, Pr, Nd, etc.) or the actinoids (Ac, Th, Pa, U, etc.) are used. The metal in the complex preferably has the oxidation state 1, 2 or 3.

In a preferred embodiment, the metal M is selected from Co, Ru, Cu, Al, Ga, Tl and La. Complexes of these metals with triazenido ligands are obtainable in a relatively simple manner with the method according to the invention. These metal complexes have been found to be highly suitable for deposition of the metals from the gas phase.

Metals selected from Al, In, Co, Cu and La are particularly preferably used. It has been found that metal complexes of these metals are particularly readily accessible and exhibit particularly advantageous properties in vapor deposition.

In a preferred embodiment, the metal M is selected from In, Co, Cu and Ru. There is in particular a need in the prior art for precursor compounds for the deposition of such metals from the gas phase.

In a preferred embodiment, the metal is M=Co. Co complexes have been found to be particularly highly sublimable, in which case low-molecular complexes can be evaporated at a relatively low temperature and virtually without residue.

In a preferred embodiment, the metal is M=In. It has been found that complexes are particularly readily sublimable or evaporable, wherein it is possible to evaporate a particular fraction at a relatively low temperature. In a preferred embodiment, the In-complex is liquid at 25° C. The compound In(dbt)Me₂ (formula 9a, example 8) was found to be liquid at 25° C. In-complexes that can easily be converted into the gas phase are particularly advantageous because, in the prior art, In-alkyl compounds such as trimethylindium are generally used, which are solids at room temperature and are prone to uncontrolled, partially explosive autocatalytic decomposition.

In a preferred embodiment, the metal is M=Ru. Such complexes are advantageous because in the prior art only a few precursor compounds requiring improvement are available in order to convert and deposit Ru into the gas phase at a relatively low temperature. In a preferred embodiment, the Ru complex is liquid at 25° C. Thus, the compounds of formulas (14) and (16) (examples 14 and 16) were found to be liquid at 25° C., while other Ru complexes have very low melting points of less than 70° C. Liquid and solid Ru complexes that can easily be converted into the gas phase are particularly advantageous because in the prior art no Ru compounds are available that can be converted efficiently into the gas phase and used in such methods.

In a preferred embodiment, the metal is M=Cu. It was found that Cu(I) complexes of the composition [Cu($R^1$—$N_3$—$R^2$)], depending on the size of the radicals $R^1$ and/or $R^2$ are present as dimer (n=2, $R^1$=$R^2$=tert-Butyl) or as tetramer (n=4, R'=tert-Butyl, $R^2$=methyl) in the crystalline solid. The formation of such associations is typical of many metal compounds.

Nevertheless, both compounds are very readily sublimable, wherein it is possible for low-molecular complexes to be vaporized into the gas phase at a relatively low temperature and virtually without residue.

In a preferred embodiment, the metal is M=La. Such complexes are advantageous since, in the prior art, only a few precursor compounds requiring improvement are available in order to convert lanthanum or other lanthanoids having very high molecular weights into the gas phase at a relatively low temperature and to deposit them.

In a preferred embodiment, the metal complex has the formula (2):

$$M[(L^1)_a X_d] \quad (2)$$

wherein
$L^1$ has the formula $R^1$—$N_3$—$R^2$, wherein $R^1$ and $R^2$ are alkyl radicals with 1 to 12 C atoms,
X is selected from H, halogen, CO and alkyl having 1 to 6 C atoms,
a=2 or 3,
d=0 or 1, and
M is selected from In, Co, Cu, Al, Ga, Tl, and La.

In a preferred embodiment, the metal complex has one of the formulas (3) to (5):

$$M[(L^1)_2 X] \quad (3)$$

wherein
$L^1$ has the formula $R^1$—$N_3$—$R^2$, wherein $R^1$ and $R^2$ are alkyl radicals with 1 to 12 C atoms,
X is selected from H and alkyl of 1 to 6 C atoms, and
M=Al or Ga;

$$M[(L^1)_3] \quad (4)$$

wherein
$L^1$ has the formula $R^1$—$N_3$—$R^2$, wherein $R^1$ and $R^2$ are alkyl radicals with 1 to 12 C atoms, and
M=In, Tl or La;

$$M_x(L^1)_a \quad (5)$$

wherein
$L^1$ has the formula $R^1$—$N_3$—$R^2$, wherein $R^1$ and $R^2$ are alkyl radicals with 1 to 12 C atoms,
X is an integer between 1 and 4, and a is an integer between 2 and 8, with the proviso that a/x=1 or 2, and M=Co or Cu.

Here, in particular, when a/x=2, the metal is Co and the metal is Cu when a/x=1.

In a preferred embodiment, the metal complex has the formula (6):

$$(Ru[(L^1)X^1X^2]) \qquad (6)$$

wherein $L^1$ has the formula $R^1$—$N_3$—$R^2$, wherein $R^1$ and $R^2$ are alkyl radicals with 1 to 12 C atoms, $X^1$ is an aromatic hydrocarbon ligand having from 5 to 30 C atoms, and $X^2$ is selected not from any radical, H, halogen, CO and alkyl having 1 to 6 C atoms.

It has been found that the stability and volatility of the Ru complexes may be lower than that of other metals. Irrespective of this, elemental Ru can be separated from the gas phase with the Ru complexes. This is advantageous because there is a need in the art for Ru compounds suitable as precursor compounds in such methods. The Ru complexes can be used, for example, to incorporate Ru as a doping metal, as a liner metal or as a filling metal in materials for electronic applications.

In a preferred embodiment, the metal complex is liquid at 25° C. and atmospheric pressure (1013 mbar). Liquids are particularly suitable for such methods because the transition into the gas phase already takes place at low temperature, and because liquids are particularly easy to handle. In a preferred embodiment, the metal complex is solid at 25° C. and atmospheric pressure and has a relatively low evaporation temperature.

Preferably, the metal complex has a sublimation or evaporation temperature at atmospheric pressure that is less than 120° C., in particular less than 100° C.

Preferably, the transition to the gas phase is effected by evaporation or sublimation at a temperature that is less than 120° C., in particular less than 100° C. The evaporation or sublimation is preferably effected at reduced pressure in the range from $10^{-3}$ to 900 mbar, preferably in the range from $10^{-2}$ to 1 mbar, and in particular at $10^{-2}$ mbar.

In general, the pressure in the method according to the invention is preferably set in ranges which are customary for such methods. Thus, the method and the use are preferably carried out at a pressure in the range from $10^{-3}$ to 900 mbar, and particularly preferably in the range from $10^{-2}$ to 1 mbar, and in particular at $10^{-2}$ mbar. In the context of this application, parameters in the reaction in the gas phase, such as the evaporation, sublimation or decomposition temperatures, or temperatures, at which compounds are stable, are preferably measured at the reduced pressures that are set in such reactions, and in particular at a pressure of $10^{-2}$ mbar.

In a preferred embodiment, the metal complex is sublimable or vaporizable at atmospheric pressure and/or at reduced pressure in the gas phase without decomposition (decay) taking place. This means, for example, that up to 90 wt. %, up to 95 wt. % or up to 98 wt. % can be converted into the gas phase without decomposition taking place. Disintegration can be followed by customary methods, in particular SDTA (Simultaneous differential thermal analysis).

The metal complex is preferably thermally stable at atmospheric pressure, but in particular at reduced pressure in the gas phase at 100° C., more preferably at 120° C. or 150° C. This means that at such a temperature no substantial decomposition takes place yet or that at least not more than 5 wt. %, in particular not more than 2 wt. %, or not more than 1 wt. % are decomposed. Preferably, the metal complex undergoes transition to the gas phase below this temperature. The reduced pressure is in the range from $10^{-3}$ to 900 mbar, preferably in the range from $10^{-2}$ to 1 mbar, and in particular at $10^{-2}$ mbar.

In a preferred embodiment, the metal complex has a relatively low molecular weight. Relatively light complexes can often be better converted into the gas phase. The metal complexes described in the context of this application can advantageously be prepared with ligands that have a relatively low molecular weight. The molecular weight of the metal complex is preferably less than 600 g/mol, particularly preferably less than 450 g/mol, and very particularly preferably less than 350 g/mol.

The invention also relates to a method for producing coated substrates, comprising the steps of:

(a) providing a metal complex as described above, and (b) depositing the metal or a compound of the metal on the surface of the substrate by metal-organic vapor deposition.

In a preferred embodiment, the method is a metal-organic chemical vapor deposition (MOCVD). The metal-organic vapor phase deposition (MOCVD, "metal-organic chemical vapor deposition") is a coating method from the group of chemical vapor deposition (CVD) methods, in which the deposition of a solid layer on a substrate takes place from the chemical vapor phase using a metal-organic precursor compound (precursor).

In a preferred embodiment, the metal-organic vapor phase deposition is a metal-organic vapor phase epitaxy (MOVPE for "metal-organic vapor phase epitaxy," and also called "organo-metallic vapor phase epitaxy," OMVPE). Whereas any deposition on a substrate is possible with MOCVD, MOVPE is an epitaxy method and thus relates to crystalline growth on a crystalline substrate. The methods, especially MOVPE, are especially used for deposition of semiconductor materials.

The uses and methods according to the invention allow the metal or a compound of the metal to be deposited from the gas phase. The deposition is effected on a substrate. The metal-containing deposition is generally referred to as a layer or coating. The compound of the metal is preferably selected from semiconductor compounds, alloys, nitrides, phosphides, arsenids and silicides. Such compounds are obtained by known methods by the addition of further compounds in the gas phase, which can react with the metal under the conditions in the apparatus. For an overview, reference is likewise made to the above-cited publication by J. Zilko.

Methods of metal-organic vapor deposition and metal-organic gas phase epitaxy are preferably carried out as described below. The metal-containing layers are produced in a reaction chamber. A substrate to be coated is located therein and is heated to a high temperature. A gas flow with the metal complex as precursor compound and usually a carrier gas is introduced into the reaction chamber, where the precursor compound in the vapor phase is first broken down, and free radical groups attach to the substrate. Thermally activated, the radical groups have a certain freedom of movement on the substrate, until the metal atom is incorporated in the layer at a suitable location. The organic radical is saturated with elemental hydrogen such that a volatile organic compound is formed. The residual gas is discharged from the reaction chamber. It is preferred that the metal complex be converted into the vapor phase before introducing it into the reaction chamber. In a less preferable embodiment, it is also conceivable to evaporate a liquid containing the metal complex only when it is introduced into the reaction chamber.

Surprisingly, it has been found that the metal complexes described in the context of this application are highly suitable as precursor compounds for the deposition of metals from the gas phase. Surprisingly, they combine several advantageous properties which are required for such methods. They are highly stable, volatile and can be used in such a way that virtually no impurities arise during the deposition of the metal or a compound of the metal on a substrate.

The metal complex is preferably sublimated or vaporized in the process without decomposition taking place. While a solid is initially charged during the sublimation, a liquid or a solution is provided during the evaporation. Thus, there is preferably no disintegration or substantial disintegration during the conversion of the metal complex into the gas phase. The disintegration process can be followed by customary methods, in particular SDTA (simultaneous differential thermal analysis).

The relevant properties of a metal complex when the temperature is increased can be determined by thermogravimetric analysis (TGA), which can be carried out at normal pressure (1013 mbar) or at reduced pressure. In this case, it is preferred that the curve amount/temperature (with the same T increase, for example 5 or 10 K/min) shows a rectified profile. A sublimation is generally present when a rapid decrease in weight takes place at or above a sublimation temperature, and no residue or only little residue remains in the process. Preferably, the TGA curve does not show any significant drawbacks, such as bumps or dents.

The transfer of the metal complex into the gas phase preferably takes place as completely as possible. In this case, it is preferred for the smallest possible residue to remain in the case of the TGA at atmospheric pressure and/or reduced pressure, for example less than 20 wt %, less than 10 wt %, less than 5 wt %, or in particular less than 3 wt %, based on the amount of metal complex used. The residue corresponds to the plateau value, at which this approximates the weight of the residue at a further T increase to, for example, up to 500° C., 600° C. or 700° C. If the weight of the residue is (clearly) below the weight of the metal in the charged compound, this indicates sublimation or evaporation of the compound. Preferably, during the TGA at least 50 wt %, in particular at least 80 wt % or at least 90 wt % of the metal is converted into the gas phase. It is generally advantageous for reasons of efficiency if the metal is vaporized quantitatively.

It has been found that the metal complexes according to the invention are relatively stable. They are preferably stable at room temperature and thereby durable for as long as desired. In a preferred embodiment, the metal complex is thermally stable at temperatures up to 100° C.

In the case of the TGA at atmospheric pressure, a mass loss of 3% preferably takes place only at a temperature above 80° C., preferably above 100° C., and particularly preferably above 120° C. The mass loss of 3% preferably takes place at a temperature between 80° C. and 220° C., in particular between 80° C. and 160° C.

Preferably, the metal complex decomposes under conditions of vapor deposition, usually carried out at reduced pressure, at temperatures between 100° C. and 400° C., in particular between 120° C. and 300° C., or between 150° C. and 250° C. The complex is preferably present in the gas phase at these temperatures. The reduced pressure is in the range from $10^{-3}$ to 900 mbar, preferably in the range from $10^{-2}$ to 1 mbar, and in particular at $10^{-2}$ mbar Decomposition is often effected in an exothermic reaction. The decomposition in this range is preferably complete.

The metal complex is preferably decomposed only after conversion to the gas phase. The decomposition should preferably take place at a temperature above the sublimation temperature or evaporation temperature. Preferably, the decomposition temperature is not more than 200° C., not more than 100° C., or preferably not more than 50° C. above the sublimation temperature or evaporation temperature, especially at reduced pressure as indicated above. The metal complex is preferably decomposed completely, or to 50%, at this decomposition temperature. If decomposition takes place at a temperature that is not too far above the sublimation or evaporation temperature, the deposition in the gas phase can often be carried out with particular efficiency.

The elemental metal or the desired compound of the metal in pure form is preferably obtained during the deposition from the gas phase. This means that no or negligible impurities can be determined, for example less than 500 ppb, less than 100 ppb or less than 10 ppb. The purity of the deposited metal or of the metal-containing compound can be determined by customary methods, for example by secondary ion mass spectrometry.

In a further preferred embodiment, the coating contains at least one further atomic component, in particular at least one further metal, or an element selected from Si, N, P or As. It is thus possible according to known methods to incorporate further metals or elements into the coating in order to obtain corresponding alloys or compounds.

The invention also relates to a method for producing a metal complex according to the invention, or usable according to the invention, comprising the steps of
    (A) providing a compound of the formula $R^1$—$(N_3)A$-$R^2$, wherein A is selected from H or an alkaline metal, in particular Li, Na or K, particularly preferred Li, and
    (B) bringing into contact with a compound of the metal.

The compound of formula $R^1$—$(N_3)A$-$R^2$ then reacts with the compound of the metal to form the metal complex. This reaction is preferably carried out in a single step. Here, A is preferably alkali, in particular Li. The metal complexes and in particular the radicals $R^1$, $R^2$ and A are selected as described above.

The compound of the metal used in step (B) is preferably a metal salt, a metal-organic compound or another metal complex of the metal. The other metal complex preferably does not have a triazenido ligand, especially no ligand L of the formula $R^1$—$N_3$—$R^2$ in which $R^1$ and $R^2$ are hydrocarbon radicals.

In a preferred embodiment, the method for producing the metal complexes comprises the step of creating the compound of the formula $R^1$—$(N_3)A$-$R^2$ from the compounds $R^1$—$N_3$ and $AR^2$, with A being an alkali metal, before Step (A). The entire process is preferably carried out in a single reaction mixture (as a "one-pot reaction").

An object of the invention is also a method for the production of a compound of the formula $R^1$—$(N_3)A$-$R^2$ in a reaction mixture that contains the compounds $R^1$—$N_3$ and $AR^2$, wherein A is an alkaline metal, preferably Li. The radicals $R^1$, $R^2$ and A are selected as described above.

The preparation of a compound of the formula $R^1$—$(N_3)A$-$R^2$ is preferably carried out in an inert solvent, in particular a hydrocarbon, such as pentane or hexane.

In one embodiment, the compound of formula $R^1$—$(N_3)A$-$R^2$ is purified after the reaction by evaporating the further components from the reaction mixture (method A). When A is an alkaline metal and is in diethyl ether, the product precipitates as solid and pure diethyl ether adduct (alkali salt) and can be separated by filtration (method B). The diethyl ether adduct can be completely freed of ether in vacuo, or it can, if desired, be converted into the corresponding neutral compound (with A=H) by hydrolysis with water.

According to the invention, it has been found that the method according to the invention makes it possible to produce metal complexes and the compounds of the formula $R^1$—$(N_3)$A-$R^2$, which are essential intermediates for complex synthesis, in a relatively simple manner, efficiently and with a high yield. In the preparation of the metal complex, a compound of the formula $R^1$—$(N_3)$A-$R^2$ is assumed. A may be a hydrogen radical H. The compound is then neutral in total. It has been found that with different metal salts efficient metal complex formation takes place under relatively simple conditions. For example, metal complexes of Al, Ga and In are obtainable from these compounds.

It has also been found that many metal complexes are accessible when the compound of the formula $R^1$—$(N_3)$A-$R^2$ is an alkaline metal salt. In this case, A is in particular Li, Na or K, and particularly preferably Li. Such compounds have been used according to the invention, for example, in order to prepare salts of Co, Cu or Ru in a simple manner and with high yield.

The compounds of the formula $R^1$—$(N_3)$A-$R^2$, wherein A=H or an alkaline metal, can be obtained in a simple manner by reacting the precursor compounds $R^1$—$N_3$ and A-$R^2$, wherein A is preferably an alkali metal. The reaction preferably takes place in an organic aprotic solvent, in particular in hydrocarbons, particularly preferably in pentane or hexane. An alkaline metal alkyl compound, in particular an organo lithium compound, is preferably slowly added dropwise. Preferably, the reaction mixture is first left at a low temperature, for example <15° C., and then allowed to warm to room temperature.

In the reaction to the metal complex, the compound of the formula $R^1$—$(N_3)$A-$R^2$ obtained in this manner, or the same compound from another origin, is brought into contact with a compound of the metal with sufficient reactivity, such as a metal salt or an organo-metallic compound of the metal, especially with a metal halogenide such as $CoCl_2$ or CuCl, or an organo-metallic compound such as $AlMe_3$ or $InMe_3$, or a metal hydride like $GaH_3$ $(OEt_2)$, or a precursor metal complex like $La(HMDS)_3$ (HMDS=hexamethyl disilazane) or $[RuCl_2(p-Cymen)]_2$. It has been found that, for example, in the case of cobalt, a reaction with a simple salt is already sufficient, while metal-organic precursor compounds are preferred for elements of the third main group. In order to convert ruthenium or lanthanum into metal complexes according to the invention, other metal complexes are preferably assumed. In all cases it was found that, starting from compounds of the formula $R^1$—$(N^3)$A-$R^2$, stable complexes with the corresponding ligands can be obtained in high yields.

Without being bound by theory, it is believed that the relatively weak N—N single bond in the metal complexes results in relatively uncomplicated thermal decomposition at relatively low temperatures. It is assumed here that $N_2$ is formed as a stable decomposition product, while further nitrogen-containing alkyl radicals are formed as molecular volatile compounds. All reaction products are not or little reactive and safe to handle, so that the method can be carried out in a relatively simple manner and with high yield.

It is also advantageous that the ligands in which $R^1$ or $R^2$ is, for example, methyl or tert-butyl have relatively low molecular weights. This leads to relatively good vaporizability or even sublimatability at relatively low temperatures. The use of just these two ligands is, as was surprisingly found, of particular importance for providing highly volatile metal compounds for ALD and MOCVD. Synthesis via the tert-butyl azide, which is easily accessible and especially technologically safe to handle, has considerable advantages over established 1.3-diazaallyl systems such as N,N'-dialkylacetamido or N,N'-dialkyl-N''-dialkylguanidato ligand systems. The decomposition temperatures of the triazenido complexes described below under ALD and CVD conditions are lower, and the undesirable carbon incorporation is less pronounced than in amidinato and guanidinato complexes.

In step (B), preference is given to using a metal-organic compound, in particular an organolithium compound, in particular alkyllithium having 1 to 6 C atoms, such as methyllithium. The compound is preferably used in dissolved form in ether. Pentane is preferably used as solvent. Preferably, in step (B), the compound of the metal is added to the compound of step (A), in particular continuously, such as by dropwise addition.

It is particularly advantageous according to the invention if a salt of the ligand, in particular the lithium salt, is used as intermediate. In the preparation of such organic salts, the selection of the solvent is important. The lithium salt of methyl-tert-butyl triazine in pentane thus precipitates as solvent when methyllithium dissolved in ether is used as the starting material. The lithium salt may be isolated by filtration, if desired. On the other hand, the lithium salt of di-tert-butyl triazine is soluble in pentane. After the end of the reaction, it can be isolated by evaporation of the clear reaction solution. In both syntheses, no by-products are obtained and the yields are above 80%. If desired, the neutral ligand di-tert-butyl triazine can readily be obtained by aqueous workup of the reaction mixture.

The lithium salts can be dried completely and processed further. They are soluble in nonpolar solvents such as pentane or toluene, but also in other common solvents such as diethyl ether or THF. They can therefore readily be used in such solvents in subsequent reactions for preparing the metal complexes. The corresponding neutral ligands with A=H, which are distillable liquids, can also be used in all customary solvents for subsequent reactions. The methods according to the invention and the intermediates therefore enable a simple and efficient production of metal complexes in high yields.

Starting from the compounds of the formula $R^1$—$(N_3)$A-$R^2$, various complex compounds are thus obtainable via the routes of salt, alkane (in particular methane), hydrogen or amine elimination. The two triazenido ligands are capable of complexing main group elements of the third or fifth main group, such as gallium, indium or antimony, in homoleptic or heteroleptic compounds. The production of complexes with secondary group elements, such as Co, Cu, Ru or La, is also readily possible.

Owing to the simple preparation of the intermediates and metal complexes, which can take place in a single reaction batch, for example, and since no problematic by-products occur, the process can easily be scaled up and carried out, for example, on an industrial scale. During conventional heating, the metal complexes are not decomposed in a device for vapor deposition, in particular a "bubbler" storage vessel, when heated to temperatures of, for example, 100° C. They then decompose, preferably only after the transition to the gas phase, at temperatures in the range from 100° C. to 400° C.

The invention also relates to a metal complex of formula (1):

$$M_x[(L^1)_a(L^2)_b(L^3)_c X_d] \quad (1)$$

wherein
the ligands L, that is $L^1$, $L^2$ and $L^3$, are independently of one another selected from radicals of the formula $R^1$—$N_3$—$R^2$, wherein $R^1$ and $R^2$ are hydrocarbon radicals,
 wherein at least for $L^1$ the radicals $R^1$ and $R^2$ are alkyl radicals,
X is independently selected from H, halogen, CO and hydrocarbon ligands, in particular alkyl radicals having 1 to 12 carbon atoms and aromatic hydrocarbons having 5 to 30 C atoms,
x is an integer between 1 and 4, preferably 1 or 2,
a, b, c and d are integers, wherein
 the sum a+b+c+d is at least x and is not greater than 12, preferably not greater than 6, in particular not greater than 4,
 a is at least 1, preferably from 1 to 6, and is preferably 1 or 2,
b, c and d may equal 0, and preferably each is 0, 1 or 2,
wherein at least one of the following conditions (i) to (ii) is satisfied:
 (i) M is selected from metals of the VIIIth subgroup and the lanthanides of the Periodic Table of the Elements, especially Ru, Co and La,
 (ii) at least one ligand L has at least one radical $R^1$ or $R^2$ that is tert-butyl.

In general, the metal complexes are those, which are described in the context of this application for the uses and methods. They therefore have in particular metals, ligands and radicals, i.e. especially M, $L^1$, $L^2$, $L^3$, $R^1$, $R^2$, X, x, a, b, c, d that are selected and described above. Preferred metal complexes are in particular those of the formula $M(L^1)_2$, $M(L^1)_3$, $M_2(L^1)_4$ and $M_2(L^1)_6$. In general, x is preferably a number between 1 and 2 and a+b+c+d is preferably a number between 2 and 6.

In a preferred embodiment, the metal complex has one of the formulas (7) to (20) as well as (102) to (115):

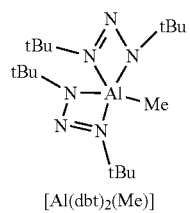
[Al(dbt)₂(Me)] (7)

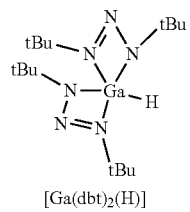
[Ga(dbt)₂(H)] (8)

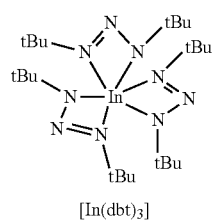
[In(dbt)₃] (9)

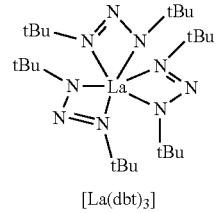
[La(dbt)₃] (10)

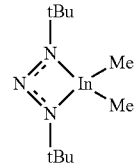
(9a)

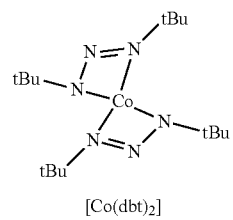
[Co(dbt)₂] (11)

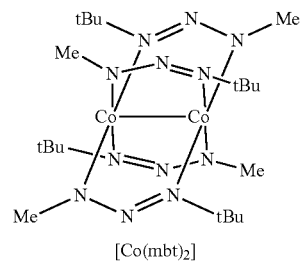
[Co(mbt)₂] (12)

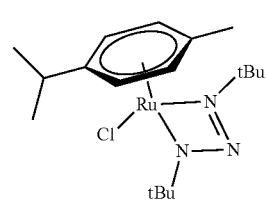
[Ru(dbt)(Cl)(p-cymene)] (13)

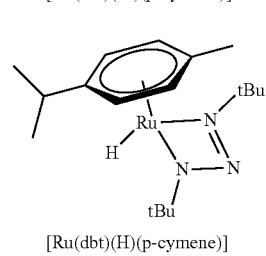
[Ru(dbt)(H)(p-cymene)] (14)

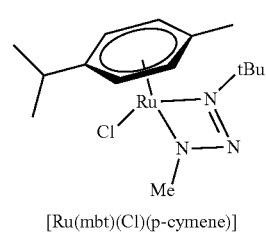
[Ru(mbt)(Cl)(p-cymene)] (15)

(16)
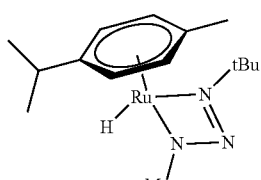
[Ru(mbt)(H)(p-cymene)]
(17)
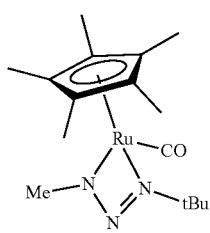
[Ru(mbt)(Cp*)(CO)]
(18)
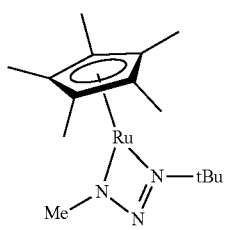
[Ru(mbt)(Cp*)]
(19)
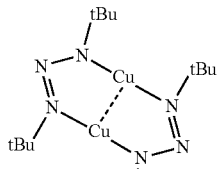
(20)
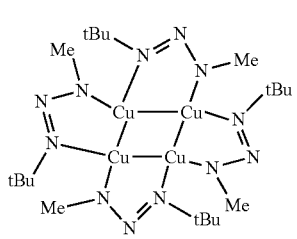
(102)
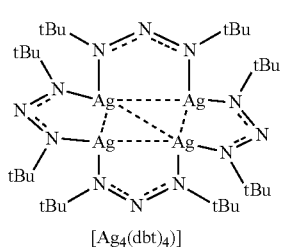
[Ag₄(dbt)₄]
(103)
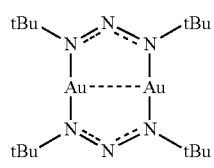
[Au₂(dbt)₂]
(104)
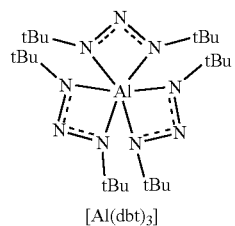
[Al(dbt)₃]
(105)
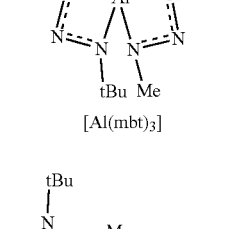
[Al(mbt)₃]
(106)
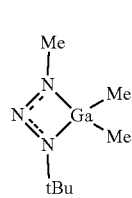
[Ga(dbt)Me₂]
(107)
[Ga(mbt)Me₂]
(108)
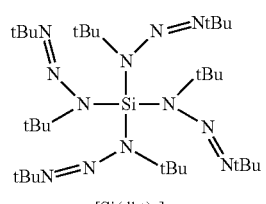
[Si(dbt)₄]
(109)
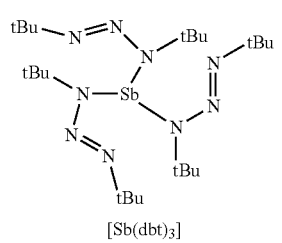
[Sb(dbt)₃]

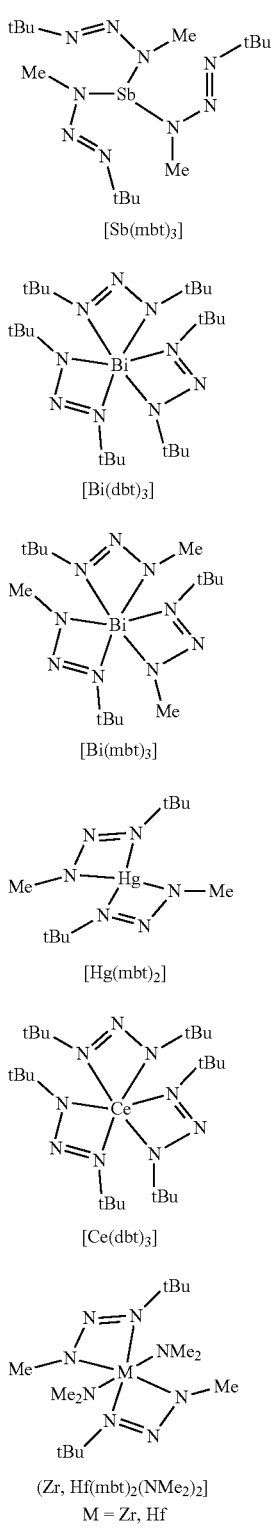

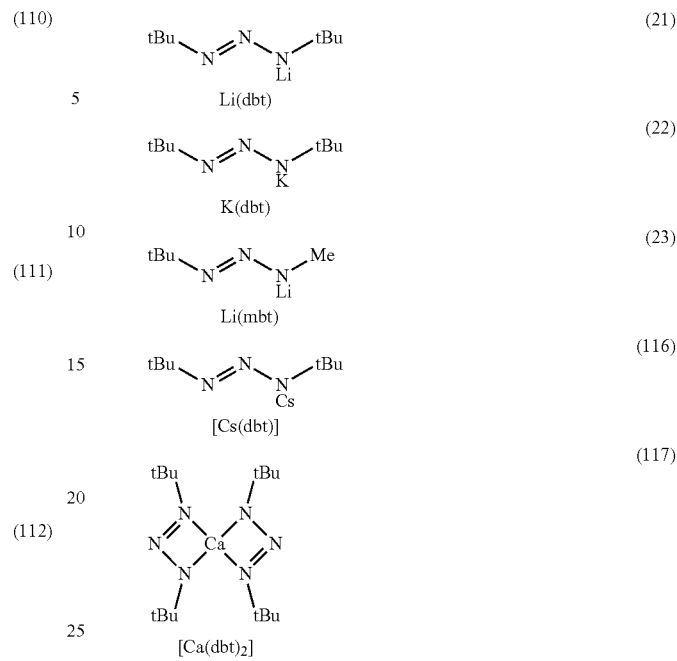

Compounds selected from tert-butyl-(N₃)H—CH₃ and compounds of the formula R¹—(N₃)A-R² are also object of the invention, wherein $R^1$ and $R^2$ are alkyl radicals and A is an alkali or earth alkali metal, especially Li, Na, Cs, Ca or K, particularly preferred Li.

In a preferred embodiment, the metal compound comprises one of the formulas (21) to (23) or (116) to (117):

The radicals $R^1$ and $R^2$ are selected as described above. The alkaline metal compounds are important intermediates in the preparation of the metal complexes. They can be prepared in a simple manner as described above and can be separated from the reaction mixture in a simple manner. The compounds are stable and can be converted into the corresponding neutral compounds (with A=H) by addition of water. As a result, they are also basically suitable in principle for other chemical reactions and for the production of complexes for applications other than the deposition of metals from the gas phase.

The applications, methods and compounds achieve the above-described aim. New and improved compounds are provided for separating metals from the gas phase. The compounds have a relatively high stability. In particular, compounds are provided, which have a high vapor pressure and at the same time a low decomposition point. As a result, the compounds can be converted into the gas phase without substantial decomposition taking place. In particular, the compounds have high stability and volatility at temperatures, at which deposition methods from the gas phase are usually carried out, in particular from 100° C. to 300° C. The compounds make it possible to deposit various metals from the gas phase, wherein the metal-containing coatings are highly pure. The invention further relates to simple and efficient methods for producing such compounds. The reagents used are easily accessible and safe to handle. The methods can be carried out with high yields. In a few steps, or even as a one-pot process, they result in the desired products and can be carried out under gentle reaction conditions.

FIGS. 1 to 13 show thermogravimetric analyses of metal complexes (TGA) prepared in accordance with embodiments 6, 7, 9 to 15 and 17 to 20. The TGA curve shows how the amount of metal complex used decreases with increasing temperature (in % and mg per min and ° C.). The first integral curve is also shown in each case. Furthermore, the plateaus of the starting amount (100%) and the remaining amount are shown, each of which is connected by a perpendicular at 50% weight reduction.

EXEMPLARY EMBODIMENTS

Overview of the Compounds Produced:

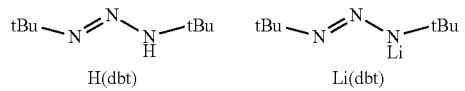

H(dbt)        Li(dbt)

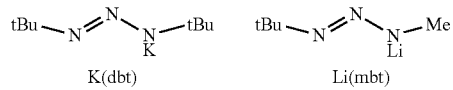

K(dbt)        Li(mbt)

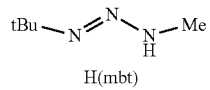

H(mbt)

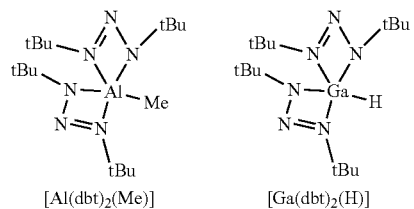

[Al(dbt)$_2$(Me)]        [Ga(dbt)$_2$(H)]

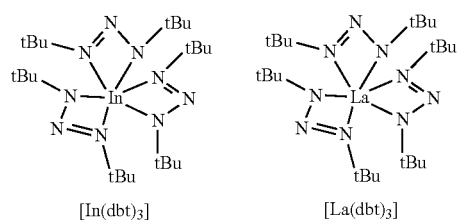

[In(dbt)$_3$]        [La(dbt)$_3$]

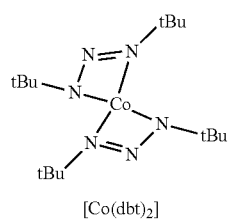

[Co(dbt)$_2$]

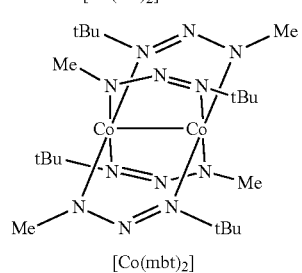

[Co(mbt)$_2$]

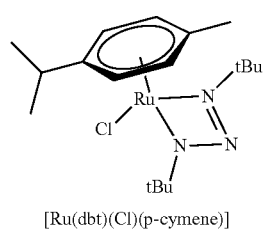

[Ru(dbt)(Cl)(p-cymene)]

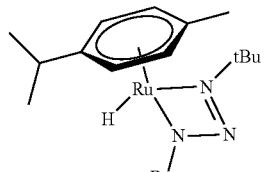

[Ru(dbt)(H)(p-cymene)]

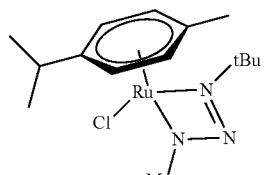

[Ru(mbt)(Cl)(p-cymene)]

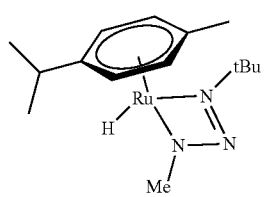

[Ru(mbt)(H)(p-cymene)]

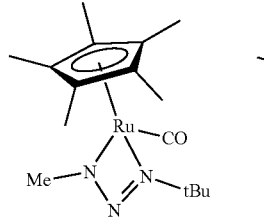 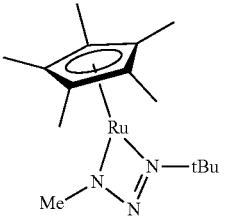

[Ru(mbt)(Cp*)(CO)]        [Ru(mbt)(Cp*)]

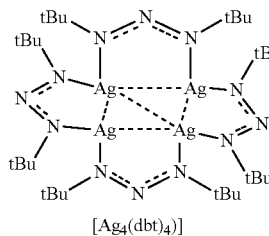 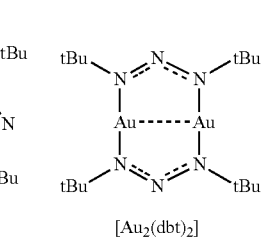

[Ag$_4$(dbt)$_4$]        [Au$_2$(dbt)$_2$]

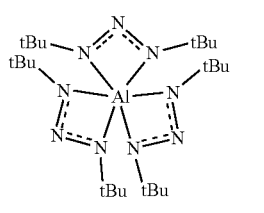 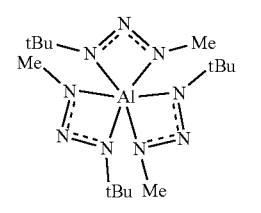

[Al(dbt)$_3$]        [Al(mbt)$_3$]

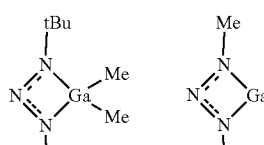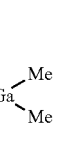

[Ga(dbt)Me$_2$]        [Ga(mbt)Me$_2$]

-continued

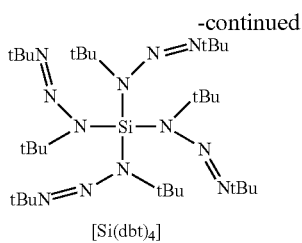

[Si(dbt)₄]

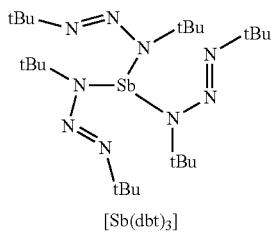

[Sb(dbt)₃]

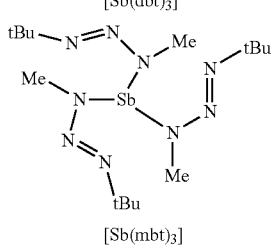

[Sb(mbt)₃]

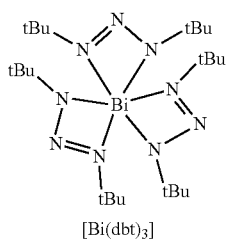

[Bi(dbt)₃]

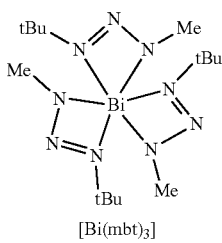

[Bi(mbt)₃]

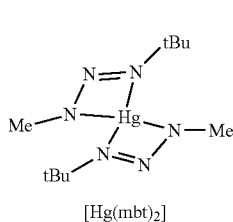

[Hg(mbt)₂]

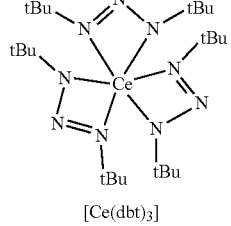

[Ce(dbt)₃]

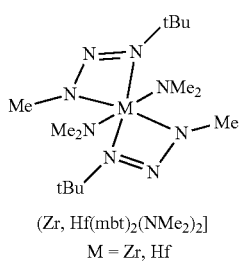

(Zr, Hf(mbt)₂(NMe₂)₂)
M = Zr, Hf

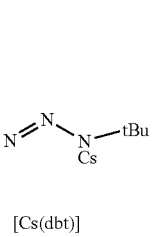

[Cs(dbt)]

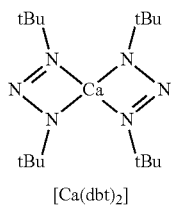

[Ca(dbt)₂]

Example 1: Tert-Butyl Azide

In general, organic azides are classified as explosive on the basis of two criteria, both conditions being empirical limits of explosivity.

1) [(quantity (N atoms)+quantity (O atoms))/quantity (C atoms)]<3
2) Percentage by weight of acidic nitrogen>25 ω %

According to both criteria, the tert-butyl azide described here should be classified as explosive material. However, accidents in representation or handling are not known. In addition, it is a liquid that can be distilled at 79° C. for purification and has an N₂ separation temperature of approximately 550° C., which is comparatively high for organic azides.

There are several synthetic approaches that have been reported since the end of the 1960s. For example, one approach starts out from tertbutyl chloride that is converted with NaN₃ and ZnCl₂ as the catalyst in CS₂.[34] Moreover, in another synthetic access, tertbutyl nitrate is converted with LiN₃ in DMF.[35,36] Both approaches may lead to various complications due to incomplete reactions or incomplete separation of the by-products. Furthermore, the use of carbon disulfide should be avoided due to the high toxicity. Therefore, an approach starting with tert-butanol was investigated, in which the alcohol is reacted with NaN₃ in a mixture of water and sulfuric acid.[37] Upscaling of the reaction to the tert-butyl azide up to several 100 g according to the literature is possible without problems and safely. Nevertheless, it should always be borne in mind with this synthesis route that HN₃ is formed in the reaction mixture, which should absolutely be handled in generously diluted form.

1.1 Synthesis of Tertbutyl Azide

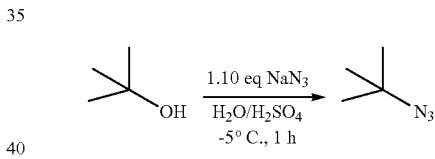

75 mL H₂O and 50 mL concentrated H₂SO₄ were submitted at −5° C. NaN₃ (9.80 g, 151 mmol, 1.10 eq) was slowly added with a solids dispenser. The colorless suspension was stirred for 15 min and allowed to warm to 0° C. tBuOH (10.2 g, 137 mmol, 1.00 eq) was slowly added in drops via a dropping funnel. The solid present in the reaction mixture dissolved slowly in the process. The reaction solution was stirred at RT for 16 h and transferred to a separating funnel in order to achieve separation of the phases. The aqueous phase was separated and immediately neutralized with NaOH (2 m). The organic phase was washed twice with 20 mL of NaOH (2 m) each, then dried over Na₂SO₄. The desired product was recondensed and could be obtained with a yield of 69% (9.40 g, 94.8 mmol) in the form of a colorless liquid.

Example 2: Synthesis of H(dbt) and Li(dbt)

2.1 Synthesis of Li(dbt)—Method 1

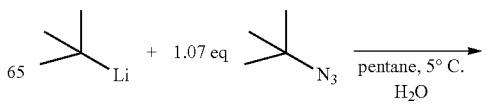

-continued

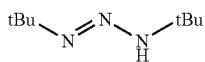

tBuN₃ (10.17 g, 102.6 mmol, 1.00 eq) was placed in 100 mL pentane and cooled to 5° C. Within one hour, a solution of tBuLi in pentane (60 mL, 1.83 m, 110 mmol, 1.07 eq) was added in drops. The dropping funnel was purged twice with 10 ml of pentane. The reaction mixture was slowly heated and stirred for 1 h at RT. 180 mL H₂O were added to the slightly yellow suspension, which decolorized the mixture. The aqueous phase was separated and the organic phase was washed once more with 180 mL H₂O. The organic phase was dried over Na₂SO₄, filtered, and the volatiles were removed in FV. The crude product was purified by distillation at 60 mbar and 70° C. The yield of the desired product in the form of a colorless, clear liquid was 32% (5.15 g, 32.7 mmol).

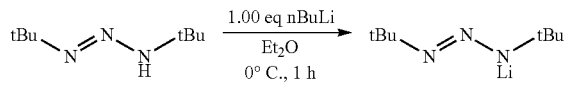

H(dbt) (700 mg, 4.45 mmol, 1.00 eq) was submitted in 10 mL Et₂O and cooled to 0° C. A solution of nBuLi in hexane (1.8 mL, 2.5 m, 4.45 mmol, 1.00 eq) was slowly added in drops. The slightly yellow solution was stirred for 1 h at RT, then brought to RT and stirred for a further 24 hours. The solvent of the clear solution was removed in FV to give a slightly yellow solid. The desired product was dried in FV and could be isolated with a yield of 95% (687 mg, 4.21 mmol).

2.2 Synthesis of Li(dbt)—Method 2 (Optimized Synthesis)

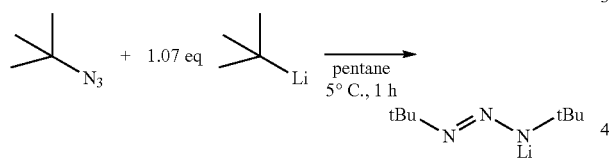

tBuN₃ (1.27 g, 12.8 mmol, 1.00 eq) was submitted in 10 mL pentane and cooled to 5° C. A solution of tBuLi in hexane (7.4 mL, 1.83 m, 13.7 mmol, 1.07 eq) was slowly added in drops, with a slight yellow coloration of the reaction mixture resulting from this. The reaction mixture was stirred at 5° C. for 1 h, then slowly warmed to RT and stirred for 1 hour. The slightly turbid solution was filtered through a syringe filter and the solvent of the slightly yellow filtrate was removed in FV. The desired product could be obtained with a yield of 83% (1.64 g, 10.0 mmol).

No differences between the two batches of Li(dbt) could be observed with the analytical examinations carried out. The optimized synthesis of Li(dbt) is a single-stage synthesis without by-products. While the neutral ligand was initially assumed, the optimization leads both to savings in reagents and in various working steps, etc. a distillation.

Example 3: Synthesis of K(dbt)

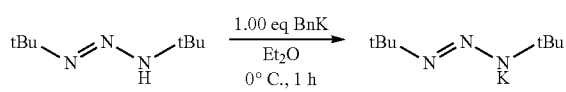

BnK (700 mg, 4.45 mmol, 1.00 eq) was taken up in 10 mL Et₂O and dropwise blended with H(dbt) (582 mg, 4.47 mmol, 1.00 eq) at 0° C. The colorless suspension was warmed to RT and stirred for 16 h. The slightly turbid solution was filtered, and the solvent of the colorless filtrate was completely removed at negative pressure. 85% (510 mg, 2.61 mmol) of the desired product could be obtained in the form of a colorless solid.

Example 4: Synthesis of Li(mbt)

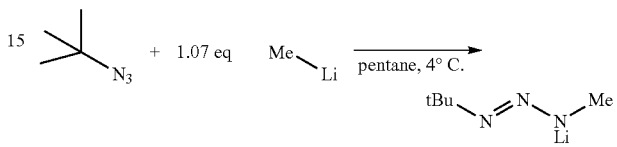

tBuN₃ (1.00 g, 10.7 mmol, 1.00 eq) was submitted in 15 mL pentane and cooled to 4° C. A solution of MeLi in Et₂O (6.8 mL, 1.60 m, 10.7 mmol, 1.07 eq) was slowly added to the reaction solution dropwise, which yielded a colorless solid. The reaction mixture was warmed to RT, the resulting colorless precipitate was filtered off and dried in an FV for several hours. The desired product was obtained as a colorless solid with a yield of 87% (1.13 g, 9.31 mmol). Upscaling of the reaction is possible.

Example 5: Synthesis of H(mbt)

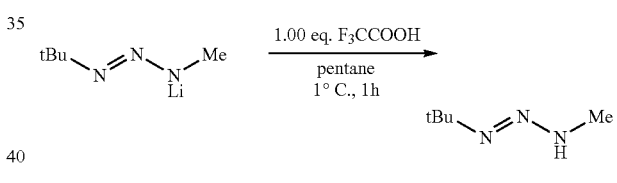

Li(mbt) (143 mg, 1.18 mmol, 1.00 eq) was placed in pentane and cooled to 0° C. While stirring, F₃CCOOH (135 mg, 1.18 mmol, 1.00 eq) was slowly added dropwise, with a slight foaming of the reaction solution being observed. The Li(mbt) used went into solution on warming the reaction mixture to RT, and the slightly turbid suspension was stirred for 16 h at RT. After the suspension was filtered through a syringe filter and the pentane removed in FV, the desired product could be obtained in the form of a colorless liquid.

Example 6: Synthesis of [Al(dbt)₂(Me)]

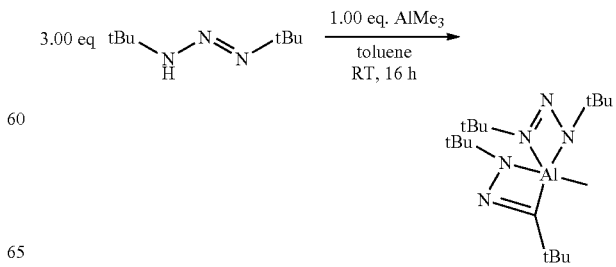

A toluene solution of AlMe$_3$ (33 mg, 0.46 mmol, 1.00 eq) was submitted and dropwise blended with H(dbt) (300 mg, 1.91 mmol, 3.00 eq) at RT. A gas evolution could be immediately observed. The colorless reaction mixture was stirred for 72 h at RT and filtered via syringe filter. The solvent of the filtrate was removed in FV to give a colorless oil. After repeated freeze-drying, the desired product was obtained in a yield of 87% (276 mg, 0.56 mmol) as a colorless solid (melting point: 46° C.).

Thermogravimetric Analysis of [Al(dbt)$_2$(Me)]

The crude product was analyzed by thermogravimetric analysis up to 700° C. at 10 K/min (FIG. 1). The thermogravimetric analysis shows a one-step process with an overall mass degradation of approximately 91.2%. A weight decrease of 3% of the starting material was observed at 127.2° C.

Example 7: Synthesis of [Ga(dbt)$_2$(H)]

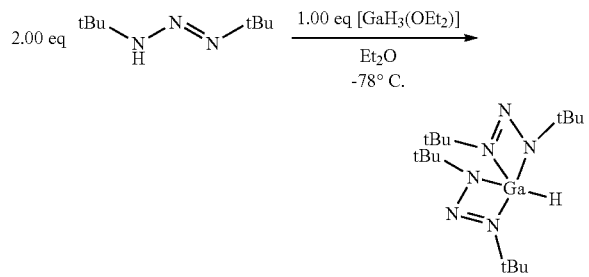

A solution of GaCl$_3$ (440 mg, 2.50 mmol, 1.00 eq) in 5 mL Et$_2$O cooled down to −78° C. was added dropwise to a suspension of LiH (260 mg, 32.8 mmol, 13.1 eq) in 5 mL Et$_2$O. A slightly gray precipitate immediately formed. The reaction mixture was stirred for 2 h at −78° C., then stirred for 16 h at RT. The slightly gray suspension was filtered into a pre-cooled flask. To the clear filtrate, a solution of GaCl$_3$ (176 mg, 1.00 mmol, 0.40 eq) in 5 mL Et$_2$O that was cooled down to −78° C. was added dropwise at −78° C. The suspension was heated to 0° C. while stirred and then filtered in a flask pre-cooled to −78° C. The clear filtrate was added dropwise at 0° C. to a solution of H(dbt) (786 mg, 5.00 mmol, 2.00 eq) in 5 mL Et$_2$O. Gas evolution was immediately observed. The suspension was slowly warmed to RT and stirred for 16 h. The mixture was filtered through a syringe filter and all volatiles were removed in FV. A colorless solid remained, which was taken up in 5 mL of hexane and filtered again through a syringe filter. The solvent of the filtrate was removed in FV to obtain the product with a yield of 53% (508 mg, 1.33 mmol, melting point: 46° C.). Single crystals for structural analysis could be obtained by sublimation in FV at 60° C.

The corresponding dihydrido gallium complex [Ga(dbt)H$_2$] could not be obtained by the 1:1 conversion of H(dbt) and [GaH$_3$(OEt$_2$)].

Thermogravimetric Analysis of [Ga(dbt)$_2$(H)]

Figure 2:
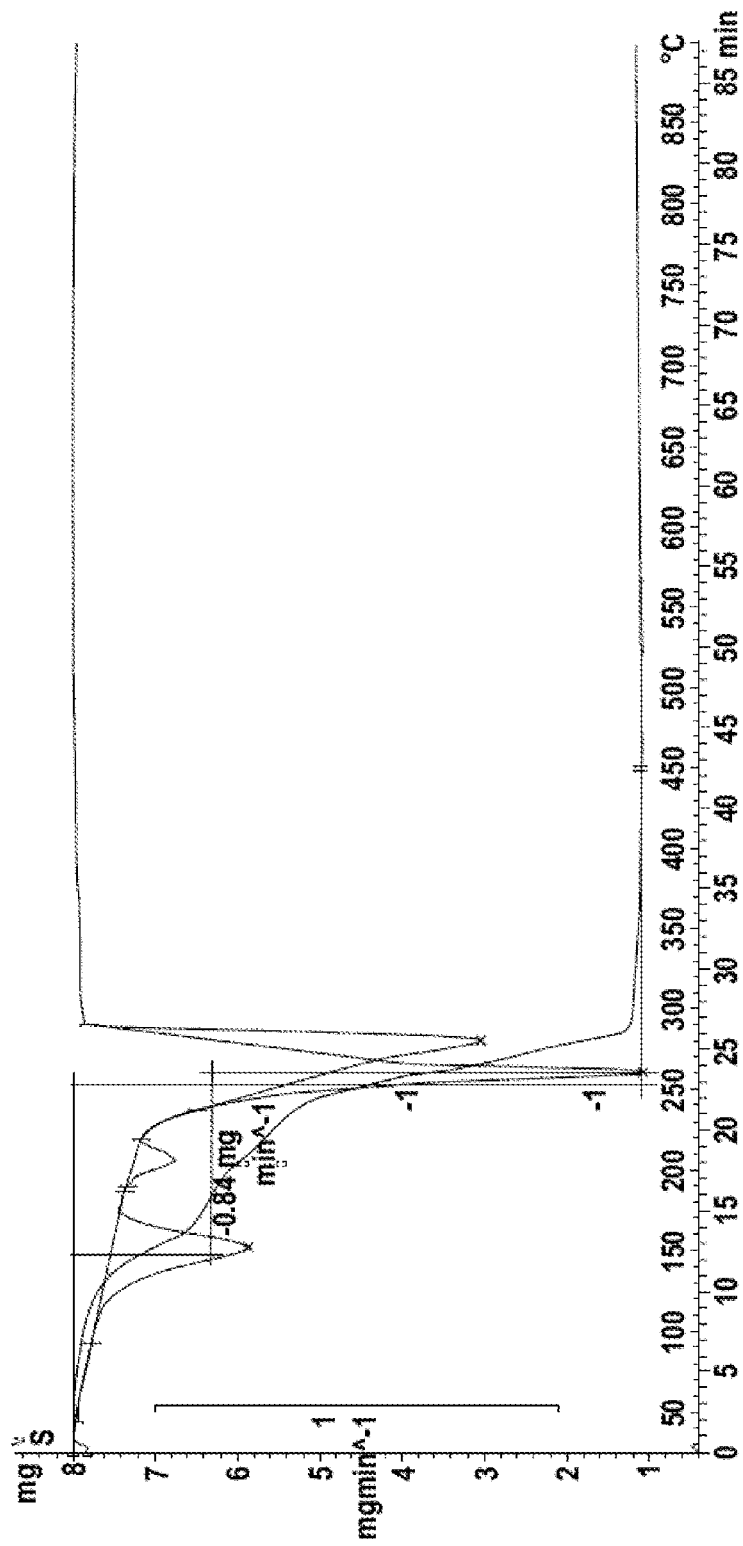

The crude product was examined through thermogravimetric analysis to 900° C. at 10 K/min (FIG. 2). A total of 86.6% of the starting material was converted into the gas phase.

Example 8: Synthesis of [In(dbt)Me$_2$]

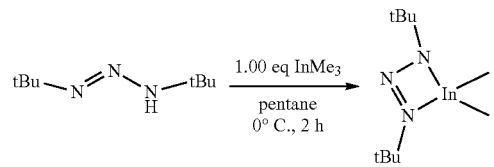

H(dbt) (250 mg, 1.59 mmol, 1.00 eq) was provided in 8 mL pentane and cooled to 0° C. A toluene solution of InMe$_3$ (254 mg, 1.59 mmol, 1.00 eq) was added dropwise to observe slight gas evolution. The reaction mixture was stirred for 1 h at 0° C. and for 16 h at RT. The solvent of the clear solution was removed in FV, allowing the desired product to be isolated as a colorless liquid. For purification, the product can be recondensed at 40° C. in a slight vacuum.

The reaction can also be carried out in an analogous manner in toluene, but this leads to difficulties in the isolation of the indium complex owing to the high volatility of the product.

Example 9: Synthesis of [In(dbt)$_3$]

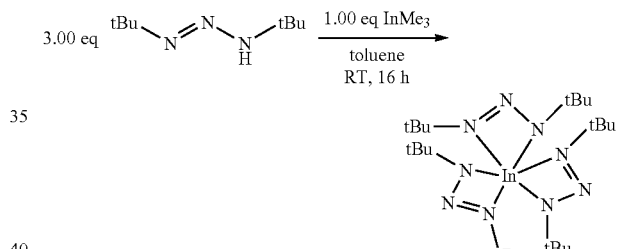

InMe$_3$ (150 mg, 0.94 mmol, 1.00 eq) was provided in 5 mL toluene, cooled to 0° C., and dropwise blended with H(dbt) (444 mg, 2.83 mmol, 3.00 eq). The reaction mixture was slowly warmed to RT and stirred for 16 h. The solvent of the clear solution was removed in FV. The desired product was obtained in the form of a colorless solid with a yield of 73% (403 mg, 0.69 mmol) and can be sublimated in FV at 80° C.

Thermogravimetric Analysis of [In(dbt)$_3$]

Figure 3:
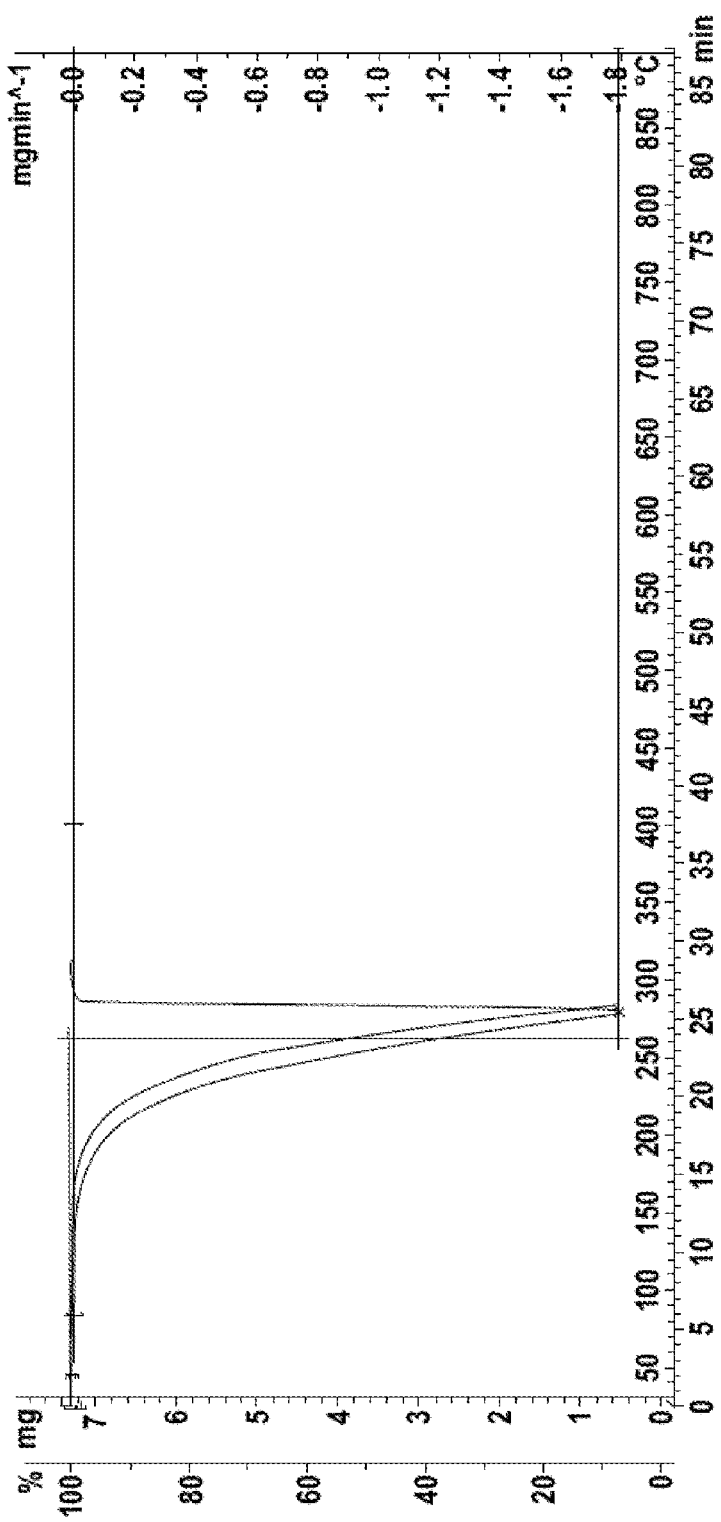

The crude product was examined through thermogravimetric analysis to 900° C. at 10 K/min (FIG. 3). The analysis shows a one-step process with an overall mass degradation of about 92.8%. A weight decrease of 3% of the starting material was observed at 196.7° C.

Example 10: Synthesis of [La(dbt)$_3$]

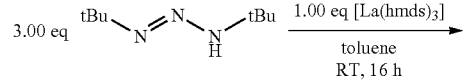

-continued

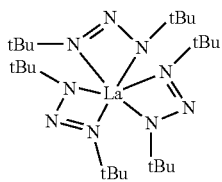

[La(hmds)₃] (225 mg, 0.36 mmol, 1.00 eq) was provided in 10 mL toluene and cooled to 0° C. H(dbt) (171 mg, 1.09 mmol, 3.00 eq) was dropwise added to the colorless solution. The clear, colorless reaction mixture was warmed to RT and stirred for 16 h. With the aid of a ¹H NMR reaction control, it was confirmed that no [La(hmds)₃] was present in the reaction mixture anymore. All volatile components of the reaction solution were removed in FV and the resulting colorless solid was dried at 60° C. in FV. The desired product was obtained in a 72% (158 mg, 0.26 mmol) yield.

Thermogravimetric Analysis of [La(dbt)₃]

Figure 4:
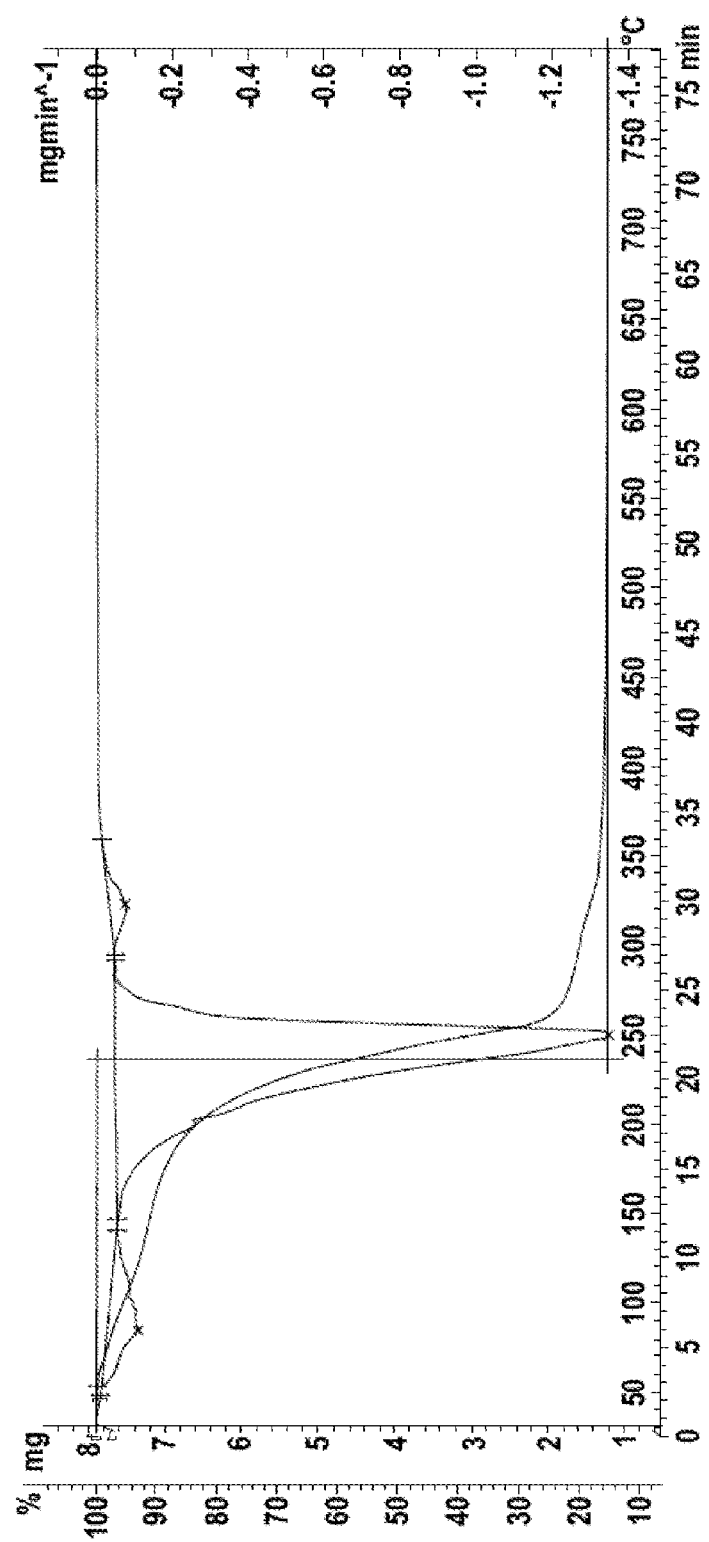
Figure 5:
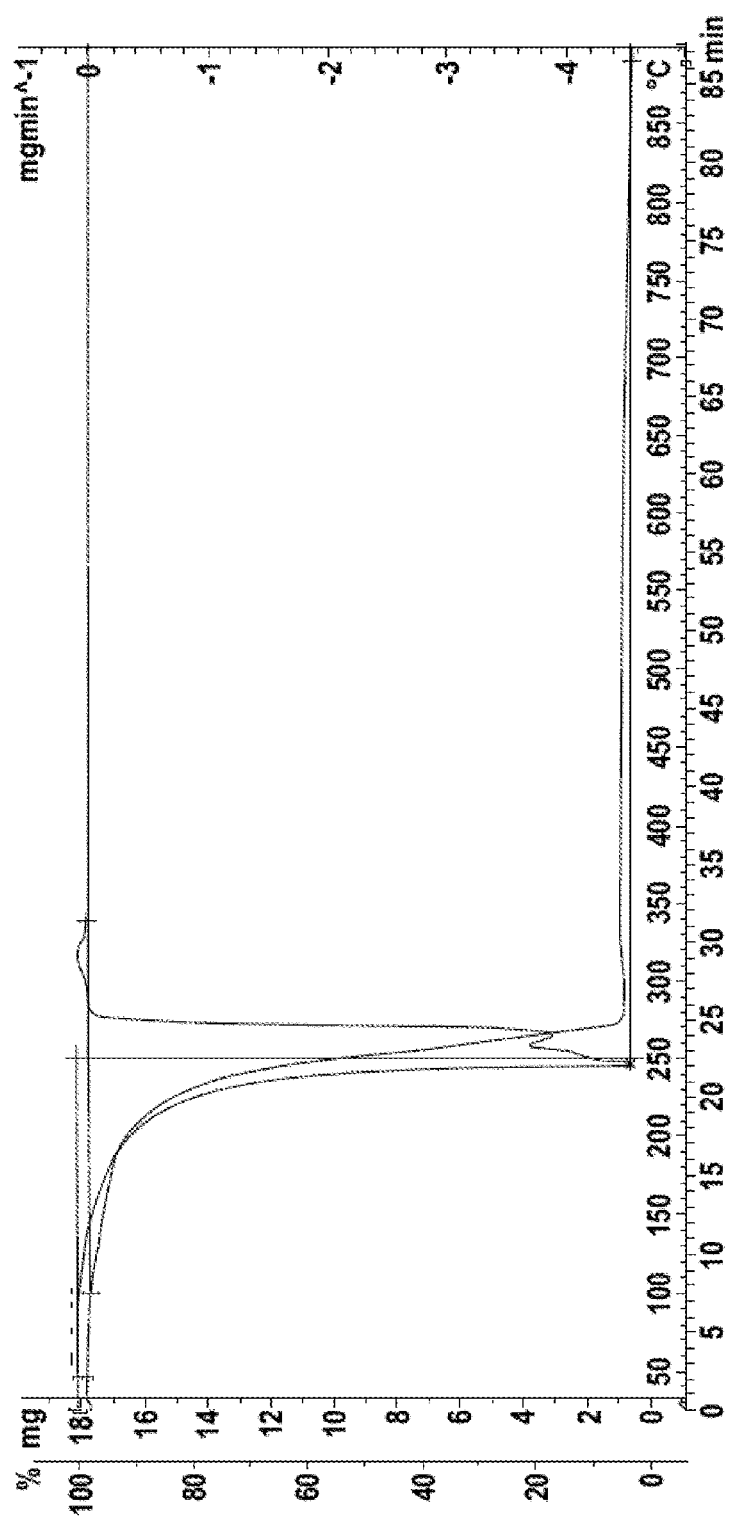
Figure 6:
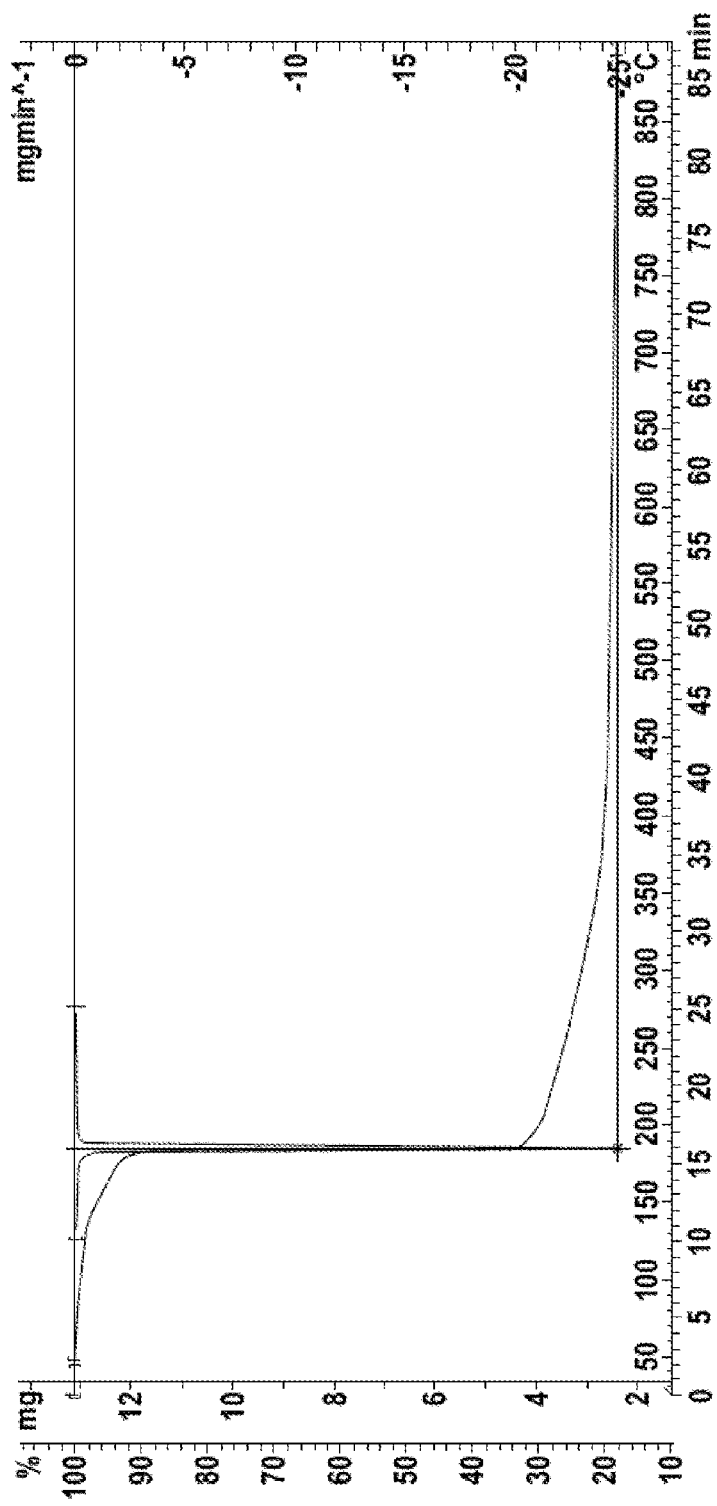
Figure 7:
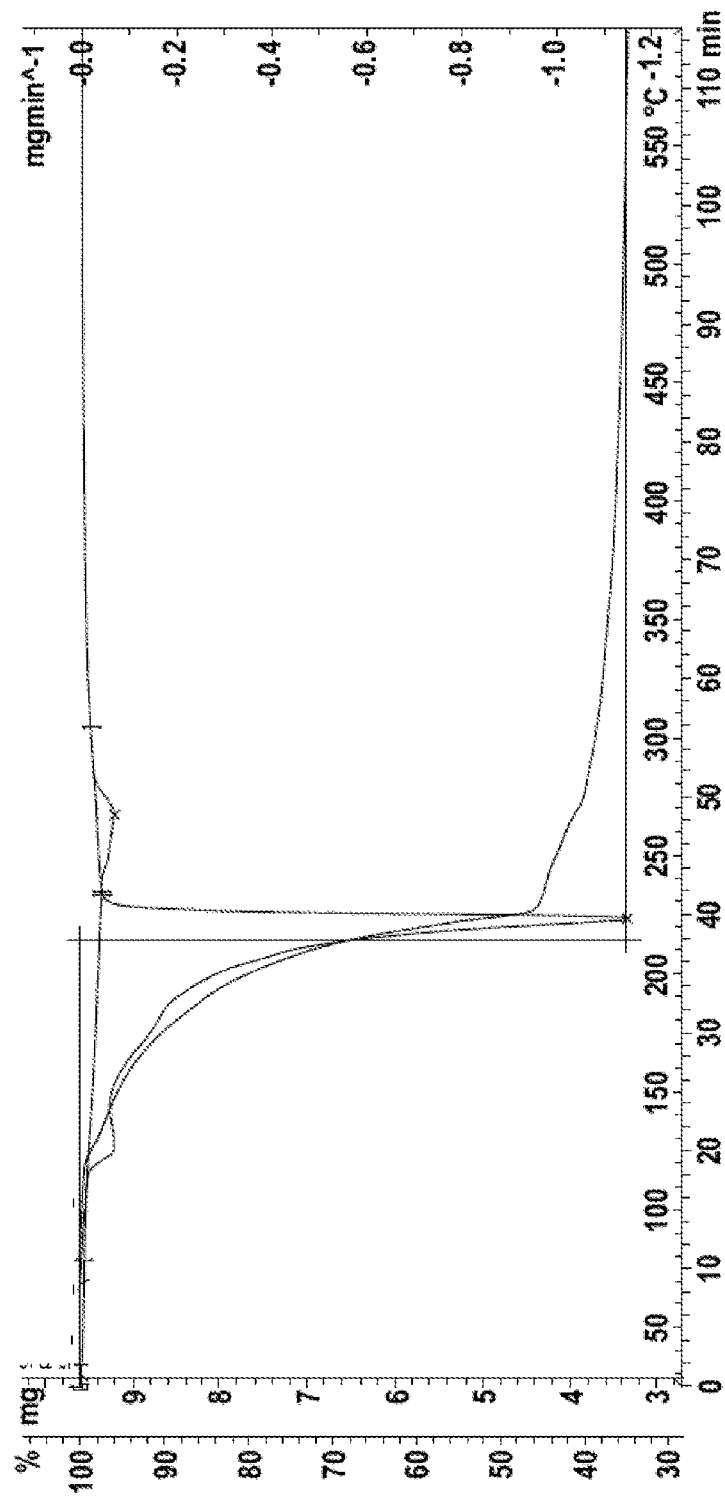

The crude product was examined through thermogravimetric analysis to 800° C. at 10 K/min (FIG. 4). The thermogravimetric analysis shows a one-step process with an overall mass degradation of approximately 85%. A weight decrease of 3% of the starting material was observed at 85° C. In the range up to 100° C., it can be seen that residual traces of Hhmds are still present in the product. Starting from a temperature of 103° C., an initial melting process of the lanthanum complex occurs, wherein the maximum mass reduction is achieved at a temperature of 250° C. No significant mass degradation can be observed any more from a temperature of about 400° C.

Example 11: Synthesis of [Co(dbt)₂]

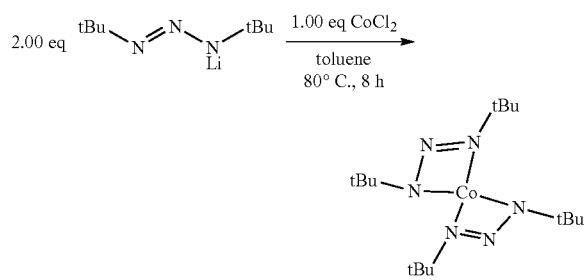

Li(dbt) (654 mg, 4.00 mmol, 2.00 eq) was provided with CoCl₂ (260 mg, 2.00 mmol, 1.00 eq) and blended with 15 mL toluene. The reaction mixture was heated at 80° C. for 8 h, during which time a color change from blue to dark red was observed. The solvent of the cooled reaction mixture was removed in FV and the desired product was directly sublimated from the residue in FV at 100° C. [Co(dbt)₂] was obtained as a dark red, almost black solid with a yield of 53% (394 mg, 1.06 mmol).

Thermogravimetric Analysis and Residue Determination of [Co(dbt)₂]

In the TGA curve to 900° C. at 10 K/min (FIG. 5), a one-stage mass loss can be observed, in which the maximum mass degradation per time can be observed at a temperature of 248° C. At a temperature of 156° C., the sample degraded to 3%. Starting at a temperature of 91° C., an endothermic, very broad peak can be observed, which can be assigned to an irregular melting process. The total mass loss is 97%, the residue obtained being examined in more detail by means of XRPD. It was found that the residue is elemental cobalt.

Example 12: Synthesis of [Co₂(mbt)₄]

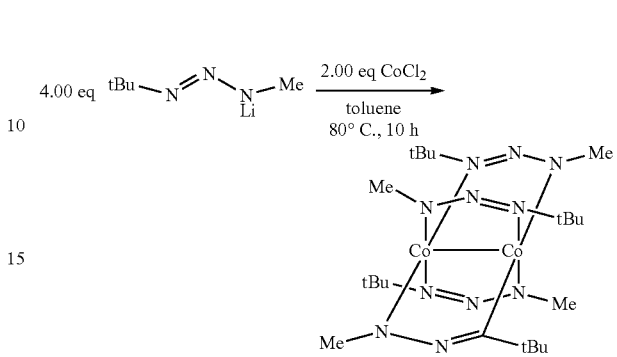

Li(mbt) (193 mg, 1.59 mmol, 4.00 eq) and CoCl₂ (103 mg, 0.79 mmol, 2.00 eq) were provided together and blended with 10 mL toluene at 0° C. Upon thawing of the reaction mixture, a color change from blue to dark brown could be observed. The reaction mixture was heated at 80° C. for 10 h and the solvent was removed in FV at RT. The desired product was sublimated from the dark brown residue in a dynamic vacuum at 85° C. The dinuclear cobalt complex was obtained as a red-brown solid with a yield of 51% (116 mg, 0.20 mmol). Single crystals for crystal structure analysis could be obtained by light vacuum sublimation at 100° C. Due to spin-pairing of the two cobalt cores in [Co₂(mbt)₄], this, in contrast to [Co(dbt)₂], shows diamagnetic behavior.

Thermogravimetric Analysis and Residue Determination of [Co₂(Mbt)₄]

The TGA curve to 900° C. at 10 K/min (FIG. 6) of the cobalt complex shows a one-stage course, wherein the maximum mass degradation per time can be observed at a temperature of 189° C. The 3% degradation was determined at a temperature of 147° C. Starting at a temperature of 184° C., an initial exothermic process can be detected, which leads to maximum mass degradation per time and can be assigned to a decomposition process. The total mass degradation was 82%, the residue obtained from this measurement being analyzed by means of XRPD. This could be identified as elemental cobalt.

Example 13: Synthesis of [Ru(dbt)(Cl)(p-Cymene)]

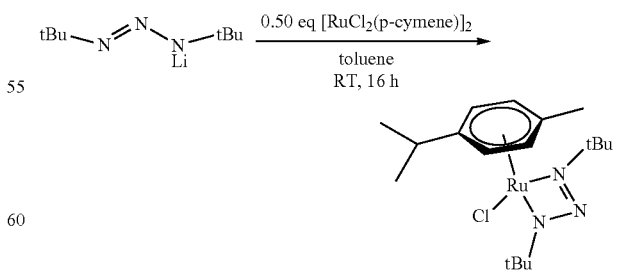

Li(dbt) (248 mg, 1.52 mmol, 1.00 eq) was provided in 5 mL toluene. The ruthenium precursor (465 mg, 0.76 mmol, 0.50 eq) was added portionwise and rinsed with 4 mL of toluene. After a short time, a color change from dark red to black was observed. The reaction mixture was stirred overnight at RT and filtered via syringe filter. The solvent of the yellow-black filtrate was removed in FV. The desired product was obtained in the form of a dark green solid with a yield of 51% (331 mg, 0.77 mmol, melting point: 66.5° C.).

Thermogravimetric Analysis of [Ru(dbt)(Cl)(p-Cymene)]

The TGA curve to 600° C. at 5 K/min (FIG. 7) shows a one-stage course with a maximum mass loss per time at 235° C. While the 3% degradation is at a temperature of 153° C., the total mass degradation is 67%. At a temperature of 67° C., a melting process starts, which proceeds almost continuously into a sublimation process. From a temperature of 200° C., a further exothermic peak can be observed on the basis of the SDTA curve, which can be assigned to the decomposition process (not shown). From a temperature of about 400° C., the mass degradation no longer changes significantly. The residue obtained in the measurement was examined in more detail by means of XRPD and elemental ruthenium could be confirmed.

Example 14: Synthesis of [Ru(dbt)(H)(p-Cymene)]

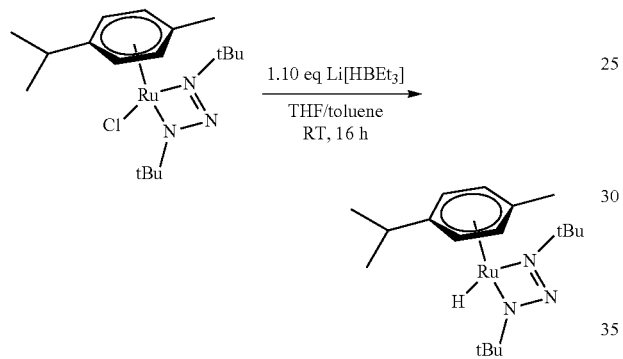

[Ru(dbt)(Cl)(p-cymene)] (227 mg, 0.51 mmol, 1.00 eq) was provided in 5 mL toluene. At 0° C., a solution of Li[HBEt$_3$] in THF (0.56 mL, 1 m, 0.56 mmol, 1.10 eq) was provided. The reaction mixture was slowly warmed to RT and stirred for 16 h. Precipitation of a colorless solid could be observed. The precipitated solid was separated by filtration and the solvent of the filtrate was removed in FV. The desired product could be obtained after repeated freeze drying in the form of a green-black viscous liquid. For purification, the ruthenium hydrido complex was recondensed in FV at 95° C.

Alternatively, the synthesis can also be carried out with LiAlH$_4$ (0.25 equivalents). By contrast, the methyl-substituted complex, which can be represented by the conversion of [Ru(dbt)(Cl)(p-cymene)] and methyllithium, is present as a solid.

Thermogravimetric Analysis of [Ru(dbt)(H)(p-Cymene)]

Figure 8:
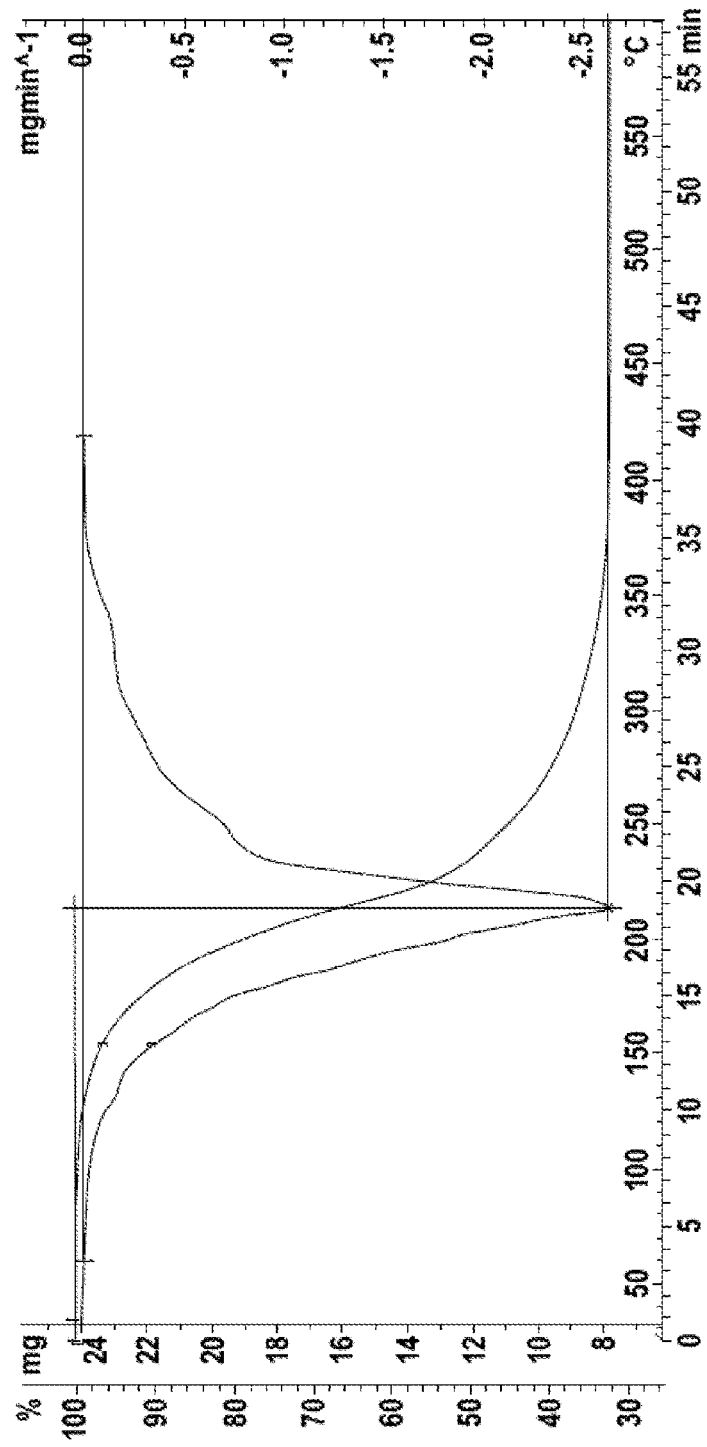
Figure 9:
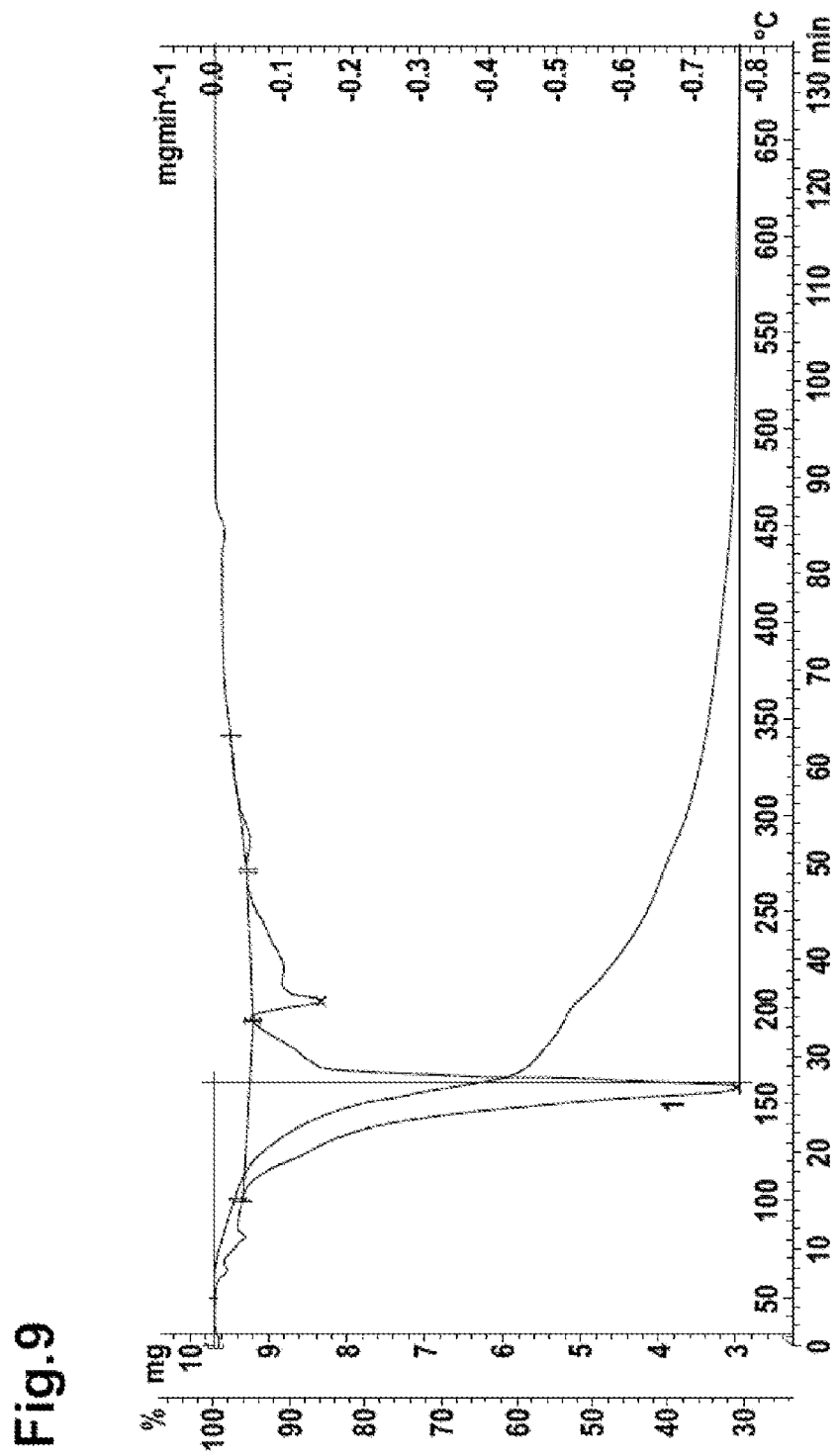

The crude product was examined through thermogravimetric analysis to 600° C. at 10 K/min (FIG. 8). The analysis shows a one-step process with an overall mass degradation of about 67.8%. A weight decrease of 3% of the starting material was observed at 150.5° C.

Example 15: Synthesis of [Ru(mbt)(Cl)(p-Cymene)]

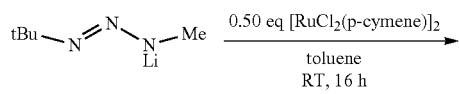

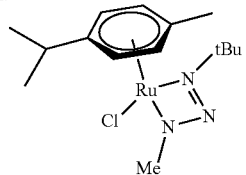

Li(mbt) (221 mg, 1.82 mmol, 1.00 eq) was provided in 10 mL toluene and portionwise blended with [RuCl$_2$(p-cymene)]2 (559 mg, 0.91 mmol, 0.50 eq) at 0° C. Upon slow thawing of the mixture to RT, a color change from brown to dark green could be observed. The reaction mixture was stirred for 16 h at RT and was filtered via a syringe filter. The solvent of the reddish filtrate was removed in FV and the remaining solid was freeze-dried several times. The desired product was obtained in the form of a dark red solid with a yield of 59% (414 mg, 1.07 mmol, melting point: 51.9° C.).

Thermogravimetric Analysis of [Ru(mbt)(Cl)(p-Cymene)]

The measured TGA/SDTA curve to 700° C. at 5 K/min (FIG. 9) shows a one-step mass degradation with a maximum degradation at a temperature of 169° C. Above this temperature, the mass loss per time decreases again, which can be observed in itself on the basis of a positive slope from the minimum. The 3% degradation of the ruthenium complex is at 118° C. Starting at a temperature of 52° C., an initial melting process can be observed, which proceeds continuously into a sublimation process. The total mass loss is at 64%. The residue obtained from this measurement was assayed by XRPD analysis and could be identified as elemental ruthenium.

Example 16: Synthesis of [Ru(mbt)(H)(p-Cymene)]

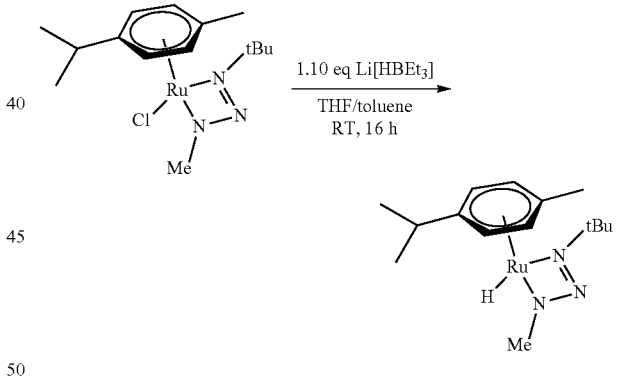

[Ru(mbt)(Cl)(p-cymene)] (196 mg, 0.49 mmol, 1.00 eq) was dissolved in 5 mL toluene and blended with a solution of Li[HBEt$_3$] in THF (0.54 mL, 1 m, 0.54 mmol, 1.10 eq) at 0° C. The reaction mixture was warmed slowly to RT and stirred for 16 h, wherein a colorless solid precipitated. This was separated and the solvent of the filtrate was removed in FV. The desired product could be obtained after repeated freeze drying in the form of a black viscous liquid.

$^1$H-NMR (C$_6$D$_6$, 300 MHz, 300 K): δ/ppm=−2.93 (s, 1H, RuH), 1.21 (d, $^3J_{HH}$=6.6 Hz, 6H, CHMe$_2$), 1.31 (s, 9H, CMe$_3$), 2.00 (s, 3H, C$_{arom}$.Me), 2.49 (sept, $^3J_{HH}$=6.6 Hz, 1H, CHMe$_2$), 3.40 (s, 3H, NMe), 4.72 (d, 3J$_{HH}$=4.6 Hz, 2H, CH$_{arom}$), 4.91 (d, $^3J_{HH}$=4.6 Hz, 2H, CH$_{arom}$.).

IR: ṽ/cm$^{-1}$=2958 (m), 2920 (m), 2864 (m), 1884 (w), 1457 (w), 1382 (w), 1356 (m), 1290 (w), 1260 (st), 1216 (w), 1193 (w), 1086 (st), 1021 (st), 913 (w), 799 (vst), 661 (w), 631 (w), 552 (w).

TGA: ($T_S$=25° C., $T_E$=600° C., 10° C./min), stages: 2

3% degradation: 108.2° C., max. degradation (1st stage): 181.3° C., max. degradation (2nd stage): 436.1° C., Mass degradation (1st stage): 58.0%, Total mass degradation: 64.8%.

SDTA: $T_{D1(Onset)}$: 97.3° C., TD1(max.): 127.8° C., $T_{D2(onset)}$: 162.1° C., $T_{D2(max)}$: 169.8° C., $T_{D3\ (Onset)}$: 183.8° C., $T_{D3(max)}$: 192.1° C.

Figure 14:
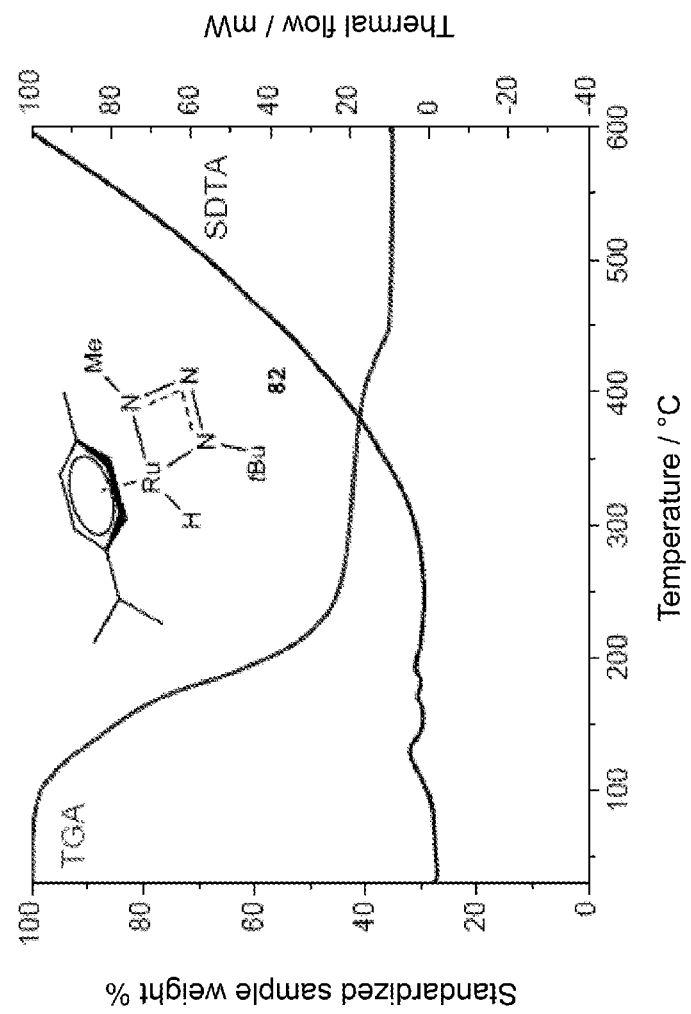

FIG. 14 shows a graphical representation of the TGA and SDTA measurements.

Example 17: Synthesis of [Ru(mbt)(Cp*)(CO)]

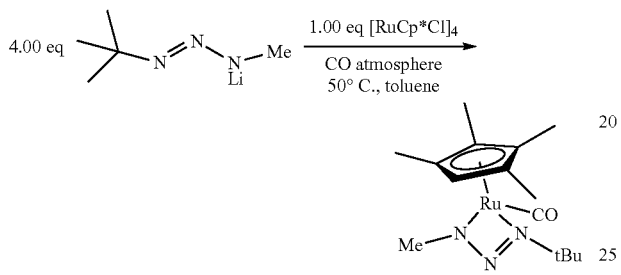

[RuCp*Cl]$_4$ (90 mg, 0.45 mmol, 1.00 eq) and Li(mbt) (216 mg, 1.79 mmol, 4.00 eq) were provided together and taken up in 25 mL toluene. The dark brown solution was heated to 50° C. for 1 h, then cooled to RT. For 1 h, CO was passed through the reaction mixture at RT. The dark red black reaction solution was filtered over Celite®. The solvent was removed in FV, leaving a dark red, almost black, honey-like solid which could be identified as the desired product.

Thermogravimetric Analysis of the Crude Product [Ru(mbt)(Cp*)(CO)]

Figure 10:
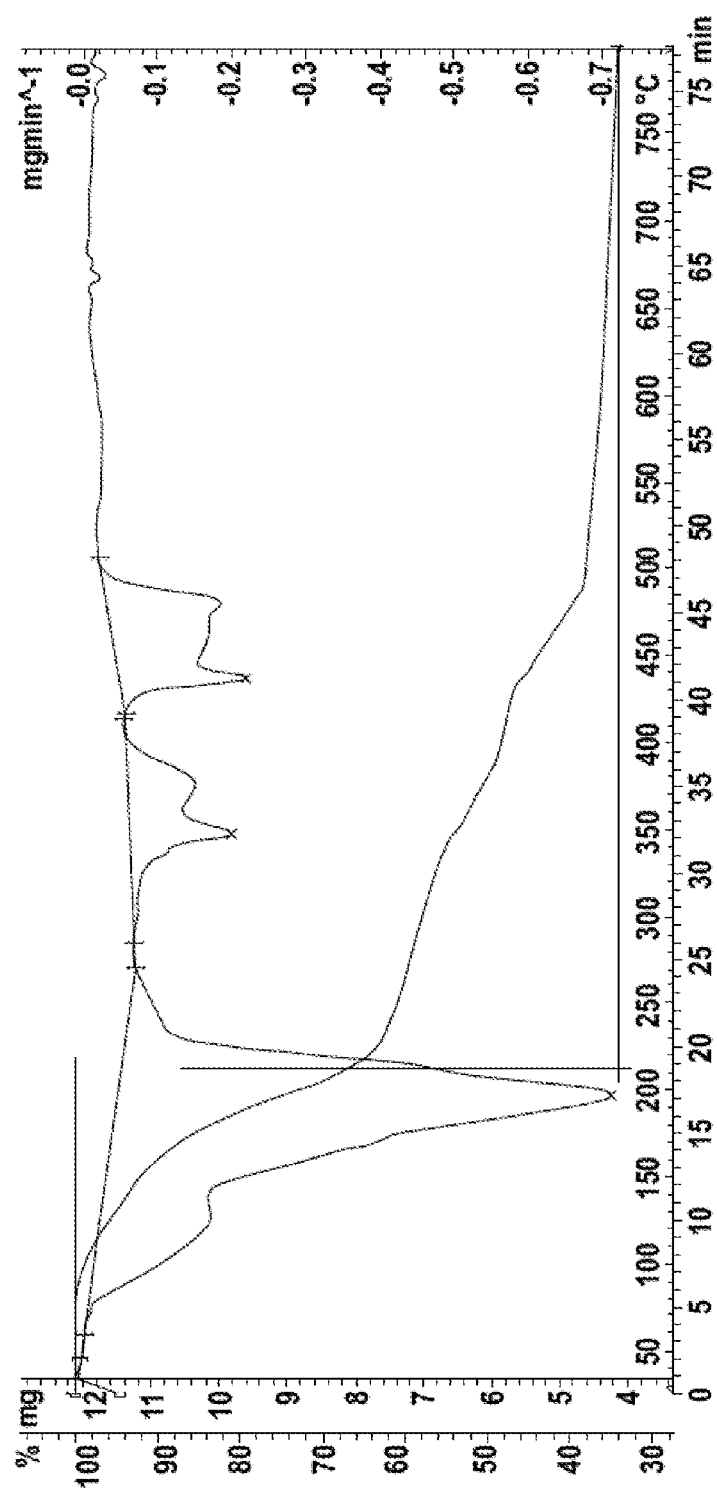
Figure 11:
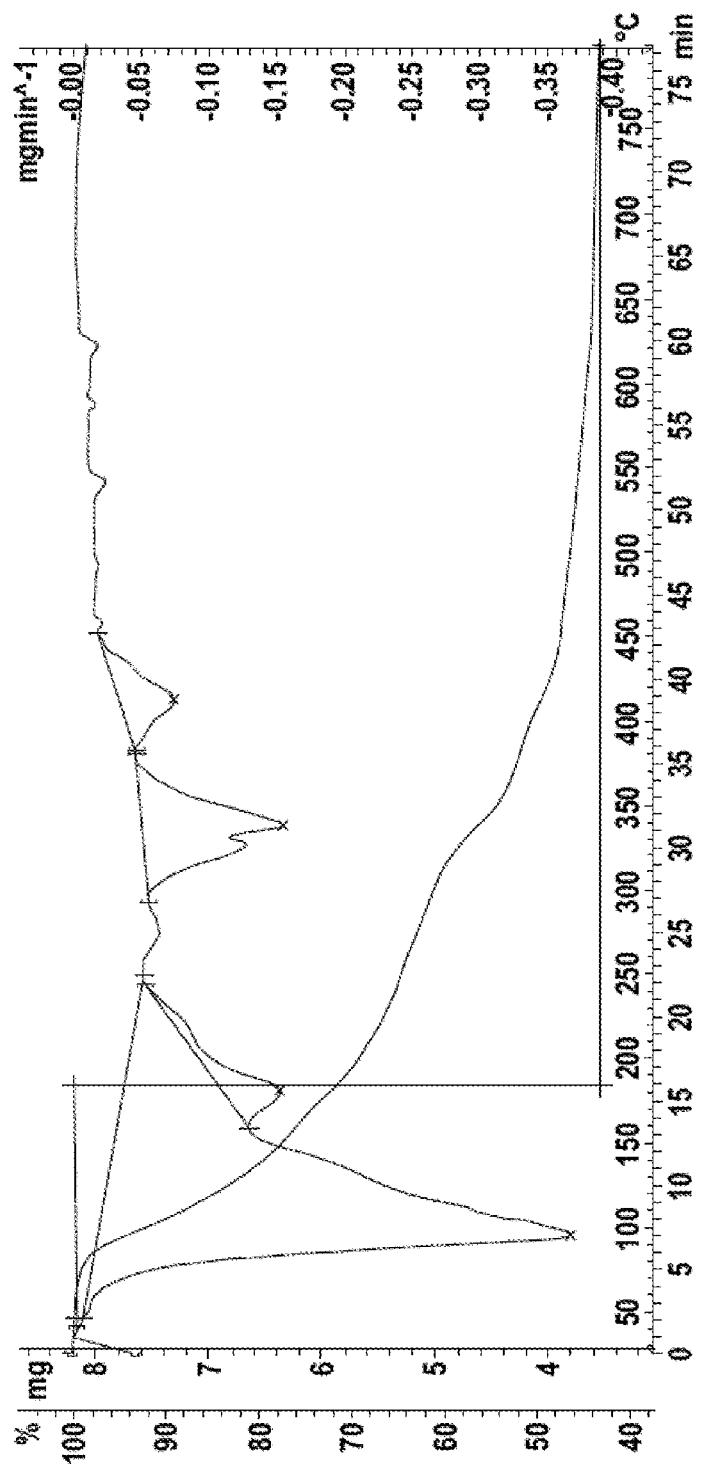
Figure 12:
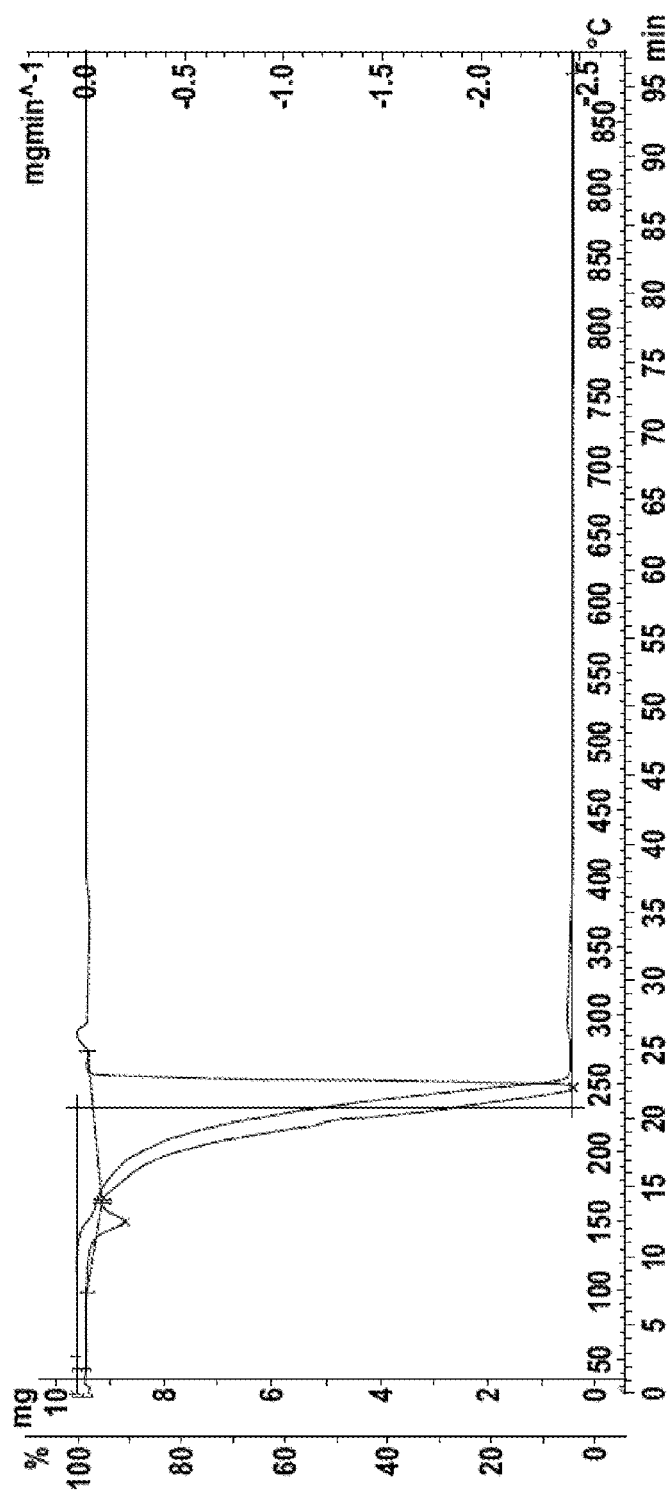
Figure 13:
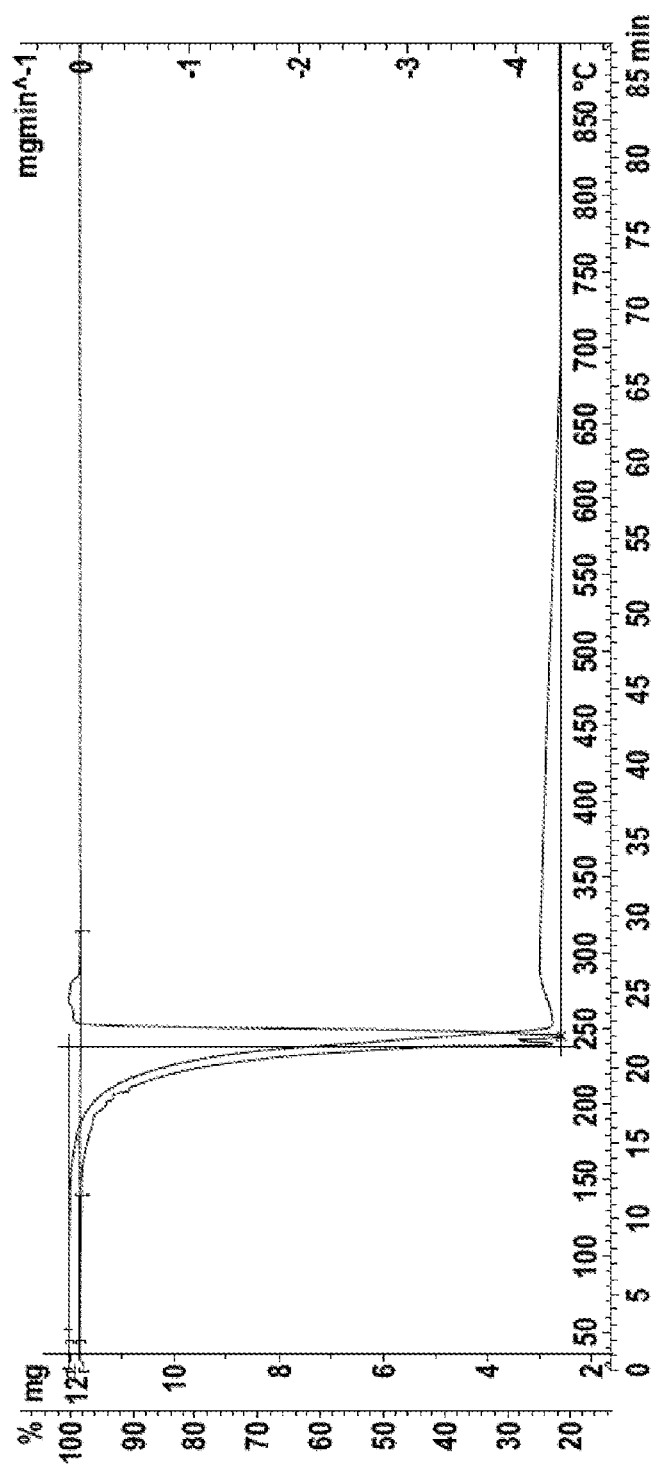

The crude product was analyzed to 800° C. at 10 K/min by thermogravimetric analysis (FIG. 10). In this case, a stepwise degradation can be observed, with a total mass degradation of 67%. The decomposition begins at a temperature of about 75° C. with an endothermic peak. A weight decrease of 3% of the starting material was observed at 116.0° C. The residue obtained from this measurement was analyzed by XRPD and could be identified as elemental ruthenium.

Example 18: Synthesis of [Ru(mbt)(Cp*)]

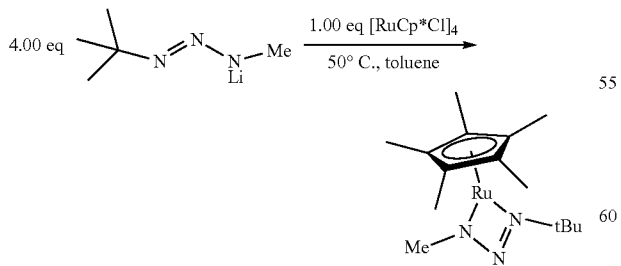

[RuCp*Cl]$_4$ (100 mg, 0.50 mmol, 1.00 eq) and Li(mbt) (244 mg, 1.98 mmol, 4.00 eq) were provided together and taken up in 10 mL toluene. The dark brown suspension was heated to 50° C. for 2 h and was cooled to RT. The dark red-black reaction mixture was filtered over Celite® and the solvent of the filtrate was removed in FV to isolate a dark green, almost black, honey-like solid.

Thermogravimetric Analysis of the Crude Product [Ru(Mbt)(Cp*)]

The crude product was examined through thermogravimetric analysis to 800° C. at 10 K/min (FIG. 11), wherein a stepwise degradation can be observed. The total mass loss is at 57%. The decomposition begins at a temperature of about 79° C. with an endothermic peak. A weight decrease of 3% of the starting material was observed at 87.6° C. The residue obtained from this measurement was analyzed by XRPD and could be identified as elemental ruthenium.

Example 19: Synthesis of [Cu$_2$(dbt)$_2$]

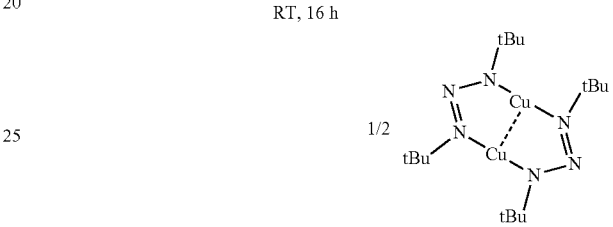

Li(dbt) (280 mg, 1.72 mmol, 1.00 eq) was provided together with CuCl (170 mg, 1.72 mmol, 1.00 eq) and blended with 10 mL pre-cooled toluene. The reaction mixture was stirred for 16 h at RT, whereupon a color change from yellow to brown was observed. The suspension was filtered over Celite® and the solvent of the filtrate removed in FV. The crude product was purified by sublimation in a dynamic vacuum at 70° C. and could be obtained in a yield of 71% (268 mg, 0.61 mmol) as a yellow solid. Single crystals for crystal structure analysis were obtained from a saturated solution of n-hexane at −21° C.

Thermogravimetric Analysis

The crude product was examined through thermogravimetric analysis to 1000° C. at 10 K/min (FIG. 12). [Cu$_2$(dbt)$_2$] shows a one-stage mass loss, wherein the 3% degradation is at 156° C. The total mass loss is 96%, which is attributable to the good sublimatability of the copper compound. From a temperature of about 260° C. onwards, no significant mass degradation is observed any longer. Elemental copper in the crucible was observed as residue.

Example 20: Synthesis of [Cu$_4$(mbt)$_4$]

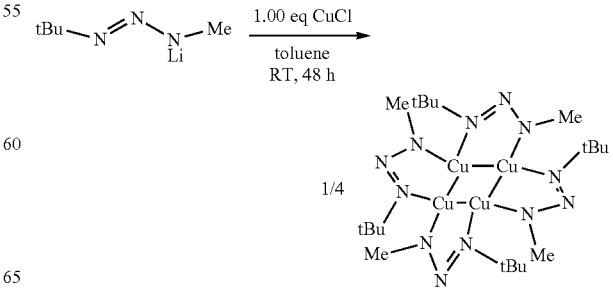

Li(mbt) (208 mg, 1.72 mmol, 1.00 eq) and CuCl (170 mg, 1.72 mmol, 1.00 eq) were provided and blended with 10 mL pre-cooled toluene. The colorless reaction mixture was stirred for 48 h at RT, whereby a color change to bright yellow could be observed. The suspension was filtered over Celite® and the solvent of the filtrate was removed in FV. The bright yellow crude product was purified by sublimation under dynamic vacuum at 65° C. to 75° C. and could be obtained in a yield of 82% (248 mg, 0.35 mmol). Single crystals for crystal structure analysis could be obtained from a saturated solution of n-hexane at RT.

Thermogravimetric Analysis

The crude product was examined through thermogravimetric analysis to 900° C. at 10 K/min (FIG. 13). [Cu$_4$(mbt)$_4$] shows a one-stage degradation with a total mass loss of 79%. The 3% degradation is at 198° C., while the maximum mass degradation was determined to be at approximately 250° C. No significant mass loss can be observed any more from a temperature of about 255° C. The SDTA curve shows various melting or phase conversion processes until the decomposition begins, starting at a temperature of 236° C. (not shown). The residue from the thermal gravimetric analysis was examined by XRPD and could be identified as elemental copper.

Example 21: Synthesis of [Ca(dbt)$_2$]

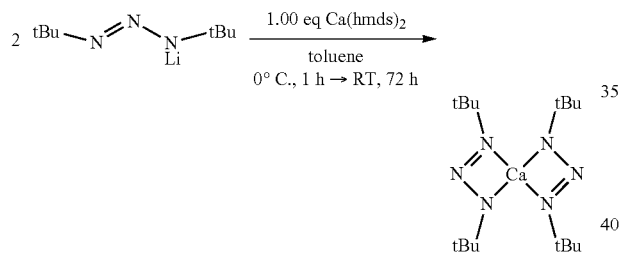

Ca(hmds)$_2$ (122 mg, 0.338 mmol, 1.00 eq) was provided in 10 mL toluene and cooled to 0° C. Dropwise, Hdbt (106 mg, 0.684 mmol, 2.00 eq) was added. The colorless reaction mixture was stirred for 72 h at RT, then filtered off, and the filtrate was evaporated to dryness. The product was obtained as a light-yellow solid with a yield of 63% (116 mg, 0.22 mmol).

$^1$H-NMR (C$_6$D$_6$, 300 MHz, 300 K): δ/ppm=1.38 (s, CMe$_3$).

$^{13}$C-NMR (C$_6$D$_6$, 75 MHz, 300 K): δ/ppm=31.1 (CMe$_3$), 56.2 (CMe$_3$).

IR: $\tilde{v}$/cm$^{-1}$=2958 (m), 2860 (w), 1601 (w), 1473 (w), 1459 (w), 1384 (w), 1356 (m), 1295 (st), 1243 (m), 1194 (st), 1026 (w), 989 (w), 806 (w), 748 (w), 614 (st), 472 (st).

TGA: (T$_S$=25° C., T$_E$=800° C., 10° C./min), stages: 1

3% degradation: 115.3° C., max. degradation: 309.0° C., total mass degradation: 79.3%.

SDTA: T$_{D(Onset)}$: 194.4° C., T$_{D(max.)}$: 263.7° C.

RPD: Residue from TGA analysis: 2θ$_{Lit.}$$^{[62]}$(2θ$_{obs.}$) for Ca$_3$N$_2$: 32.779 (32.785), 35.598 (35.545), 36.191 (36.175), 37.279 (37.375), 38.611 (38.455), 44.599 (44.755), 50.979 (50.665), 60.458 (60.415), 66.228 (66.265).

Example 22: Synthesis of [Si(dbt)$_4$]

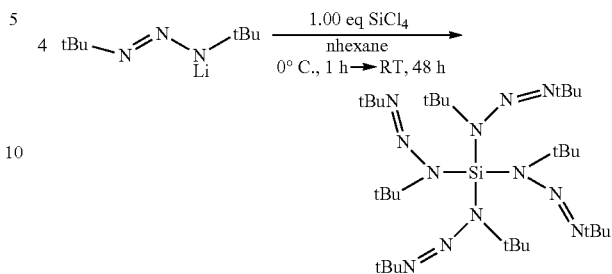

$^1$H-NMR (C$_6$D$_6$, 300 MHz, 300 K): δ/ppm=1.30 (s, CMe$_3$).

$^{13}$C-NMR (C$_6$D$_6$, 75 MHz, 300 K): δ/ppm=30.7 (CMe$_3$), 56.7 (CMe$_3$).

IR: $\tilde{v}$/cm$^{-1}$=2957 (m), 2862 (w), 2000 (w), 1669 (w), 1473 (w), 1381 (w), 1355 (m), 1334 (m), 1282 (m), 1244 (m), 1170 (st), 1027 (w), 957 (m), 826 (w), 787 (w), 752 (w), 620 (m), 564 (m), 473 (m), 424 (m).

Elemental analysis: for C$_{32}$H$_{72}$N$_{12}$Si calculated: C: 58.85%, H: 11.11%, N: 25.74%.

found: C: 58.66%, H: 10.95%, N: 24.04%.

TGA: (T$_S$=25° C., T$_E$=900° C., 10° C./min), stages: 1

3% degradation: 184.3° C, max. degradation: 261.3° C., total mass degradation: 96.0%.

SDTA: T$_{D1(Onset)}$: 237.2° C., T$_{D1(max)}$: 263.6° C.

Figure 15:
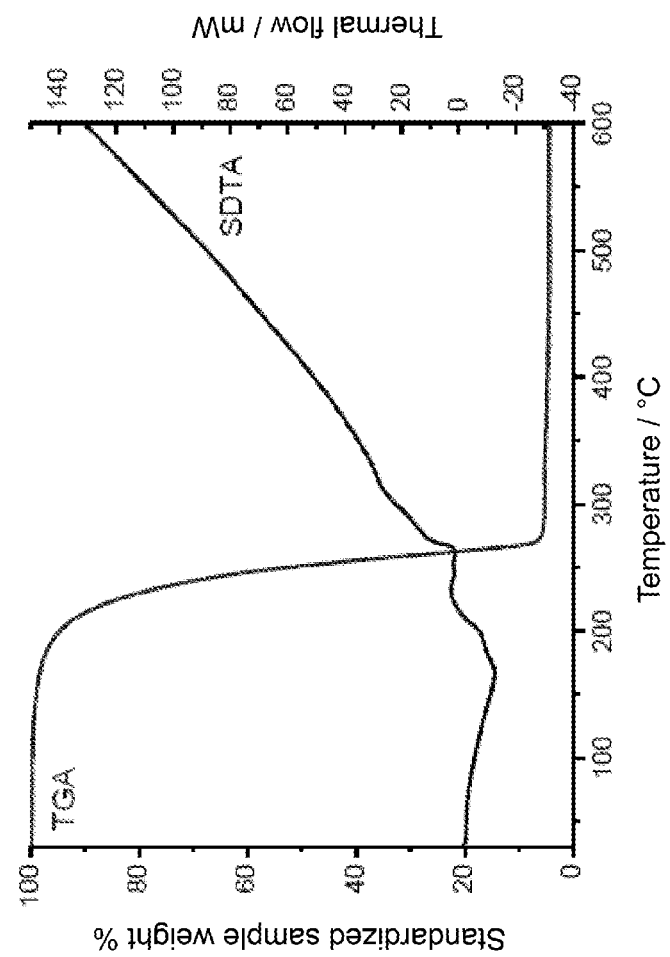

FIG. 15 shows a graphical representation of the TGA and SDTA measurements. μRFA: 97.6 wt-% Si.

Example 23: Synthesis of [Sb(dbt)$_3$]

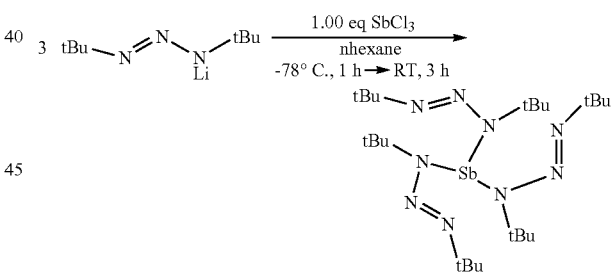

SbCl$_3$ (92 mg, 0.403 mmol, 1.00 eq) was provided in 5 mL n hexane and cooled to −78° C. A pre-cooled solution of [Li(dbt)] (197 mg, 1.21 mmol, 3.03 eq) in 5 mL nhexane was slowly added dropwise, wherein the suspension changed color to dark gray. The reaction mixture was stirred for 1 h at −78° C. and then stirred for 3 h at RT. The dark gray suspension was filtered and the filtrate was evaporated to dryness in FV. The crude product was purified sublimatively in FV at 90° C. The product was isolated as a dark yellow solid with a yield of 43% (100 mg, 0.17 mmol).

HR-EI-MS: calculated for Cl$_6$H$_{36}$N$_6$: 433.2040 m/z, found: 433.2037 m/z.

Melting point: 132° C. (visual, 5° C./min).

1H-NMR (C$_6$D$_6$, 300 MHz, 300 K): δ/ppm=1.39 (s, CMe$_3$).

13C-NMR (C$_6$D$_6$, 75 MHz, 300 K): δ/ppm=30.6 (CMe$_3$), 60.9 (CMe$_3$).

IR: ṽ/cm-1=2965 (st), 2927 (m), 2866 (w), 1471 (w), 1456 (w), 1413 (m), 1385 (w), 1357 (st), 1257 (m), 1221 (m), 1201 (st), 1144 (vst), 1017 (m), 930 (w), 884 (w), 802 (w), 757 (w), 618 (st), 562 (w), 499 (m), 473 (w), 431 (w).
Elemental Analysis: for $C_{24}H_{54}SbN_9$
calculated: C: 48.82%, H: 9.22%, N: 21.35%; found: C: 47.95%, H: 9.11%, N: 19.23%.

TGA: ($T_S$=25° C., $T_E$=700° C., 10° C./min), stages: 1 3% degradation: 150.6° C., max. degradation: 211.1° C., total mass degradation: 92.8%.

SDTA: $T_{D(Onset)}$: 192.7° C., $T_{D(max)}$: 209.4° C.

Example 24: Synthesis of [Sb(mbt)$_3$]

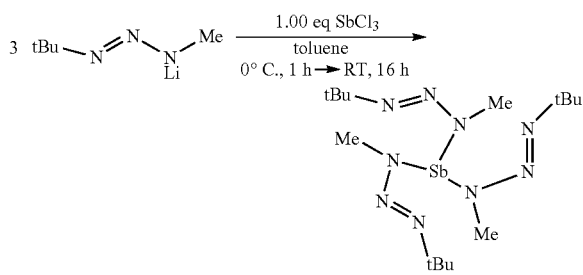

SbCl$_3$ (250 mg, 1.10 mmol, 1.00 eq) and [Li(mbt)] (400 mg, 3.30 mmol, 3.00 eq) were provided together and cooled to 0° C. With stirring, 10 mL of toluene pre-cooled to 0° C. were added. The yellow reaction mixture was stirred for 20 h at RT and the solvent removed in FV. After addition of 10 mL of n pentane, the suspension was filtered through Celite® and the solvent of the slightly yellow filtrate was removed in FV. The crude product was obtained with a yield of 63% (320 mg, 0.69 mmol) and quantitatively sublimated in FV at 60° C. The product is in the form of a colorless solid.

$^1$H-NMR ($C_6D_6$, 300 MHz, 300 K): δ/ppm=1.21 (s, 27H, CMe$_3$), 3.27 (s, 9H, NMe).

$^{13}$C-NMR ($C_6D_6$, 75 MHz, 300 K): δ/ppm=29.3 (CMe$_3$), 37.5 (NMe), 59.1 (CMe$_3$).

IR: ṽ/cm$^{-1}$=2966 (m), 2926 (w), 2867 (w), 1430 (st), 1400 (m), 1358 (m), 1272 (m), 1249 (m), 1203 (st), 1054 (m), 1015 (st), 919 (w), 785 (w), 656 (w), 606 (st), 569 (st), 483 (w), 450 (st).

Elemental analysis: for $C_{15}H_{36}SbN_3$
calculated: C: 38.81%, H: 7.82%, N: 27.15%.
found: C: 37.25%, H: 7.55%, N: 26.62%.

EI-MS: calculated for $C_{10}H_{24}SbN_6$: 349.1101 m/z, found: 349.1005 m/z.

Melting point: 112° C. (optically 5° C./min).

TGA: ($T_S$=25° C., $T_E$=900° C., 10° C./min), stages: 1 3% degradation: 134.4° C., max. degradation: 199.6° C., total mass degradation: 96.1%.

Figure 16:
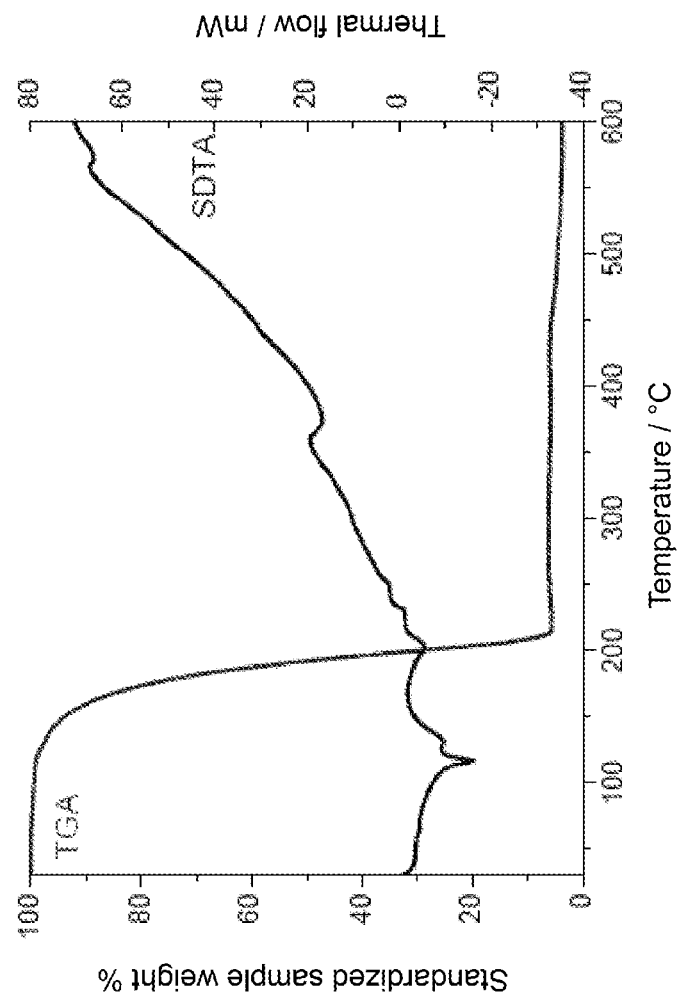

SDTA: $T_{M(Onset)}$: 110.8° C., $T_{M(max)}$: 116.3° C., $T_{D(Onset)}$: 187.2° C., $T_{D(max.)}$: 202.6° C. FIG. 16 shows a graphical representation of the TGA and SDTA measurements.

Example 25: Synthesis of [Bi(dbt)$_3$]

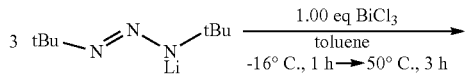

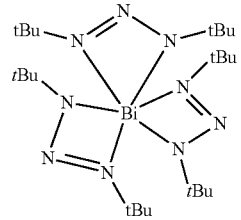

BiCl$_3$ (103 mg, 0.33 mmol, 1.00 eq) was provided in 10 mL toluene and cooled to −16° C. A solution of [Li(dbt)] (162 mg, 0.99 mmol, 3.00 eq) in 5 mL toluene was added dropwise. The brown reaction mixture was first warmed to RT and then stirred at 50° C. for 3 hours. The solid was filtered off and the red filtrate solvent removed in FV. leaving a red solid. The product was purified by sublimation in FV at 60° C. and obtained with a 61% yield (136 mg, 0.20 mmol) as a red solid.

$^1$H-NMR ($C_6D_6$, 300 MHz, 300 K): δ/ppm=1.32 (s, CMe$_3$).

$^{13}$C-NMR ($C_6D_6$, 75 MHz, 300 K): δ/ppm=30.7 (CMe$_3$), 56.7 (CMe$_3$).

TGA: ($T_S$=25° C., $T_E$=900° C., 10° C./min), stages: 1 3% degradation: 126.6° C., max. degradation: 223.6° C., total mass degradation: 57.3%.

Figure 17:
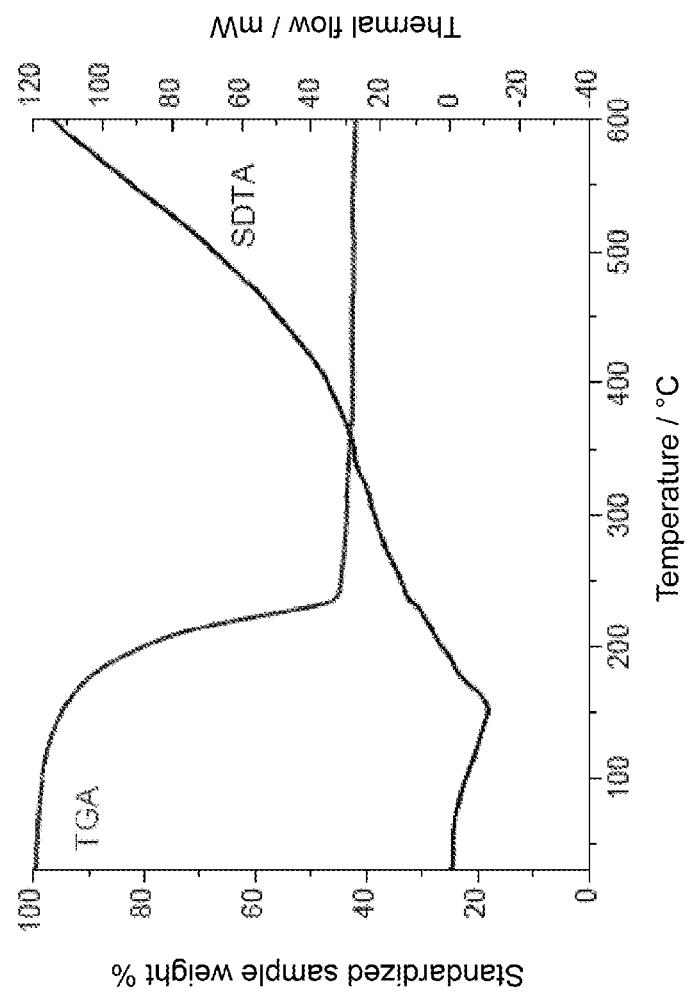

SDTA: $T_{D(Onset)}$: 102.6° C., $T_{D(max.)}$: 153.4° C. FIG. 17 shows a graphical representation of the TGA and SDTA measurements.

Example 26: Synthesis of [Bi(mbt)$_3$]

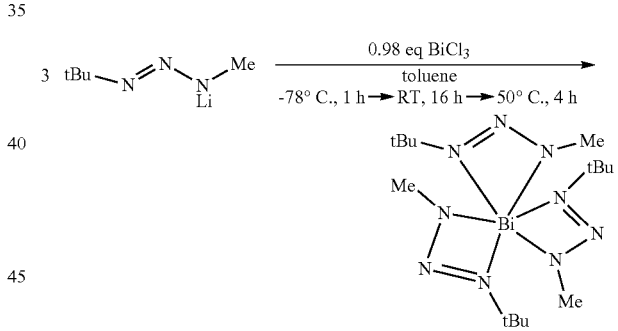

BiCl$_3$ (175 mg, 0.56 mmol, 0.98 eq) was provided in 5 mL toluene and cooled to −70° C. and blended with [Li(mbt)] (207 mg, 1.71 mmol, 3.00 eq), dissolved in 10 mL toluene. The reaction mixture was slowly warmed to RT, stirred for 16 h and then heated to 50° C. for 4 h. The solvent of the green suspension was removed in FV, the product was sublimated from the residue at 65° C. and obtained in a yield of 90% (277 mg, 50.2 mmol) as a yellow solid.

$^1$H-NMR ($C_6D_6$, 300 MHz, 300 K): δ/ppm=1.20 (s, 27H, CMe$_3$), 3.69 (s, 9H, NMe).

$^{13}$C-NMR ($C_6D_6$, 75 MHz, 300 K): δ/ppm=29.7 (CMe$_3$), 42.6 (NMe), 59.3 (CMe$_3$).

IR: ṽ/cm$^{-1}$=2965 (m), 2924 (w), 2900 (w), 2863 (w), 1455 (w), 1417 (st), 1387 (st), 1357 (st), 1283 (st), 1248 (m), 1201 (st), 1055 (w), 1015 (m), 921 (w), 785 (w), 601 (st), 566 (st), 481 (w), 435 (st).

EI-MS: calculated for $C_{10}H_{24}BiN_6$: 437.1866 m/z, found: 437.1902 m/z.

Melting point: 105° C. (visually 5° C./min).

TGA: ($T_S$=25° C., $T_E$=900° C., 10° C./min), stages: 1

3% degradation: 152.4° C., max. degradation: 231.5° C., total mass degradation: 81.9%.

Figure 18:
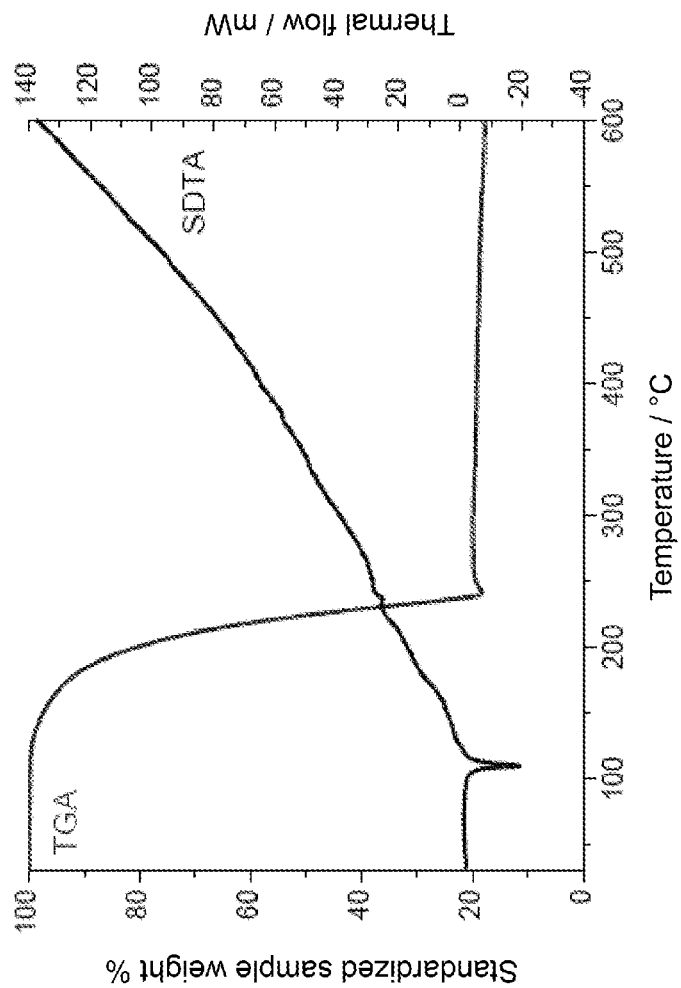

SDTA: $T_{M(Onset)}$: 106.9° C., $T_{M(max.)}$: 109.5° C., $T_{D(Onset)}$: 233.4° C., $T_{D(max.)}$: 243.4° C. FIG. 18 shows a graphical representation of the TGA and SDTA measurements RPD: Residue from TGA analysis: $2\theta_{Lit.}^{[63]}(2\theta_{obs.})$ for Bi: 22.468 (22.570), 23.794 (23.620), 27.164 (27.205), 37.955 (37.975), 39.619 (39.655), 44.554 (44.575), 45.863 (45.970), 46.020 (46.030), 46.470 (46.600), 48.700 (48.700), 56.027 (56.050), 59.325 (59.290), 61.126 (61.270), 62.181 (62.185), 62.895 (62.815), 64.513 (64.525), 67.439 (67.510), 70.786 (70.795), 71.528 (71.515), 71.885 (71.920), 73.711 (73.750), 75.333 (75.340), 76.408 (76.330), 81.143 (81.100), 85.000 (84.970), 85.341 (85.390), 87.089 (87.085), 89.582 (89.590).

Example 27: Synthesis of [Hg(mbt)$_2$]

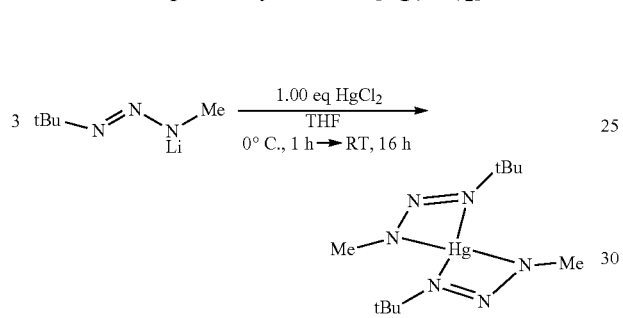

[Li(mbt)] (200 mg, 1.65 mmol, 2.00 eq) was provided in 2 mL THF and cooled to 0° C. HgCl$_2$ (224 mg, 0.83 mmol, 1.00 eq), dissolved in 8 mL THF, was added dropwise. The reaction mixture was stirred for 16 h at RT. The slightly gray suspension was concentrated to dryness, taken up in n pentane and filtered over Celite®. After removal of the solvent of the filtrate, the product was obtained as a slightly yellow viscous liquid with a yield of 12% (40 mg, 0.09 mmol).

$^1$H-NMR (C$_6$D$_6$, 300 MHz, 300 K): δ/ppm=1.28 (m, 18H, CMe$_3$), 3.31 (m, 6H, NMe).

$^{13}$C-NMR (C$_6$D$_6$, 75 MHz, 300 K): δ/ppm=31.0 (CMe$_3$), 44.1 (NMe), 57.8 (CMe$_3$).

IR: $\tilde{v}$/cm$^{-1}$=2964 (st), 2926 (m), 2903 (m), 2864 (w), 1437 (st), 1379 (m), 1360 (st), 1260 (st), 1227 (st), 1203 (st), 1095 (st), 1072 (st), 1015 (st), 922 (w), 865 (w), 799 (st), 665 (m), 608 (m), 569 (m), 475 (w).

TGA: ($T_S$=25° C., $T_E$=600° C., 10° C./min), stages: 2

3% degradation: 127.1° C., max. degradation (1st stage): 162.4° C., max. degradation (2nd stage): 358.4° C., Mass degradation (1st stage): 68.1%, Total mass degradation: 100%.

SDTA: $T_{D(Onset)}$: 143.0° C., $T_{D(max.)}$: 161.4° C.

Example 28: Synthesis of [Ce(dbt)$_3$]

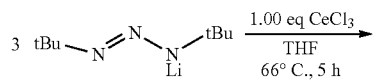

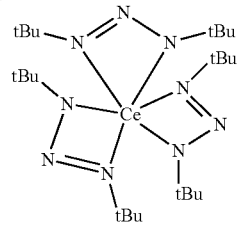

HR-EI-MS: calculated for C$_{24}$H$_{54}$CeN$_9$: 608.3557 m/z, found: 608.3566 m/z.

Examples 29 and 30: Synthesis of [Zr(dbt)$_2$(NMe$_2$)$_2$] and [Hf(dbt)$_2$(NMe$_2$)$_2$]

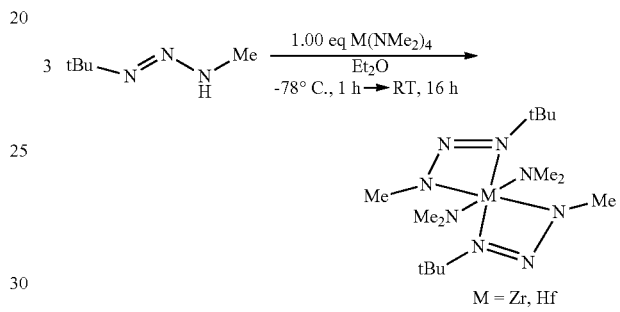

M(NMe$_2$)$_4$ (with M=Zr or Hf) was dissolved in 10 mL and/or 22 mL Et$_2$O, cooled to −78° C. and dropwise blended with Hdbt. The reaction mixture was warmed to RT and stirred for 16 h. The solvent was then removed in FV. The yellow residue was taken up in 10 mL of n hexane and the slightly turbid solution was filtered. The solvent of the filtrate was removed in a fine vacuum and the product was dried.

Example 29: [Zr(dbt)$_2$(NMe$_2$)$_2$]

Yield: 91%.

$^1$H-NMR (C$_6$D$_6$, 300 MHz, 300 K): δ/ppm=1.33 (s, 36H, CMe$_3$), 3.05 (s, 12H, NMe$_2$).

$^{13}$C-NMR (C$_6$D$_6$, 75 MHz, 300 K): δ/ppm=30.2 (CMe$_3$), 43.9 (NMe$_2$), 57.5 (CMe$_3$).

Elemental analysis: for C$_{20}$H$_{48}$ZrN$_8$ calculated: C: 48.84%, H: 9.84%, N: 22.78%.

found: C: 48.41%, H: 9.77%, N: 23.23%.

Example 30: [Hf(dbt)$_2$(NMe$_2$)$_2$]

Yield: 96%.

$^1$H-NMR (C$_6$D$_6$, 300 MHz, 300 K): δ/ppm=1.32 (s, 36H, CMe$_3$), 3.15 (s, 12H, NMe$_2$).

$^{13}$C-NMR (C$_6$D$_6$, 75 MHz, 300 K): δ/ppm=30.2 (CMe$_3$), 43.9 (NMe$_2$), 58.6 (CMe$_3$).

Elemental analysis: for C$_{20}$H$_{48}$HfN$_8$ calculated: C: 41.48%, H: 8.35%, N: 19.35%.

found: C: 40.29%, H: 8.14%, N: 19.24%.

Example 31: Synthesis of Cs(dbt)

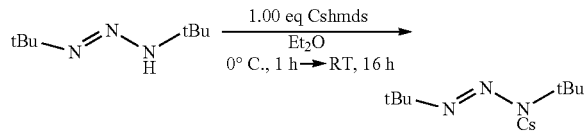

Cshmds was taken up in 10 mL Et$_2$O and blended dropwise with Hdbt at 0° C. The slightly turbid solution was warmed to RT, stirred for 16 h and filtered over Celite®. The solvent of the filtrate was removed in FV. Yield: 76%.

$^1$H-NMR (C$_6$D$_6$/THF-d$_8$ (5/1), 300 MHz, 300 K): δ/ppm=1.35 (s, CMe$_3$).

$^{13}$C-NMR (C$_6$D$_6$/THF-d$_8$ (5/1), 75 MHz, 300 K): δ/ppm=31.3 (CMe$_3$), 55.8 (CMe$_3$).

Elemental analysis: for C$_8$H$_{18}$CsN$_3$ calculated: C: 33.23%, H: 6.27%, N: 14.53%.

found: C: 32.60%, H: 6.07%, N: 14.64%.

Example 32: Synthesis of [Au$_2$(dbt)$_2$]

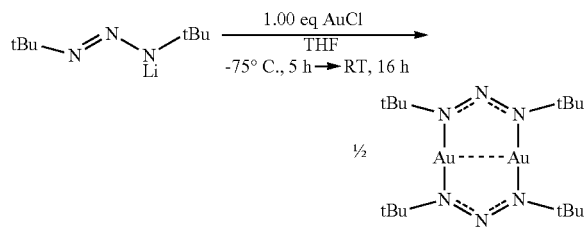

AuCl (253 mg, 1.09 mmol, 1.00 eq) was suspended in 5 mL THF, cooled to −75° C. and blended with a solution of [Li(dbt)] (179 mg, 1.09 mmol, 1.00 eq) in 10 mL THF. The reaction mixture was kept at −75° C. for 5 h, heated to RT and stirred for a further 16 h. The solvent of the brown reaction mixture was removed in a fine vacuum (FV), the residue taken up in n hexane and the resulting suspension filtered. The solvent of the filtrate was removed in FV and the residue was purified sublimatively in FV at 80° C. The product was obtained in the form of a yellow solid with a yield of 13% (50 mg, 0.14 mmol).

$^1$H-NMR (C$_6$D$_6$, 300 MHz, 300 K): δ/ppm=1.12 (s, 9H, CMe$_3$), 1.27 (s, 18H, CMe$_3$), 1.45 (s, 9H, CMe$_3$). $^{13}$C-NMR (C$_6$D$_6$, 75 MHz, 300 K): δ/ppm=30.2 (CMe$_3$), 30.4 (CMe$_3$), 31.0 (CMe$_3$), 56.5 (CMe$_3$), 60.2 (CMe$_3$), 62.4 (CMe$_3$).

IR: ṽ/cm-1=2956 (m), 2858 (w), 1469 (w), 1404 (st), 1381 (st), 1356 (st), 1317 (w), 1222 (m), 1184 (st), 1020 (w), 803 (w), 650 (m), 578 (m), 510 (w), 483 (w).

Elemental Analysis: for C$_{16}$H$_{36}$Au$_2$N$_6$ calculated: C: 27.20%, H: 5.14%, N: 11.90%; found: C: 29.77%, H: 5.75%, N: 13.46%.

HR-EI-MS: calculated for C$_{16}$H$_{36}$Au$_2$N$_6$: 706.2333 m/z, found: 706.2324 m/z.

TGA: (T$_S$=25° C., T$_E$=900° C., 10° C./min), stages: 1

3% degradation: 121.8° C., max. degradation: 221.4° C., total mass degradation: 62.0%.

Figure 19:
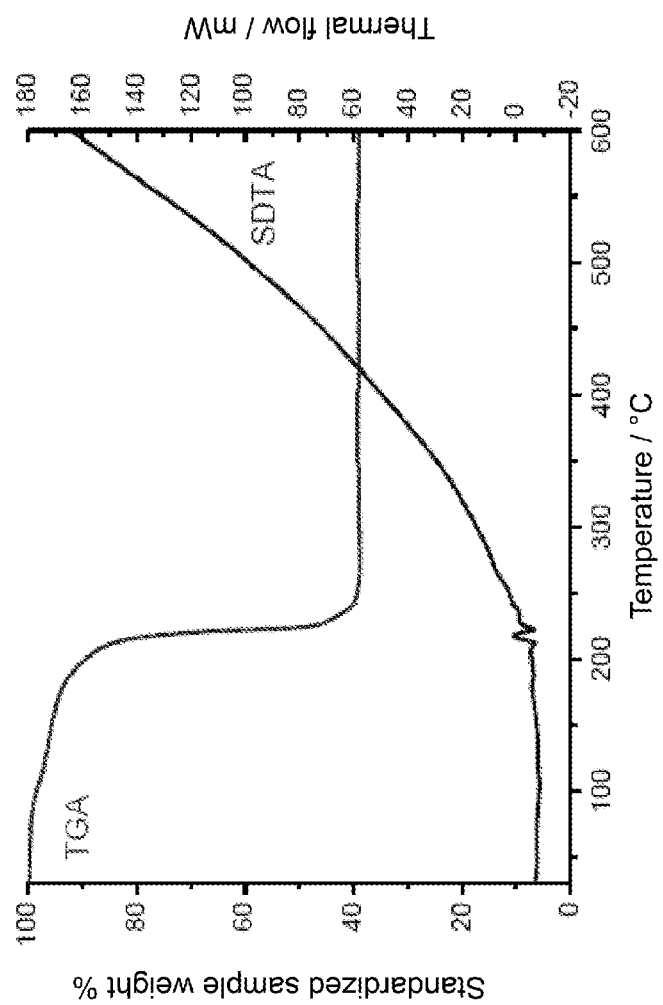

SDTA: T$_{D(Onset)}$: 212.6° C., T$_{D(max.)}$: 217.4° C. FIG. 19 shows a graphical representation of the TGA and SDTA measurements.

Example 33: Synthesis of [Ag$_4$(dbt)$_4$]

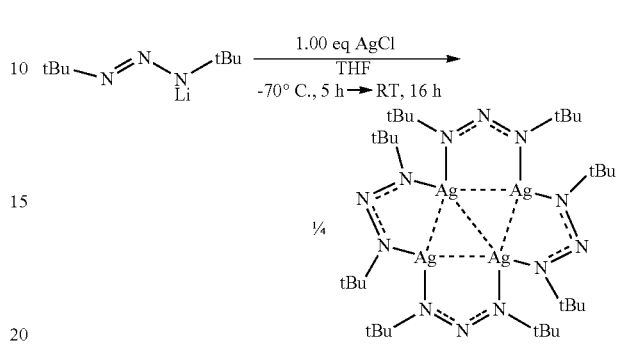

AgCl (250 mg, 1.70 mmol, 1.00 eq) was provided in 5 mL THF, cooled to −70° C., and a solution of [Li(dbt)] (277 mg, 1.70 mmol, 1.00 eq) was added in 10 mL THF. The deep-brown reaction mixture was warmed to RT, stirred for 16 h and then freed of all volatile constituents in FV. The residue was taken up in 10 ml of n hexane and the weakly reddish suspension was filtered. The solvent of the filtrate was removed in FV, the residue was purified by sublimation at 90° C. in FV and the product was obtained as a colorless solid with a yield of 47% (178 mg, 0.20 mmol).

Reaction Mixture and Product should be Handled in the Absence of Light.

$^1$H-NMR (C$_6$D$_6$, 300 MHz, 300 K): δ/ppm=1.27 (s, 36H, CMe$_3$), 1.43 (s, 36H, CMe$_3$).

$^{13}$C-NMR (C$_6$D$_6$, 75 MHz, 300 K): δ/ppm=31.0 (CMe$_3$), 31.9 (CMe$_3$).

IR: ṽ/cm$^{-1}$=2957 (m), 2859 (w), 1471 (w), 1403 (st), 1354 (st), 1316 (m), 1222 (st), 1179 (st), 1101 (w), 1055 (w), 1016 (w), 921 (w), 888 (w), 802 (w), 766 (w), 642 (st), 574 (st), 503 (w), 478 (m), 411 (w).

Elemental Analysis: for C$_{16}$H$_{48}$Ag$_4$N$_{12}$ calculated: C: 36.38%, H: 6.87%, N: 15.91%; found: C: 36.79%, H: 6.93%, N: 16.60%.

TGA: (T$_S$=25° C., T$_E$=700° C., 10° C./min), stages: 1

3% degradation: 205.4° C., max. degradation: 256.6° C., total mass degradation: 78.7%.

SDTA: T$_{D(Onset)}$: 212.5° C., T$_{D(max.)}$: 215.2° C.

Figure 20:
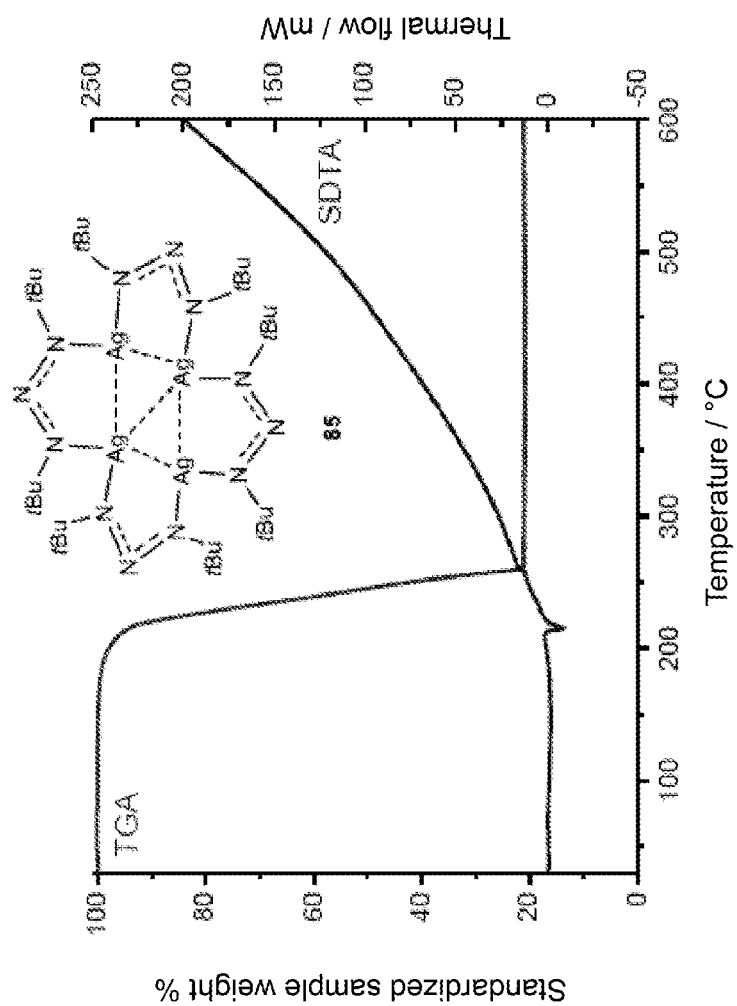

FIG. 20 shows a graphical representation of the TGA and SDTA measurements.

Example 34: Synthesis of [Ga(mbt)Me$_2$]

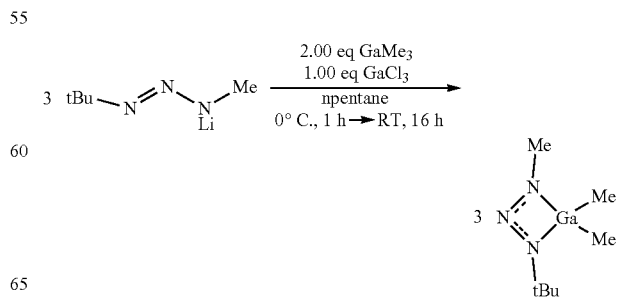

GaMe₃ (146 mg, 1.27 mmol, 2.00 eq) was provided in 5 mL n pentane and added at 0° C. to a solution of GaCl₃ (112 mg, 0.64 mmol, 1.00 eq) in 10 mL n pentane. The colorless solution was warmed to RT, stirred for 16 h, re-cooled to 0° C. and added to a solution of [Li(mbt)] (231 mg, 1.91 mmol, 3.00 eq) in 10 mL of n pentane. The reaction mixture was warmed to RT and stirred for 16 h. The solvent of the suspension was removed in FV and the desired product isolated from the residue by condensation in FV. The product was obtained in the form of a colorless liquid with a yield of 57% (233 mg, 1.09 mmol).

¹H-NMR (C₆D₆, 300 MHz, 300 K): δ/ppm=0.05 (s, 6H, GaMe₂), 1.17 (s, 18H, CMe₃), 3.03 (s, 3H, NMe).

¹³C-NMR (C₆D₆, 75 MHz, 300 K): δ/ppm=−5.6 (GaMe₂), 29.7 (CMe₃), 39.4 (NMe).

IR: ṽ/cm⁻¹=2969 (m), 2902 (w), 1524 (w), 1459 (w), 1435 (m), 1361 (st), 1309 (m), 1271 (w), 1199 (st), 1068 (m), 1026 (w), 955 (w), 930 (w), 866 (st), 787 (w), 737 (st), 688 (m), 646 (st), 572 (st), 534 (st), 481 (w), 460 (m), 438 (w).

TGA: (T$_S$=25° C., T$_E$=450° C., 10° C./min), stages: 1
3% degradation: 63.2° C., max. degradation: 100.9° C., total mass degradation: 87.4%.

SDTA: T$_{D(Onset)}$: 81.6° C., T$_{D(max.)}$: 100.3° C.

Figure 21:
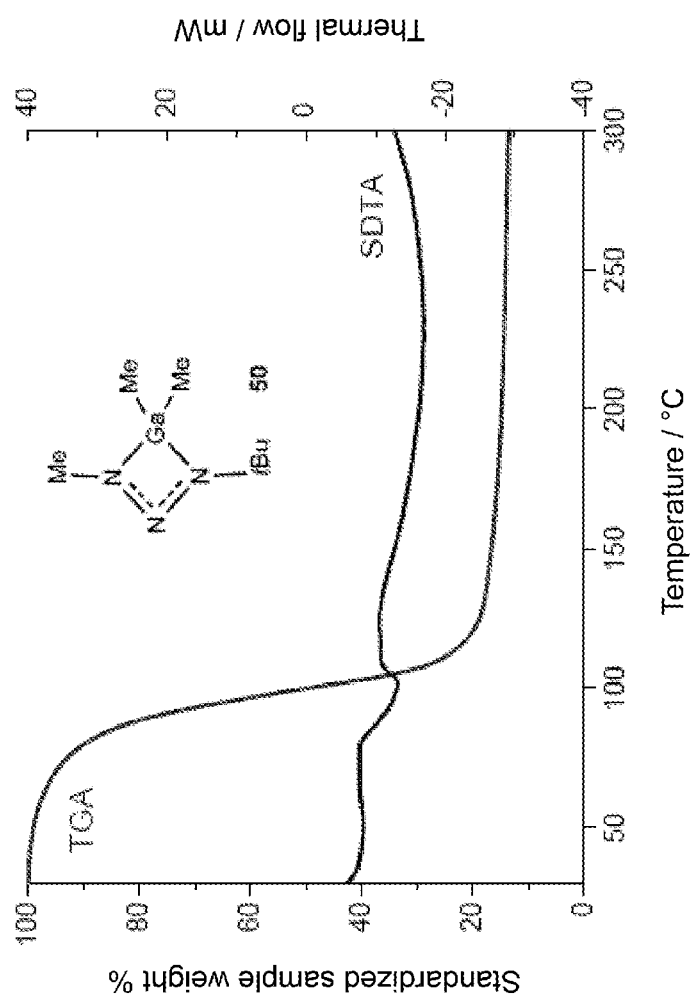

FIG. 21 shows a graphical representation of the TGA and SDTA measurements.

Example 35: Synthesis of [Ga(dbt)Me₂]

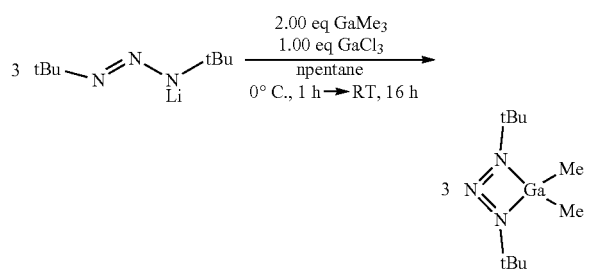

GaMe₃ (181 mg, 1.58 mmol, 2.00 eq) was provided in 10 mL n pentane and added at 0° C. to a solution of GaCl₃ (139 mg, 0.79 mmol, 1.00 eq) in 10 mL n pentane. The reaction mixture was warmed to RT and stirred for 16 h. At 0° C., a solution of [Li(dbt)] (387 mg, 2.37 mmol, 3.00 eq) was added dropwise, and the precipitation of a colorless solid was observed instantly. The suspension was slowly warmed to RT and stirred for 16 h. The solvent was removed in the fine vacuum (FV) and the product was condensed in the form of a colorless liquid from the residue in FV. The product was obtained with a yield of 43% (261 mg, 1.02 mmol).

¹H-NMR (C₆D₆, 300 MHz, 300 K): δ/ppm=0.10 (s, 6H, GaMe₂), 1.17 (s, 18H, CMe₃).

¹³C-NMR (C₆D₆, 75 MHz, 300 K): δ/ppm=−5.2 (GaMe₂), 29.7 (CMe₃), 55.8 (NMe).

IR: ṽ/cm⁻¹=2967 (st), 2870 (w), 1459 (w), 1387 (w), 1361 (m), 1295 (st), 1217 (st), 1029 (w), 924 (w), 767 (m), 699 (m), 630 (m), 583 (st), 545 (st), 484 (m).

TGA: (T$_S$=25° C., T$_E$=450° C., 10° C./min), stages: 1
3% degradation: 64.2° C., max. degradation: 116.0° C., total mass degradation: 89.9%.

SDTA: T$_{D(onset)}$: 79.5° C., T$_{D(max.)}$: 115.7° C.

Figure 22:
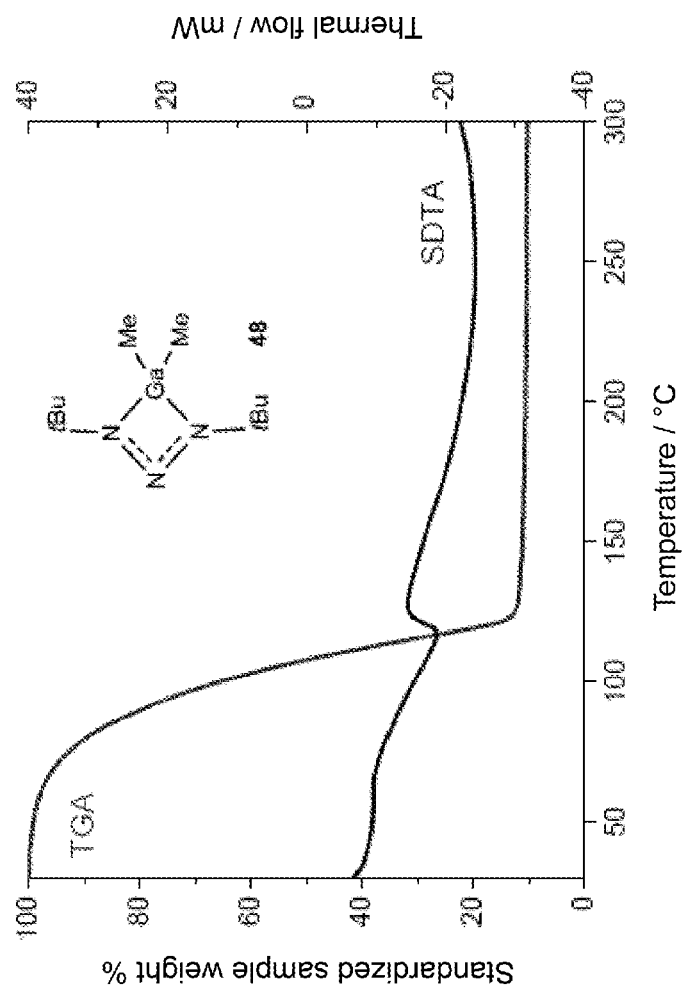

FIG. 22 shows a graphical representation of the TGA and SDTA measurements.

Example 36: Synthesis of [Al(mbt)₃]

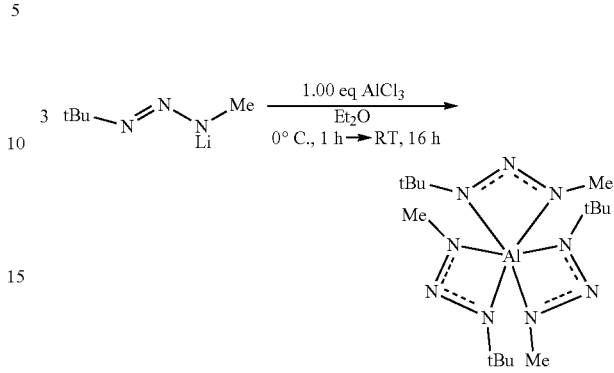

A solution of AlCl₃ (131 mg, 0.98 mmol, 1.00 eq) in 10 mL Et₂O was added dropwise at 0° C. to a solution of [Li(mbt)] (357 mg, 2.95 mmol, 3.00 eq) in 10 mL Et₂O. The colorless reaction mixture was slowly warmed to RT, stirred for 16 h, and then filtered. The residue was extracted with 10 mL Et₂O, and the filtrate evaporated to dryness in FV. The pale-yellow solid was sublimated in fine vacuum at 45° C. and the product was obtained with a yield of 21% (76 mg, 0.21 mmol).

¹H-NMR (C₆D₆, 300 MHz, 300 K): δ/ppm=1.31 (s, 27H, CMe₃), 3.16 (s, 9H, NMe).

¹³C-NMR (C₆D₆, 75 MHz, 300 K): δ/ppm=30.3 (CMe₃), 37.5 (NMe), 55.8 (CMe₃).

²⁷Al-NMR (C₆D₆, 130 MHz, 300 K): δ/ppm=28.1.

IR: ṽ/cm⁻¹=2968 (m), 2926 (m), 2896 (m), 2802 (w), 1473 (w), 1457 (w), 1415 (w), 1387 (w), 1358 (m), 1300 (st), 1263 (st), 1229 (st), 1199 (st), 1106 (w), 1025 (w), 954 (w), 796 (w), 625 (m), 572 (w), 524 (st), 435 (w).

Elemental Analysis: for C₁₅H₃₆AlN₉
calculated: C: 48.76%, H: 9.82%, N: 34.12%; found: C: 47.95%, H: 9.63%, N: 33.55%.

TGA: (T$_S$=25° C., T$_E$=700° C., 10° C./min), stages: 1
3% degradation: 124.6° C., max. degradation: 216.1° C., total mass degradation: 96.4%.

SDTA: T$_{M(Onset)}$: 45.6° C., T$_{M(max.)}$: 49.7° C., T$_{D(onset)}$: 205.1° C., T$_{D(max.)}$: 218.8° C.

Figure 23:
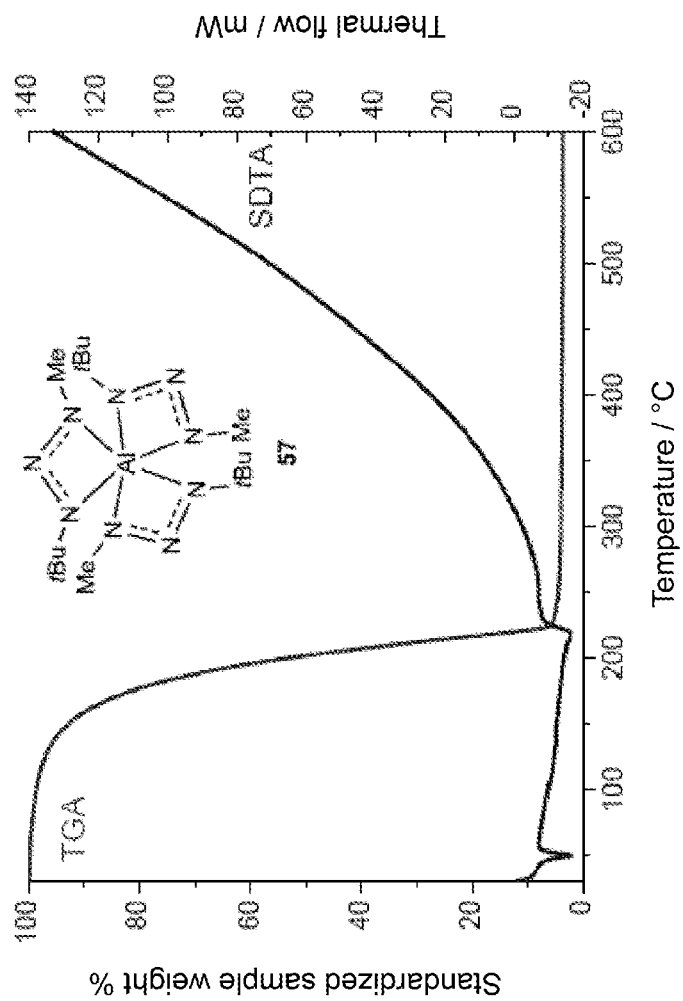

FIG. 23 shows a graphical representation of the TGA and SDTA measurements.

Example 37: Synthesis of [Al(dbt)₃]

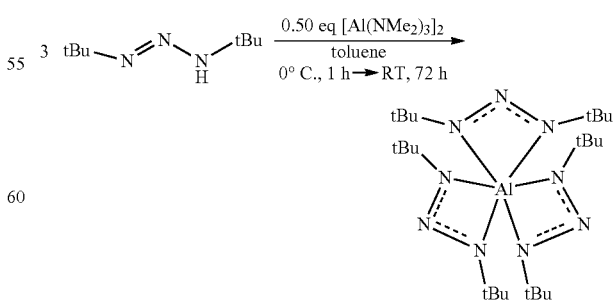

[Al(NMe₂)₃]₂ (154 mg, 0.97 mmol, 0.50 eq) was provided in 10 mL toluene, cooled to 0° C. and blended dropwise with H(dbt) (458 mg, 2.91 mmol, 3.00 eq). The reaction solution was stirred for 1 h at 0° C. and was allowed to warm to RT. A gas evolution was observed. After the yellow solution was stirred for 16 h at RT, a pale-yellow solid was obtained by removing the solvent in FV. The crude product was purified sublimatively at 55° C. in FV and isolated as a colorless solid with a yield of 51% (244 mg, 0.49 mmol).

$^1$H-NMR (C$_6$D$_6$, 300 MHz, 300 K): δ/ppm=1.38 (s, CMe$_3$).

$^{13}$C-NMR (C$_6$D$_6$, 75 MHz, 300 K): δ/ppm=31.2 (CMe$_3$), 57.2 (CMe$_3$).

$^{27}$Al-NMR (C$_6$D$_6$, 130 MHz, 300 K): δ/ppm=24.6.

IR: ṽ/cm$^{-1}$=2972 (m), 2929 (s), 2870 (s), 2812 (s), 2767 (s), 1474 (s), 1387 (s), 1360 (m), 1302 (st), 1257 (st), 1201 (st), 1160 (st), 1069 (s), 1034 (s), 977 (m), 899 (s), 845 (s), 767 (s), 627 (m), 570 (m), 543 (st), 438 (s).

Elemental Analysis: calculated for C$_{24}$H$_{54}$AlN$_9$: C: 58.15%, H: 10.98%, N: 25.43%; found: C: 58.25%, H: 10.13%, N: 24.32%.

TGA: (T$_S$=25° C., T$_E$=700° C., 10° C./min), stages: 1

3% degradation: 126.8° C., max. degradation: 172.6, 302.0° C., total mass degradation: 95.3%.

Figure 24:
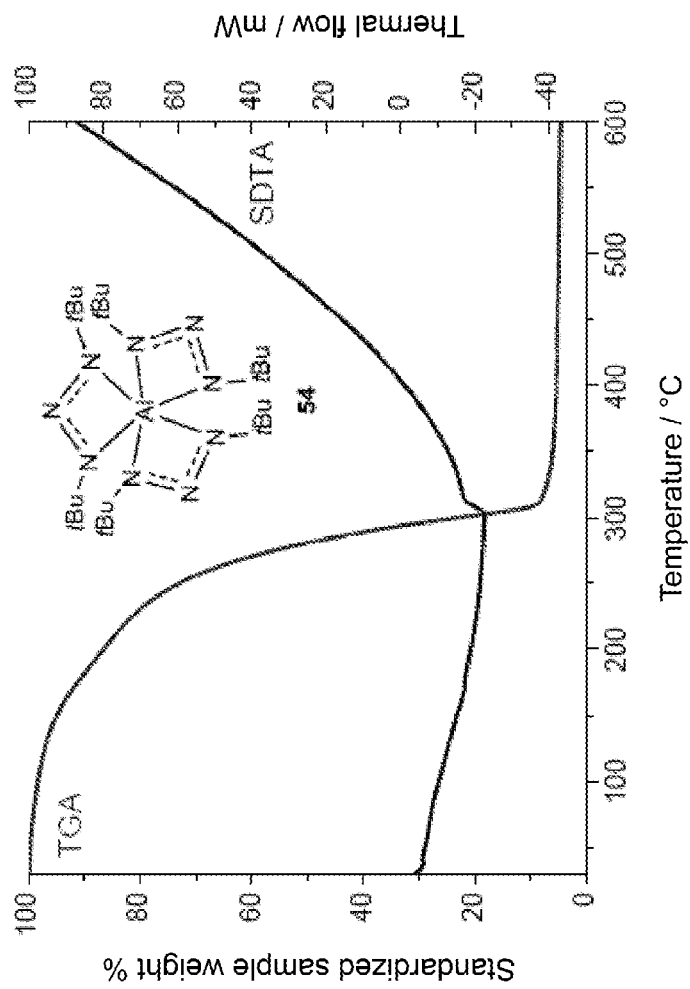

SDTA: T$_{D(Onset)}$: 270.0° C., T$_{D(max)}$: 302.7° C. FIG. 24 shows a graphical representation of the TGA and SDTA measurements.

BIBLIOGRAPHY

[1] J. C. Brand, B. P. Roberts, *J. Chem. Soc. Chem. Comm.* 1981, 748-749.
[2] R. H. J. Smith, C. J. Michejda, *Synthesis* 1983, 476-477.
[3] R. H. J. Smith, B. D. Wladowski, A. F. Mehl, M. J. Cleveland, E. A. Rudrow, G. N. Chmurny, C. J. Michejda, *J. Org. Chem.* 1989, 54, 1036-1042.
[4] D. H. Sieh, D. J. Wilbur, C. J. Michejda, *J. Am. Chem. Soc.* 1980, 3883-3887.
[5] Soussi, K., Mishra, S, Jeanneau, E, Millet, J.-M., Daniele, S., *Dalton Transactions* 2017, 46, 38, 13055 to 13064
[6] C. Lego, B. Neumüller, *Z. Anorg. Allg. Chem.* 2011, 637, 1784-1789.
[7] P. Gantzel, P. J. Walsh, *Inorg. Chem.* 1998, 37, 3450-3451.
[8] D. Kalden, S. Krieck, H. Görls, M. Westerhausen, *Dalt. Trans.* 2015, 44, 8089-8099.
[9] H. S. Lee, S.-O. Hauber, D. Vindus, M. Niemeyer, *Inorg. Chem.* 2008, 47, 4401-4412.
[10] S. L. Hyui, M. Niemeyer, *Inorg. Chem.* 2006, 45, 6126-6128.
[11] F. E. Brinckman, H. S. Haiss, R. A. Robb, *Inorg. Chem.* 1965, 4, 936-942.
[12] J. T. Leman, A. R. Barron, J. W. Ziller, R. M. Kren, *Polyhedron* 1989, 8, 1909-1912.
[13] J. T. Leman, H. A. Roman, A. R. Barron, *J. Chem. Soc. Dalt. Trans.* 1992, 1, 2183.
[14] M. L. Cole, A. J. Davies, C. Jones, P. C. Junk, A. I. McKay, A. Stasch, *Z. Anorg. Allg. Chem.* 2015, 641, 2233-2244.
[15] S. G. Alexander, M. L. Cole, C. M. Forsyth, S. K. Furfari, K. Konstas, *Dalt. Trans.* 2009, 2326-2336.
[16] J. T. Leman, J. Braddock-Wilking, A. J. Coolong, A. R. Barron, *Inorg. Chem.* 1993, 32, 4324-4336.
[17] I. A. Guzei, L. M. Liable-Sands, A. L. Rheingold, C. H. Winter, *Polyhedron* 1997, 16, 4017-4022.
[18] V. C. Gibson, D. F. Reardon, A. K. Tomov, 2004, WO 2004063233.
[19] E. Hartmann, J. Strahle, *J. Inorg. Gen. Chem.* 1990, 583, 31-40.
[20] I. D. Brown, J. D. Dunitz, *Acta Cryst.* 1961, 14, 480-485.
[21] L. R. Falvello, E. P. Urriolabettia, U. Mukhopadhyay, D. Ray, *Acta Cryst. Comm.* 1999, C55, 170-172.
[22] H. S. Lee, M. Niemeyer, *Inorg. Chim. Acta* 2011, 374, 163-170.
[23] A. L. Johnson, A. M. Willcocks, S. P. Richards, *Inorg. Chem.* 2009, 48, 8613-8622.
[24] E. Pfeiffer, M. W. Kokkes, K. Vrieze, *Transit. Met. Chem.* 1979, 4, 389-393.
[25] M. Venter, I. Haiduc, L. David, O. Cozar, *J. Mol. Struct.* 1997, 408-409, 483-486.
[26] F. A. Cotton, X. Feng, *Inorg. Chem.* 1989, 28, 1180-1183.
[27] J. G. M. van der Linden, A. H. Dix, E. Pfeiffer, *Inorg. Chim. Acta* 1980, 39, 271-274.
[28] S. F. Colson, S. D. Robinson, *Inorg. Chim. Acta Lett.* 1988, 149, 13-14.
[29] S. F. Colson, S. D. Robinson, M. Motevalli, M. B. Hursthouse, *Polyhedron* 1988, 7, 1919-1924
[30] J. A. Cabeza, J. M. Fernhdez-Colinas, *Coord. Chem. Rev.* 1993, 126, 319-336.
[31] C. J. Weiss, T. J. Marks, *Dalt. Trans.* 2010, 39, 6576.
[32] B. Liu, D. Cui, *Dalt. Trans.* 2009, 550-556.
[33] P. J. Eulgem, A. Klein, N. Maggiarosa, D. Naumann, R. W. H. Pohl, *Chem. Eur. J.* 2008, 14, 3727-3736.
[34] S. G. Alvarez, M. T. Alvarez, *Synthesis* 1997, 4, 413-414.
[35] P. Margaretha, S. Solar, O. E. Polansky, *Angew. Chemie—Int. Ed.* 1971, 10, 412-413.
[36] P. Margaretha, S. Solar, O. E. Polansky, *Angew. Chemie* 1971, 11, 410.
[37] J. C. Bottaro, P. E. Penwell, R. J. Schmitt, *Synth. Commun.* 1997, 27, 1465-1467.

The invention claimed is:

1. Method for the production of coated substrates, comprising the steps of:
   a) providing a metal complex having at least one ligand L with the formula R$^1$—N$_3$—R$^2$, wherein R$^1$ and R$^2$ are hydrocarbon radicals, for depositing the metal or a compound of the metal from the gas phase, and
   b) depositing the metal or a compound of the metal on the surface of the substrate by metal-organic vapor deposition,
   wherein the metal is selected from In, Co, Cu, Al, Ga, Tl and La, and
   wherein the metal complex decomposes in the gas phase at a temperature which is not more than 100° C. above the sublimation temperature or evaporation temperature, wherein the metal complex of formula (2):

$$M[(L^1)_a X_d] \qquad (2)$$

wherein
L$^1$ has the formula R$^1$—N$_3$—R$^2$, wherein R$^1$ and R$^2$ are alkyl radicals with 1 to 12 C atoms,
X is selected from H, halogen, CO and alkyl having 1 to 6 C atoms,
a=3,
d=0 or 1.

2. Method according to claim 1, wherein the method is a metal-organic chemical vapor deposition (MOCVD).

3. Method according to claim 1, wherein the method is a metal-organic gas phase epitaxy (MOVPE).

4. Method according to claim 1, wherein the compound of the metal is selected from semiconductor compounds, alloys, nitrides, phosphides, arsenids and silicides.

5. Method according to claim 1, wherein the metal complex is sublimated or evaporated without decomposition taking place.

6. Method according to claim 1, wherein $R^1$ and $R^2$ has, independently of one another, 1 to 15 C atoms.

7. Method according to claim 1, wherein $R^1$ and $R^2$ has, independently of one another, 1 to 6 C atoms.

8. Method according to claim 1, wherein $R^1$ and $R^2$ are selected from methyl, ethyl, propyl, isopropyl, tert-butyl and n-propyl.

9. Method according to claim 1, wherein the metal is selected from In, Cu, Al, Ga, Tl and La.

10. Method for the production of coated substrates, comprising the steps of:
    a) providing a metal complex having at least one ligand L with the formula $R^1$—$N_3$—$R^2$, wherein $R^1$ and $R^2$ are hydrocarbon radicals, for depositing the metal or a compound of the metal from the gas phase, and
    b) depositing the metal or a compound of the metal on the surface of the substrate by metal-organic vapor deposition, and wherein the metal complex decomposes in the gas phase at a temperature which is not more than 100° C. above the sublimation temperature or evaporation temperature, wherein the metal complex is of formula (4)

$$M[(L^1)_3] \qquad (4)$$

wherein $L^1$ has the formula $R^1$—$N_3$—$R^2$, wherein $R^1$ and $R^2$ are alkyl radicals with 1 to 12 C atoms, and M=In, Tl or La;

or wherein the metal complex is of formula (5)

$$M_x(L^1)_a \qquad (5)$$

wherein $L^1$ has the formula $R^1$—$N_3$—$R^2$, wherein $R^1$ and $R^2$ are alkyl radicals with 1 to 12 C atoms, X is an integer between 1 and 4, and a is an integer between 3 and 8, with the proviso that a/x=1 or 2, and M=Co or Cu.

* * * * *